US010689478B2

(12) United States Patent
Miyagi et al.

(10) Patent No.: US 10,689,478 B2
(45) Date of Patent: Jun. 23, 2020

(54) AMIDATE COMPOUND, CATALYST FOR POLYURETHANE PRODUCTION, AND METHOD FOR PRODUCING POLYURETHANE RESIN

(71) Applicant: KOEI CHEMICAL COMPANY, LIMITED, Chiba (JP)

(72) Inventors: Motoyoshi Miyagi, Chiba (JP); Shingo Nitta, Chiba (JP); Hitomi Tsuboi, Chiba (JP); Shogo Takahashi, Chiba (JP)

(73) Assignee: KOEI CHEMICAL COMPANY, LIMITED, Chiba (JP)

( * ) Notice: Subject to any disclaimer, the term of this patent is extended or adjusted under 35 U.S.C. 154(b) by 0 days.

(21) Appl. No.: 16/322,209

(22) PCT Filed: Aug. 3, 2017

(86) PCT No.: PCT/JP2017/028314

§ 371 (c)(1),
(2) Date: Jan. 31, 2019

(87) PCT Pub. No.: WO2018/025970

PCT Pub. Date: Feb. 8, 2018

(65) Prior Publication Data

US 2019/0177464 A1 Jun. 13, 2019

(30) Foreign Application Priority Data

Aug. 4, 2016 (JP) ................................ 2016-153676
Mar. 31, 2017 (JP) ................................ 2017-072940

(51) Int. Cl.
*C07D 233/90* (2006.01)
*B01J 31/02* (2006.01)
*C08G 18/20* (2006.01)
*C08G 18/18* (2006.01)

(52) U.S. Cl.
CPC ....... *C08G 18/2081* (2013.01); *C07D 233/90* (2013.01); *C08G 18/18* (2013.01); *C08G 18/2027* (2013.01)

(58) Field of Classification Search
CPC ........................... C07D 233/90; C07D 403/12
USPC ........................... 548/336.1, 312.7; 502/167
See application file for complete search history.

(56) References Cited

U.S. PATENT DOCUMENTS

2011/0046301 A1 2/2011 Mignani et al.

FOREIGN PATENT DOCUMENTS

| | | |
|---|---|---|
| JP | 5-45763 | 2/1993 |
| JP | 2013-526630 | 6/2013 |
| SG | 185398 | 12/2012 |
| WO | 2009/013344 | 1/2009 |
| WO | 2018/181753 | 10/2018 |

OTHER PUBLICATIONS

International Search Report dated Sep. 12, 2017 in International (PCT) Application No. PCT/JP2017/028314.

Sturada et al., "Electron-Deficient Heteroarenium Salts: An Organocatalytic Tool A for Activation of Hydrogen Peroxide in Oxidations", Journal of Organic Chemistry, vol. 80, No. 5, 2015, pp. 2676-2699, ISSN:0022-3263.

Schmidt et al., "Imidazol-2-and-4-ylidene by decarboxylation. Studies on the cross-conjugated mesomeric betaine-alkaloid norzooanemonine and its pseudo-cross-conjugated isomer", Organic & Biomolecular Chemistry, vol. 6, No. 2, 2008, pp. 287-295, ISSN:1477-0520.

Coutelier et al., "N-Heterocyclic Carbene-Catalyzed Synthesis of Polyurethanes", Polymer Preprints, vol. 52, No. 2, 2011, pp. 290-291.

(Continued)

*Primary Examiner* — Charanjit Aulakh
(74) *Attorney, Agent, or Firm* — Wenderoth, Lind & Ponack, L.L.P.

(57) ABSTRACT

Provided is an amidate compound represented by the formula (1):

(1)

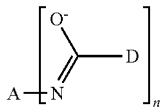

wherein A is a substituted or unsubstituted hydrocarbon group, n is an integer of 1 or more, and D is a nitrogen-containing organic group represented by the formula (2):

(2)

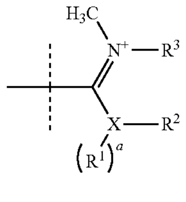

wherein $R^1$, $R^2$, and $R^3$ are the same or different, and are each a hydrocarbon group that may contain a heteroatom; some or all of $R^1$, $R^2$, and $R^3$ may be bonded together to form a ring structure; X is a nitrogen atom, an oxygen atom, or a sulfur atom; and a is 0 or 1, wherein a is 1 when X is a nitrogen atom, and a is 0 when X is an oxygen atom or a sulfur atom.

15 Claims, No Drawings

(56) References Cited

OTHER PUBLICATIONS

Bantu et al., "$C0_2$, Magnesium, Aluminum, and Zinc Adducts of N-Heterocyclic Carbenes as (Latent) Catalysts for Polyurethane Synthesis", European Journal of Inorganic Chemistry, No. 13, 2009, pp. 1970-1976, ISSN: 1434-1948.
Bantu et al., "$C0_2$ and $Sn^{II}$ adducts of N-Heterocyclic Carbenes as Delayed-Action Catalysts for Polyurethane Synthesis", Chemistry—A European Journal, vol. 15, No. 13, 2009, pp. 3103-3109, ISSN:0947-6539.
Winkler et al., "Preparation and reactivity of an isolable N-heterocyclic carbene-borane", Journal of Organometallic Chemistry, vol. 775, 2015, pp. 164-168, ISSN: 0022-328X.
Li et al., "Amine-Linked N-Heterocyclic Carbenes: The Importance of an Pendant Free Amine Auxiliary in Assisting the Catalytic Reaction", Chemistry—An Asian Journal, vol. 6, No. 6, 2011, pp. 1520-1524, ISSN:1861-4728.
Wang et al., "High-Spin Iron(II) Alkynyl Complexes with N-Heterocyclic Carbene Ligation: Synthesis, Characterization, and Reactivity Study", Organometallics, vol. 4, No. 12, 2015, pp. 2775-2782, ISSN:0276-7333.
"Structure and physical properties of polyurethane, and higherfunction and application development" Technical InformationInstitute Co., Ltd., 1998, p. 325, with partial English translation.
Coutalier et al., "N-Heterocyclic carbene-catalysed synthesis of polyurethanes", Polymer Chemistry, vol. 3, 2012, pp. 605-608.
Baiocchi et al., "1,2,4-Oxadiazoles. Xi (1). An Intermediate in the Isomerization from Nitrones to Amides", J. Heterocyclic Chem., vol. 16, pp. 1477-1481 (1979).
Temprado et al., "Synthesis, structure, and thermochemistry of adduct formation between N-heterocyclic carbenes and isocyanates or mesitylnitrile oxide", Struct Chem, vol. 24, pp. 2059-2068 (2013).
Extended European Search Report dated Feb. 7, 2020 in corresponding European Patent Application No. 17837071.4.

AMIDATE COMPOUND, CATALYST FOR POLYURETHANE PRODUCTION, AND METHOD FOR PRODUCING POLYURETHANE RESIN

TECHNICAL FIELD

The present invention relates to an amidate compound, a catalyst for polyurethane production, and a method for producing a polyurethane resin.

BACKGROUND ART

Polyurethane resins are produced by the reaction of polyols and organic polyisocyanates in the presence of a catalyst and optionally additives, such as a foaming agent, a surfactant, and a crosslinking agent. Polyurethane resins have excellent adhesion to base materials, flexibility, weather resistance, etc., and are thus widely used for applications, such as paints and adhesives for vehicles, buildings, household appliances, heavy anticorrosion and plastics paints.

Examples of catalysts used in the production of polyurethane resins include organic tin catalysts, such as dibutyltin dilaurate and tin octanoate (NPL 1). However, organic tin catalysts are highly toxic, and their properties hazardous to the environment and human bodies are problematic. There have already been movements mainly in Europe to regulate the use of organic tin catalysts in the production of polyurethane resins. There has been strong demand for alternative catalysts for organic tin catalysts.

In order to solve this problem, there is reportedly a method using an N-heterocyclic carbene as a catalyst in the polymerization reaction of an aliphatic diisocyanate and an aliphatic diol (NPL 2). However, such carbenes are generally compounds that are unstable against oxygen and water. Further, it is necessary to handle them in special equipment, such as glove boxes. Accordingly, they were not satisfactory in terms of practical aspects.

As a method for solving this problem, there is a known method that uses $CO_2$ adducts of N-heterocyclic carbenes as thermally latent catalysts for polyurethane production (NPL 3). However, $CO_2$ adducts of N-heterocyclic carbenes are decomposed by heat. Accordingly, when they act as catalysts, $CO_2$ gas is generated as their decomposed product; thus, there is a problem that voids are formed particularly when they are used for paint applications. Moreover, as a result of examination, the present inventors found that $CO_2$ adducts of N-heterocyclic carbenes are rapidly hydrolyzed at 80° C. in the presence of water (see the Evaluation Examples, provided later). In light of the above, the use of $CO_2$ adducts of N-heterocyclic carbenes as thermally latent catalysts for polyurethane production still has problems that should be solved.

Furthermore, the $CO_2$ adducts of N-heterocyclic carbenes disclosed in NPL 3 have bulky substituents, such as 2,4,6-trimethylphenyl groups, on two nitrogen atoms of the N-heterocyclic carbenes. Such compounds require complicated production processes, and are industrially disadvantageous.

CITATION LIST

Non-Patent Literature

NPL 1: "Structure and physical properties of polyurethane, and higher function and application development," Technical Information Institute Co., Ltd., 1998, page 325

NPL 2: Polymer Chemistry 2012, Vol. 3, pp. 605-608

NPL 3: Chemistry A European Journal, 2009, Vol. 15, pp. 3103-3109

SUMMARY OF INVENTION

Technical Problem

The present invention has been made in consideration of the above background art. An object of the present invention is to provide a catalyst for polyurethane production that does not produce $CO_2$ gas when used as a catalyst for polyurethane production, and that is easy to handle and produce.

Solution to Problem

As a result of intensive studies to achieve the above object, the present inventors found that when a compound represented by the formula (1) was used as a catalyst for polyurethane production, it was stably present at a low temperature, had heat latency with sufficient reactivity at a high temperature, and was stable at 80° C. in the presence of water and easy to handle. Thus, the present invention has been completed.

Specifically, the present invention includes the following [1] to [19].

[1] An amidate compound represented by the formula (1):

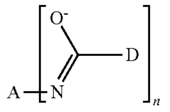

(1)

wherein A is a substituted or unsubstituted hydrocarbon group, n is an integer of 1 or more, and D is a nitrogen-containing organic group represented by the formula (2):

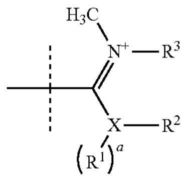

(2)

wherein $R^1$, $R^2$, and $R^3$ are the same or different, and are each a hydrocarbon group that may contain a heteroatom; some or all of $R^1$, $R^2$, and $R^3$ may be bonded together to form a ring structure; X is a nitrogen atom, an oxygen atom, or a sulfur atom; and a is 0 or 1, wherein a is 1 when X is a nitrogen atom, and a is 0 when X is an oxygen atom or a sulfur atom;

provided that 1,3-dimethylimidazolium-2-N-(p-chlorophenyl)amidate and 1,3-dimethylimidazolium-2-N-(3',5'-dichlorophenyl)amidate are excluded.

[2] The amidate compound according to [1], wherein A is an unsubstituted hydrocarbon group or a hydrocarbon group having at least one substituent selected from a fluorine atom, an alkylamino group, a dialkylamino group, an alkoxy group, an aryloxy group, a nitro group, a cyano group, a sulfonyl group, or an isocyanate group.

[3] The amidate compound according to [1] or [2], wherein n is an integer of 1 to 6.

[4] The amidate compound according to [1], wherein the amidate compound represented by the formula (1) is an amidate compound represented by the following formula (1-1), (1-2), or (1-3):

Formula (1-1)

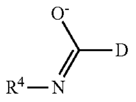

(1-1)

wherein $R^4$ is a substituted or unsubstituted hydrocarbon group, and D is as defined above;

Formula (1-2)

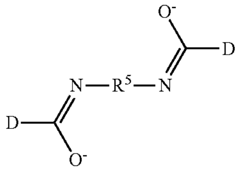

(1-2)

wherein $R^5$ is a substituted or unsubstituted hydrocarbon group, and D is as defined above; or Formula (1-3)

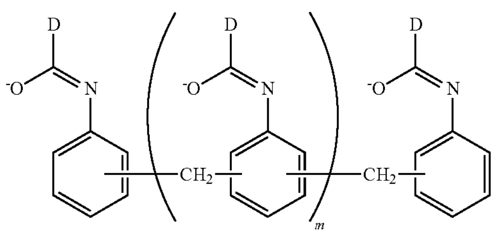

(1-3)

wherein m is an integer of 0 to 4, and D is as defined above.

[5] The amidate compound according to any one of [1] to [4], wherein the nitrogen-containing organic group represented by the formula (2) is a nitrogen-containing organic group represented by the following formula (2-1), (2-2), or (2-3):

Formula (2-1)

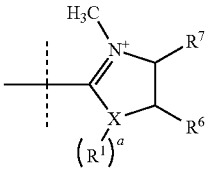

(2-1)

wherein $R^1$, X, and a are as defined above, and $R^6$ and $R^7$ are the same or different, and are each a hydrogen atom or a $C_1$-$C_6$ hydrocarbon group that may contain a heteroatom;

Formula (2-2)

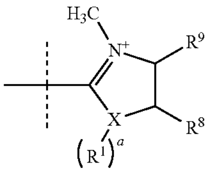

(2-2)

wherein $R^1$, X, and a are as defined above, and $R^8$ and $R^9$ are the same or different, and are each a hydrogen atom or a $C_1$-$C_6$ hydrocarbon group that may contain a heteroatom; or Formula (2-3)

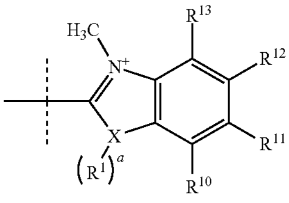

(2-3)

wherein $R^1$, X, and a are as defined above, and $R^{10}$, $R^{11}$, $R^{12}$, and $R^{13}$ are the same or different, and are each a hydrogen atom or a $C_1$-$C_6$ hydrocarbon group that may contain a heteroatom.

[6] The amidate compound according to any one of [1] to [5], wherein X is a nitrogen atom.

[7] The amidate compound according to [1], wherein the amidate compound is any one the following:

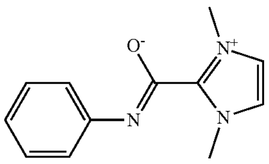

,

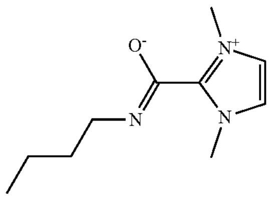

,

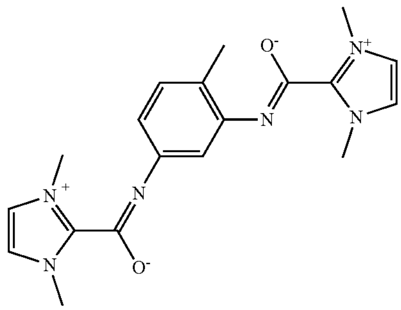

,

-continued
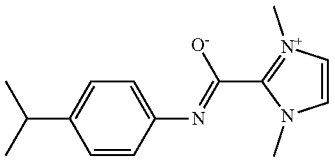,
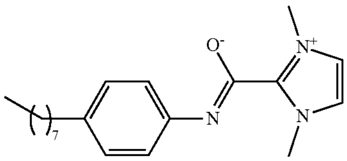,
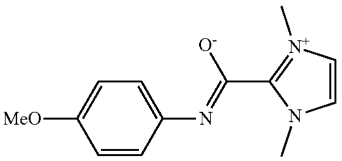,
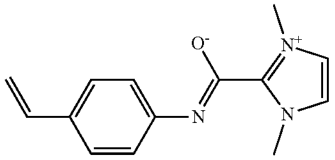,
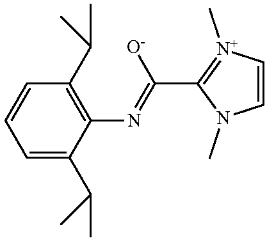,
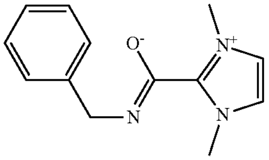,
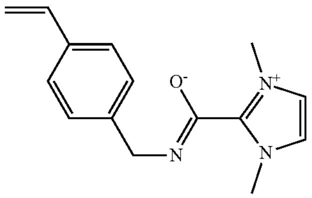,
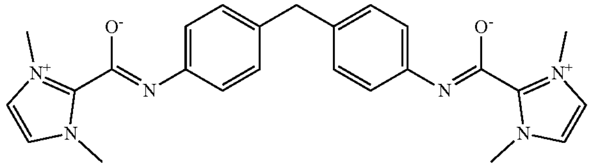,
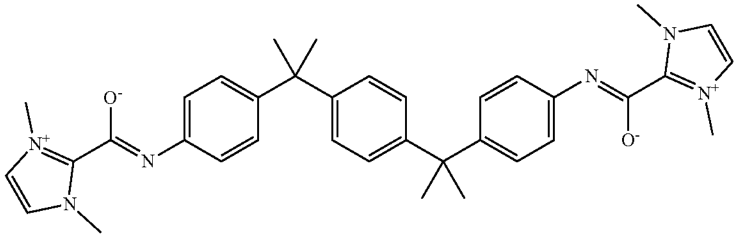,
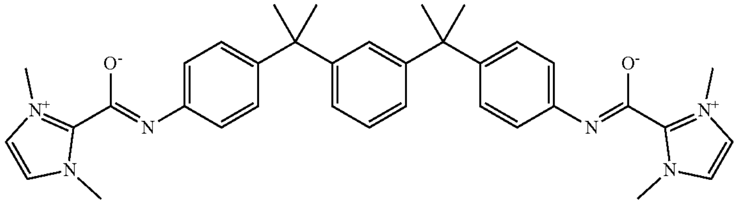,
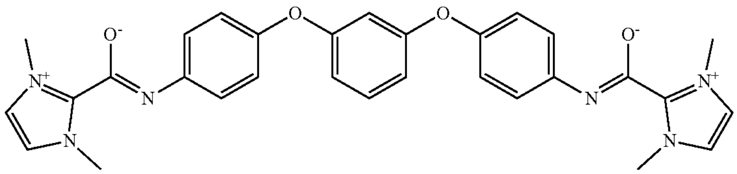,
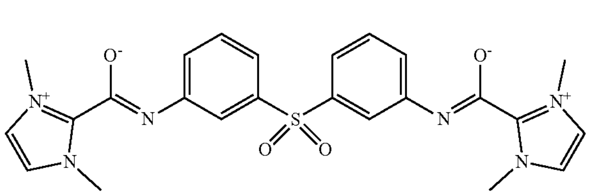,
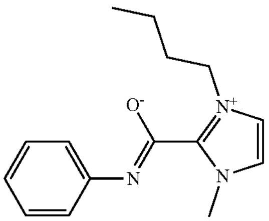, -continued

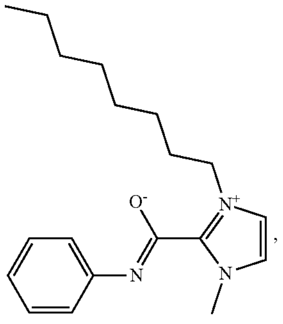

,

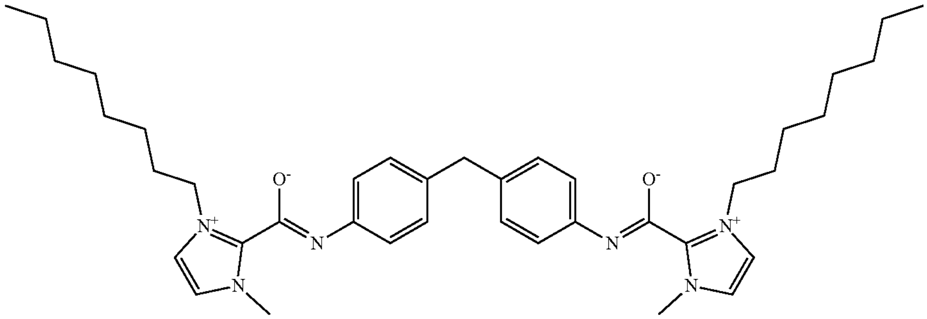 [SMILES: CCCCCCCC[n+]1ccn(C)c1/C([O-])=N/c1ccc(Cc2ccc(/N=C(\[O-])c3n(C)cc[n+]3CCCCCCCC)cc2)cc1]

[8] A catalyst for polyurethane production comprising an amidate compound represented by the formula (1):

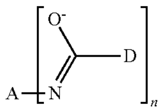

(1)

wherein A is a substituted or unsubstituted hydrocarbon group, n is an integer of 1 or more, and D is a nitrogen-containing organic group represented by the formula (2):

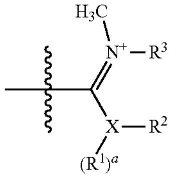

(2)

wherein $R^1$, $R^2$, and $R^3$ are the same or different, and are each a hydrocarbon group that may contain a heteroatom; some or all of $R^1$, $R^2$, and $R^3$ may be bonded together to form a ring structure; X is a nitrogen atom, an oxygen atom, or a sulfur atom; and a is 0 or 1, wherein a is 1 when X is a nitrogen atom, and a is 0 when X is an oxygen atom or a sulfur atom.

[9] The catalyst for polyurethane production according to [8], wherein A is an unsubstituted hydrocarbon group or a hydrocarbon group having at least one substituent selected from a halogen atom, an alkylamino group, a dialkylamino group, an alkoxy group, an aryloxy group, a halogenated alkyl group, a nitro group, a cyano group, a sulfonyl group, or an isocyanate group.

[10] The catalyst for polyurethane production according to [8] or [9], wherein n is an integer of 1 to 6.

[11] The catalyst for polyurethane production according to [8], wherein the amidate compound represented by the formula (1) is an amidate compound represented by the following formula (1-1), (1-2), or (1-3):

Formula (1-1):

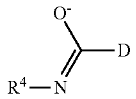

(1-1)

wherein $R^4$ is a substituted or unsubstituted hydrocarbon group, and D is as defined above;

Formula (1-2):

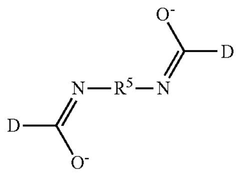

(1-2)

wherein $R^5$ is a substituted or unsubstituted hydrocarbon group, and D is as defined above; or Formula (1-3):

(1-3)

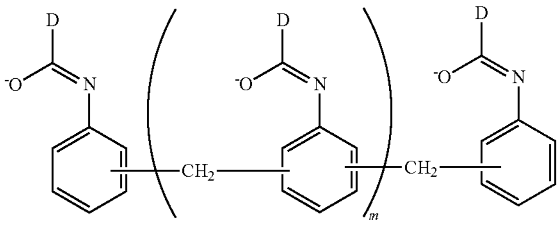

wherein m is an integer of 0 to 4, and D is as defined above.

[12] The catalyst for polyurethane production according to any one of [8] to [11], wherein the nitrogen-containing organic group represented by the formula (2) is a nitrogen-containing organic group represented by the following formula (2-1), (2-2), or (2-3):

Formula (2-1):

(2-1)

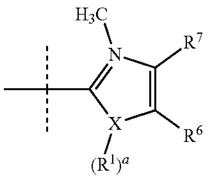

wherein $R^1$, X, and a are as defined above, $R^6$ and $R^7$ are the same or different, and are each a hydrogen atom or a $C_1$-$C_6$ hydrocarbon group that may contain a heteroatom;

Formula (2-2):

(2-2)

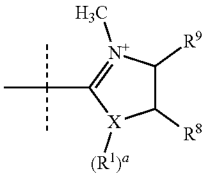

wherein $R^1$, X, and a are as defined above, and $R^8$ and $R^9$ are the same or different, and are each a hydrogen atom or a $C_1$-$C_6$ hydrocarbon group that may contain a heteroatom; or Formula (2-3):

(2-3)

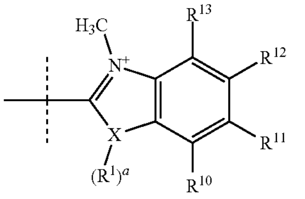

wherein $R^1$, X, and a are as defined above, and $R^{10}$, $R^{11}$, $R^{12}$, and $R^{13}$ are the same or different, and are each a hydrogen atom or a $C_1$-$C_6$ hydrocarbon group that may contain a heteroatom.

[13] The catalyst for polyurethane production according to any one of [8] to [12], wherein X is a nitrogen atom.

[14] The catalyst for polyurethane production according to [8], wherein the amidate compound is any one of the following:

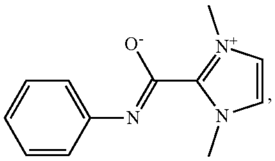,
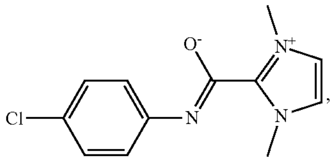,
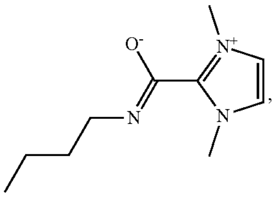,
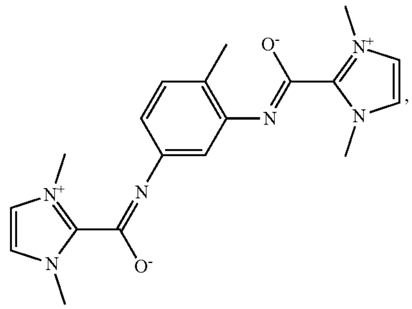,
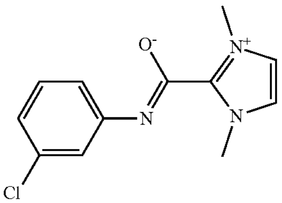,
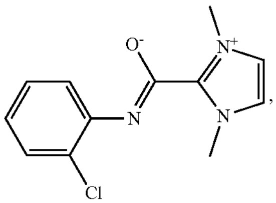,
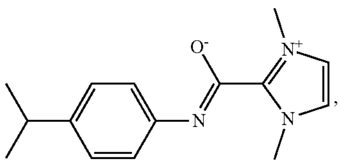,
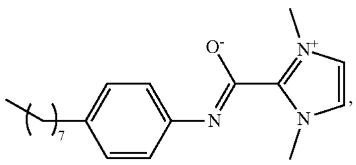,
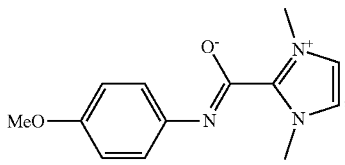, -continued
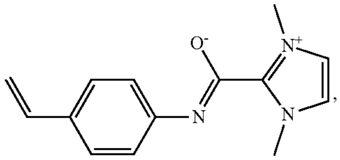,
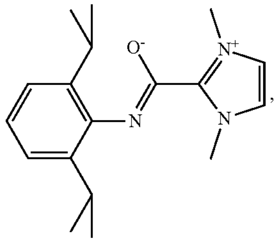,
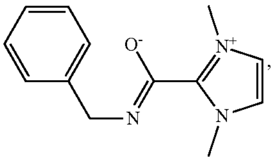,
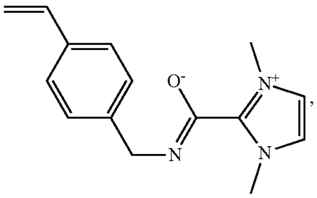,
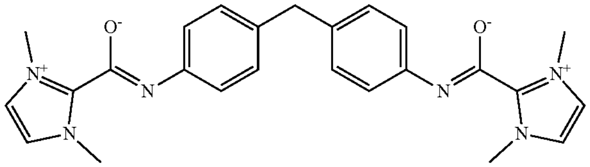,
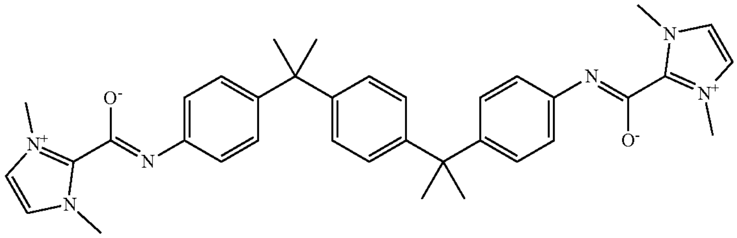,
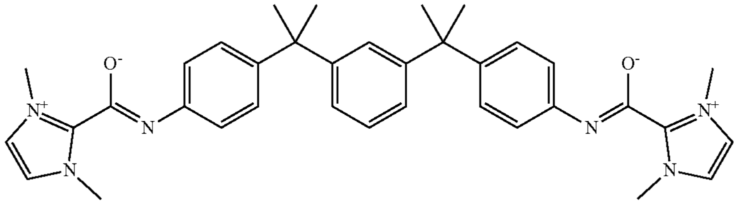,
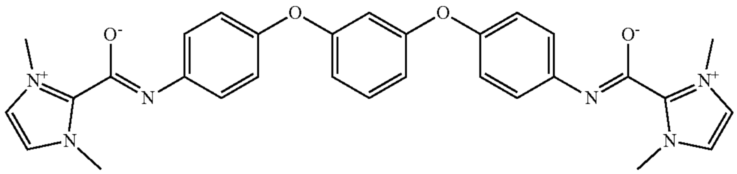,
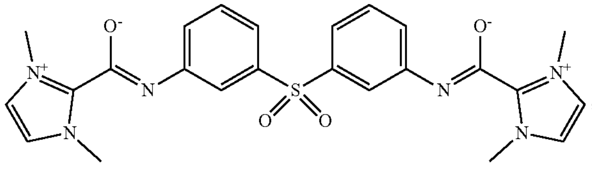,
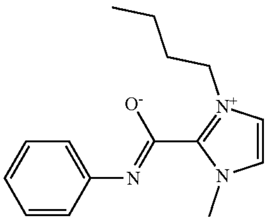,
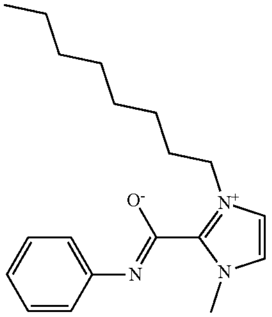, -continued

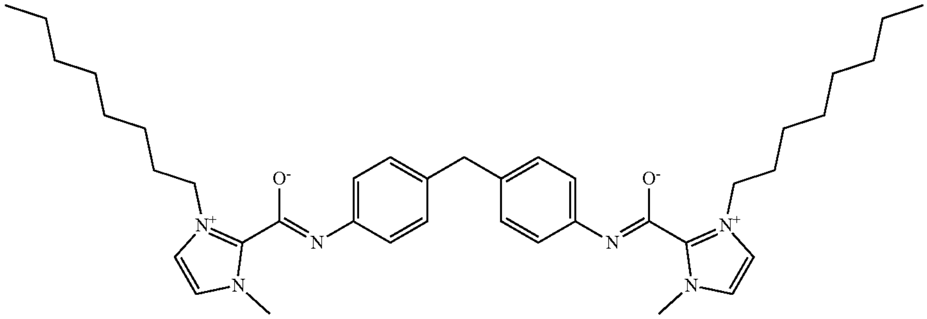

[15] A method for producing a polyurethane resin, the method comprising reacting a polyol and a polyisocyanate in the presence of the catalyst for polyurethane production according to any one of [8] to [14].

[16] A method for producing the amidate compound according to any one of [1] to [7], the method comprising the following steps 1 and 2:

step 1 of reacting a nitrogen-containing organic compound represented by the following formula (3) and dimethyl carbonate to produce a carboxylate compound represented by the following formula (4):

Formula (3):

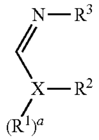

(3)

wherein $R^1$, $R^2$, $R^3$, X, and a are as defined above;

Formula (4):

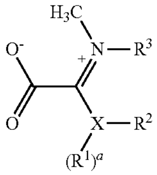

(4)

wherein $R^1$, $R^2$, $R^3$, X, and a are as defined above; and step 2 of reacting the carboxylate compound represented by the formula (4) and an isocyanate compound represented by the following formula (5):

Formula (5):

$$A{+}NCO]_n \quad (5)$$

wherein A and n are as defined above.

[17] The production method according to [16], wherein in step 2, the reaction is performed in the presence of a hydrocarbon solvent.

[18] The production method according to [17], wherein the hydrocarbon solvent is an aromatic hydrocarbon solvent or a halogenated aromatic hydrocarbon solvent.

[19] The production method according to [18], wherein the aromatic hydrocarbon solvent or the halogenated aromatic hydrocarbon solvent is selected from the group consisting of toluene, xylene, and chlorobenzene.

Advantageous Effects of Invention

The present invention can provide a catalyst for polyurethane production that does not produce $CO_2$ gas when used as a catalyst for polyurethane production, and that is easy to handle and produce.

DESCRIPTION OF EMBODIMENTS

Embodiments for carrying out the present invention are described in detail below.

In the formula (1), A is a substituted or unsubstituted hydrocarbon group, preferably a substituted or unsubstituted $C_1$-$C_{100}$ hydrocarbon group, more preferably a substituted or unsubstituted $C_1$-$C_{50}$ hydrocarbon group, and particularly preferably a substituted or unsubstituted $C_1$-$C_{30}$ hydrocarbon group.

When A is substituted, examples of substituents include halogen atoms, such as fluorine, chlorine, bromine, and iodine; alkylamino groups, such as methylamino; dialkylamino groups, such as dimethylamino; alkoxy groups, such as methoxy and ethoxy; aryloxy groups, such as benzyloxy; halogenated alkyl groups, such as trifluormethyl; nitro groups, cyano groups, sulfonyl groups, isocyanate groups, and the like. Moreover, the hydrocarbon group A may be substituted with a heteroatom, such as oxygen, nitrogen, or sulfur. When the hydrocarbon group A is substituted with a heteroatom, such as oxygen, nitrogen, or sulfur, the hydrocarbon group has a group, such as —O—, —NH—, or —S—, and the hydrocarbon chain is interrupted by such a group.

Examples of the alkyl moiety of the above alkylamino groups, dialkylamino groups, alkoxy groups, and halogenated alkyl groups include linear or branched $C_1$-$C_6$ alkyl groups, such as methyl, ethyl, n-propyl, isopropyl, n-butyl, isobutyl, sec-butyl, tert-butyl, and pentyl. The number of carbon atoms in the alkyl group is preferably 1 to 3, and more preferably 1 or 2.

Examples of the above aryl groups include $C_6$-$C_{10}$ aryl groups. Specific examples include a phenyl group, a naphthyl group, and the like.

The number of substituents is 1 to 5, preferably 1 to 3, and more preferably 1 or 2.

In one embodiment of the present invention, when A is substituted, the substituent does not include a chlorine atom. In another embodiment of the present invention, the substituent is at least one member selected from a fluorine atom, an alkylamino group, a dialkylamino group, an alkoxy group, an aryloxy group, a nitro group, a cyano group, a sulfonyl group, or an isocyanate group.

n is an integer of 1 or more, preferably 1 to 6, more preferably 1 to 4, and particularly preferably 1 or 2.

D is a nitrogen-containing organic group represented by the formula (2).

In the present invention, the amidate compound represented by the formula (1) (hereinafter referred to as "the amidate compound (1)") is preferably an amidate compound represented by the formula (1-1), (1-2), or (1-3); and particularly preferably an amidate compound represented by the formula (1-1) or (1-2).

In the formula (1-1), $R^4$ is a substituted or unsubstituted hydrocarbon group, preferably a substituted or unsubstituted $C_1$-$C_{50}$ hydrocarbon group, more preferably a substituted or unsubstituted $C_1$-$C_{30}$ hydrocarbon group, even more preferably a substituted or unsubstituted $C_1$-$C_{14}$ hydrocarbon group, and particularly preferably a substituted or unsubstituted $C_1$-$C_{12}$ hydrocarbon group. Specific examples include a methyl group, an ethyl group, a n-propyl group, an isopropyl group, a n-butyl group, a s-butyl group, a t-butyl group, a n-pentyl group, a n-hexyl group, a n-heptyl group, a n-decyl group, a n-dodecyl group, a n-octadecyl group, a cyclopropyl group, a cyclopentyl group, a cyclohexyl group, a phenyl group, a naphthyl group, a benzyl group, a phenethyl group, a tolyl group, an allyl group, and the like; and preferably a benzyl group and a phenyl group.

When $R^4$ is substituted, examples of substituents include halogen atoms, such as fluorine, chlorine, bromine, and iodine; alkylamino groups, such as methylamino; dialkylamino groups, such as dimethylamino; alkoxy groups, such as methoxy and ethoxy; aryloxy groups, such as benzyloxy; halogenated alkyl groups, such as trifluoromethyl; nitro groups, cyano groups, isocyanate groups, and the like. Moreover, the hydrocarbon group $R^4$ may be substituted with a heteroatom, such as oxygen, nitrogen, or sulfur. When the hydrocarbon group is substituted with a heteroatom, such as oxygen, nitrogen, or sulfur, the hydrocarbon group has a group, such as —O—, —NH—, or —S—, and the hydrocarbon chain is interrupted by such a group.

Examples of the alkyl moiety of the above alkylamino groups, dialkylamino groups, alkoxy groups, and halogenated alkyl groups include linear or branched $C_1$-$C_6$ alkyl groups, such as methyl, ethyl, n-propyl, isopropyl, n-butyl, isobutyl, sec-butyl, tert-butyl, and pentyl. The number of carbon atoms in the alkyl group is preferably 1 to 3, and more preferably 1 or 2.

Examples of the above aryl groups include $C_6$-$C_{10}$ aryl groups. Specific examples include a phenyl group, a naphthyl group, and the like.

The number of substituents is 1 to 5, preferably 1 to 3, and more preferably 1 or 2.

D is as defined above.

In the formula (1-2), $R^5$ is a substituted or unsubstituted hydrocarbon group, more preferably a substituted or unsubstituted $C_1$-$C_{100}$ hydrocarbon group, more preferably a substituted or unsubstituted $C_1$-$C_{50}$ hydrocarbon group, and particularly preferably a substituted or unsubstituted $C_1$-$C_{30}$ hydrocarbon group. Specific examples include alkylene groups, such as a methylene group, a dimethylmethylene group, an ethylene group, a n-propylene group, a n-butylene group, a n-pentylene group, a n-hexylene group, a n-heptylene group, a n-octylene group, a n-nonylene group, a n-decylene group, a n-dodecylene group, a n-octadecylene group, and a cyclohexylene group; allylene groups, such as a phenylene group, a 2-methylphenylene group, a 2,6-dimethylphenylene group, a 2,4-dimethylphenylene group, a 2,3-dimethylphenylene group, and a naphthylene group; arylalkylene groups, such as a phenylmethylene group, a phenylethylene group, a 1-phenylpropylene group, a 2-phenylpropylene group, a 1-phenylbutylene group, 2-phenylbutylene group, a naphthylmethylene group, and a naphthylethylene group; arylenealkylene groups obtained by suitably combining the above alkylene groups and allylene groups; and the like. These divalent hydrocarbon groups may be repeated or combined to constitute one divalent hydrocarbon group.

When $R^5$ is substituted, examples of substituents include halogen atoms, such as fluorine, chlorine, bromine, and iodine; alkylamino groups, such as methylamino; dialkylamino groups, such as dimethylamino; alkoxy groups, such as methoxy and ethoxy; aryloxy groups, such as benzyloxy; halogenated alkyl groups, such as trifluoromethyl; nitro groups, cyano groups, isocyanate groups, and the like. Moreover, the hydrocarbon group $R^5$ may be substituted with a heteroatom, such as oxygen, nitrogen, or sulfur. When the hydrocarbon group is substituted with a heteroatom, such as oxygen, nitrogen, or sulfur, the hydrocarbon group has a group, such as —O—, —NH—, or —S—, and the hydrocarbon chain is interrupted by such a group.

Examples of the alkyl moiety of the above alkylamino groups, dialkylamino groups, alkoxy groups, and halogenated alkyl groups include linear or branched $C_1$-$C_6$ alkyl groups, such as methyl, ethyl, n-propyl, isopropyl, n-butyl, isobutyl, sec-butyl, tert-butyl, and pentyl. The number of carbon atoms in the alkyl group is preferably 1 to 3, and more preferably 1 or 2.

Examples of the above aryl groups include $C_6$-$C_{10}$ aryl groups. Specific examples include a phenyl group, a naphthyl group, and the like.

The number of substituents is 1 to 5, preferably 1 to 3, and more preferably 1 or 2.

D is as defined above.

In the formula (1-3), m is an integer of 0 to 4, and D is as defined above.

In the formula (2), $R^1$, $R^2$, and $R^3$ are hydrocarbon groups that may contain a heteroatom. Some or all of $R^1$, $R^2$, and $R^3$ may be bonded together to form a ring structure. For example, $R^1$ and $R^2$, $R^1$ and $R^3$, $R^2$ and $R^3$, or $R^1$, $R^2$, and $R^3$, may be bonded together to form a ring structure. Examples of the hydrocarbon group that may contain a heteroatom include a methyl group, an ethyl group, a n-propyl group, an isopropyl group, a n-butyl group, a s-butyl group, a t-butyl group, a n-pentyl group, a n-hexyl group, a n-octyl group, a n-decyl group, a n-dodecyl group, an allyl group, a benzyl group, a cyclohexyl group, an adamantyl group, a phenyl group, a 2,6-diisopropylphenyl group, a 2,4,6-trimethylphenyl group, a 2-methoxyethyl group, a 2-ethoxyethyl group, 2-(dimethylamino)ethyl group, and the like; preferably a methyl group, an ethyl group, a n-propyl group, an isopropyl group, a t-butyl group, a n-octyl group, a cyclopentyl group, a cyclohexyl group, and a 2,4,6-trimethyl phenyl group; more preferably a methyl group, an ethyl group, an isopropyl group, a t-butyl group, a n-octyl group, and a phenyl group; and particularly preferably a methyl group, an isopropyl group, a t-butyl group, a n-octyl group, and a phenyl group. X is a nitrogen atom, an oxygen atom, or a sulfur atom; and preferably a nitrogen atom.

In the formula (2), a is 0 or 1. a is 1 when X is a nitrogen atom, and a is 0 when X is an oxygen atom or a sulfur atom. That is, the formula (2) represents a nitrogen-containing organic group represented by the following formula (2a), (2b), or (2c). In other words, $R^1$ does not exist when X is an oxygen atom or a sulfur atom.

(2a)

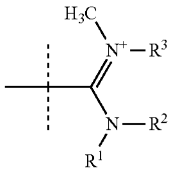

(2b)

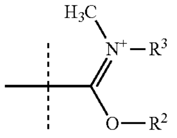

(2c)

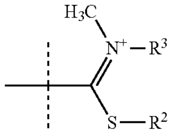

In the present invention, $R^2$ and $R^3$ of the nitrogen-containing organic group represented by the formula (2) are preferably bonded together to form a ring structure. The nitrogen-containing organic group represented by the formula (2) wherein a ring is formed is preferably a nitrogen-containing organic group represented by the formula (2-1), (2-2), or (2-3); and particularly preferably a nitrogen-containing organic group represented by the formula (2-1).

In the formula (2-1), $R^1$, X, and a are as defined above. $R^6$ and $R^7$ are hydrogen atoms or $C_1$-$C_6$ hydrocarbon groups that may contain a heteroatom, and preferably hydrogen atoms. Examples of the $C_1$-$C_6$ hydrocarbon group that may contain a heteroatom include a methyl group, an ethyl group, a n-propyl group, an isopropyl group, a n-butyl group, a s-butyl group, a t-butyl group, a pentyl group, a hexyl group, a cyclohexyl group, a phenyl group, a 2-methoxyethyl group, a 2-ethoxyethyl group, a 2-(dimethylamino)ethyl group, and the like; and preferably a methyl group.

Specific examples include a 1,3-dimethylimidazolium group, a 1-ethyl-3-methylimidazolium group, a 1-methyl-3-propylimidazolium group, a 1-methyl-3-isopropylimidazolium group, a 1-n-butyl-3-methylimidazolium group, a 1-tert-butyl-3-methylimidazolium group, a 1-methyl-3-pentylimidazolium group, a 1-hexyl-3-methylimidazolium group, a 1-heptyl-3-methylimidazolium group, a 1-methyl-3-octylimidazolium group, a 1-methyl-3-nonylimidazolium group, a 1-decyl-3-methylimidazolium group, a 1-allyl-3-methylimidazolium group, a 1-benzyl-3-methylimidazolium group, a 1-(2-methoxyethyl)-3-methylimidazolium group, a 1-(2-ethoxyethyl)-3-methylimidazolium group, a 1-(2-dimethylaminoethyl)-3-methylimidazolium group, a 1,3,4,5-tetramethylimidazolium group, a 3-methyloxazolium group, a 3,5-dimethyloxazolium group, a 3,4,5-trimethyloxazolium group, a 3-methylthiazolium group, a 3,4-dimethylthiazolium group, a 3,5-dimethylthiazolium group, a 3,4,5-trimethylthiazolium group, and the like; preferably a 1,3-dimethylimidazolium group, a 1-ethyl-3-methylimidazolium group, a 1-methyl-3-propylimidazolium group, a 1-butyl-3-methylimidazolium group, and a 1-methyl-3-octylimidazolium group; and particularly preferably a 1,3-dimethylimidazolium group, a 1-butyl-3-methylimidazolium group, and a 1-methyl-3-octylimidazolium group.

In the present specification, the terms propyl, butyl, pentyl, hexyl, heptyl, octyl, nonyl, decyl, etc., refer to linear alkyl groups, such as n-propyl, n-butyl, n-pentyl, n-hexyl, n-heptyl, n-octyl, n-nonyl, and n-decyl, respectively, unless otherwise specified.

In the formula (2-2), $R^1$, X, and a are as defined above. $R^8$ and $R^9$ are hydrogen atoms or $C_1$-$C_6$ hydrocarbon groups that may contain a heteroatom, and preferably hydrogen atoms. Examples of the $C_1$-$C_6$ hydrocarbon group that may contain a heteroatom include a methyl group, an ethyl group, a n-propyl group, an isopropyl group, a n-butyl group, a s-butyl group, a t-butyl group, a n-pentyl group, a n-hexyl group, a cyclohexyl group, a phenyl group, a 2-methoxyethyl group, a 2-ethoxyethyl group, a 2-(dimethylamino)ethyl group, and the like; and preferably a methyl group.

Specific examples include a 1,3-dimethylimidazolinium group, a 1-ethyl-3-methylimidazolinium group, a 1-methyl-3-propylimidazolinium group, a 1-butyl-3-methylimidazolinium group, a 1-methyl-3-pentylimidazolinium group, a 1-hexyl-3-methylimidazolinium group, a 1-heptyl-3-methylimidazolinium group, a 1-methyl-3-octylimidazolinium group, a 1-methyl-3-nonylimidazolinium group, a 1-decyl-3-methylimidazolinium group, a 1-allyl-3-methylimidazolinium group, a 1-benzyl-3-methylimidazolinium group, a 1-(2-methoxyethyl)-3-methylimidazolinium group, a 1-(2-ethoxyethyl)-3-methylimidazolinium group, a 1-(2-dimethylaminoethyl)-3-methylimidazolinium group, a 1,3,4,5-tetramethylimidazolinium group, a 3-methyloxazolinium group, a 3,4-dimethyloxazolinium group, a 3,5-dimethyloxazolinium group, a 3,4,5-trimethyloxazolinium group, a 3-methylthiazolinium group, a 3,4-dimethylthiazolinium group, a 3,5-dimethylthiazolinium group, a 3,4,5-trimethylthiazolinium group, and the like; preferably a 1,3-dimethylimidazolinium group, a 1-ethyl-3-methylimidazolinium group, a 1-methyl-3-propylimidazolinium group, a 1-butyl-3-methylimidazolinium group, and a 1-methyl-3-octylimidazolinium group; and particularly preferably a 1,3-dimethylimidazolinium group, a 1-butyl-3-methylimidazolinium group, and a 1-methyl-3-octylimidazolinium group.

In the formula (2-3), $R^1$, X, and a are as defined above. $R^{10}$, $R^{11}$, $R^{12}$, and $R^{13}$ are hydrogen atoms or $C_1$-$C_6$ hydrocarbon groups that may contain a heteroatom, and preferably hydrogen atoms. Examples of the $C_1$-$C_6$ hydrocarbon group that may contain a heteroatom include a methyl group, an ethyl group, a n-propyl group, an isopropyl group, a n-butyl group, a s-butyl group, a t-butyl group, a n-pentyl group, a n-hexyl group, a cyclohexyl group, a phenyl group, a 2-methoxyethyl group, a 2-ethoxyethyl group, a 2-(dimethylamino)ethyl group, and the like; and preferably a methyl group.

Specific examples include a 1,3-dimethylbenzimidazolium group, a 1-ethyl-3-methylbenzimidazolium group, a 1-methyl-3-propylbenzimidazolium group, a 1-butyl-3-methylbenzimidazolium group, a 1-methyl-3-pentylbenzimidazolium group, a 1-hexyl-3-methylbenzimidazolium group, a 1-heptyl-3-methylbenzimidazolium group, a 1-methyl-3-octylbenzimidazolium group, a 1-methyl-3-nonylbenzimidazolium group, a 1-decyl-3-methylbenzimidazolium group, a 1-allyl-3-methylbenzimidazolium group, a 1-benzyl-3-methylbenzimidazolium group, a 1,3,6-trimethylbenzimidazolium group, a 1-acetyl-3,6-dimethylbenzimidazolium group, a 1,3,6,7-tetramethylbenzimidazolium group, a 1,3-dibenzyl-6,7-dimethylbenzimidazolium group, a 3-methylbenzoxazolium group, a 3-methylbenzothiazolium group, and the like; preferably a 1,3-dimethylbenzimidazolium group, a 1-ethyl-3-methylbenzimidazolium group, a 1-methyl-3-propylbenzimidazolium group, and a 1-butyl-3-methylbenzimidazolium group; and particularly preferably a 1,3-dimethylbenzimidazolium group.

Although specific examples of the amidate compound (1) are shown below, the present invention is not limited thereto. In the following specific examples, Et represents an ethyl group, Pr represents a n-propyl group, and Bu represents a n-butyl group.

(1-1-1a)

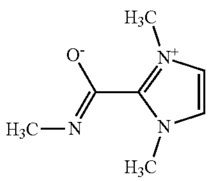

(1-1-2a)

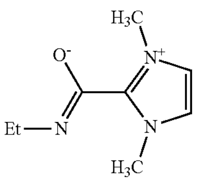

(1-1-3a)

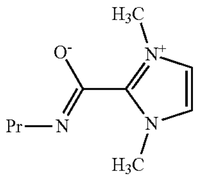

(1-1-4a)

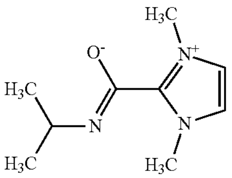

(1-1-5a)

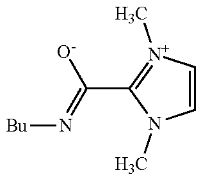

(1-1-6a)

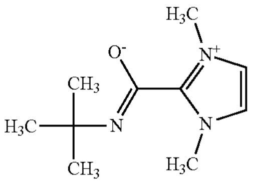

(1-1-7a)

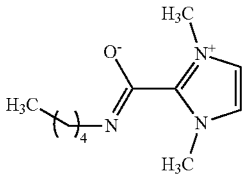

(1-1-8a)

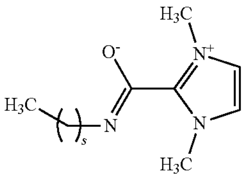

(1-1-9a)

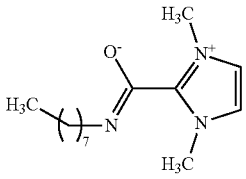

(1-1-10a)

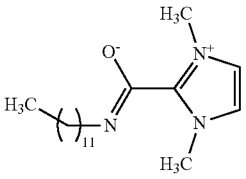

(1-1-11a)

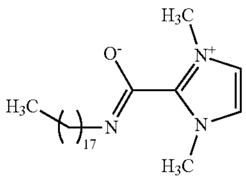

(1-1-12a)

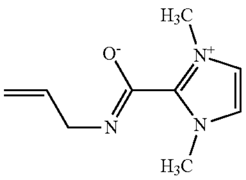

(1-1-13a)

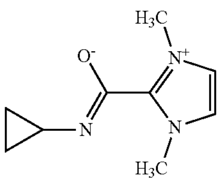

(1-1-14a)

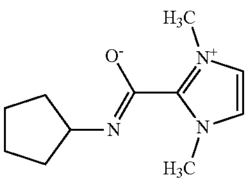

-continued
(1-1-15a)
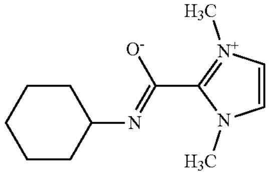
(1-1-16a)
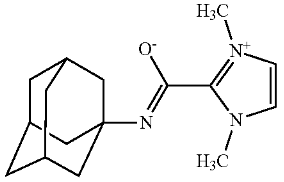
(1-1-17a)
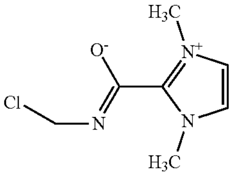
(1-1-18a)
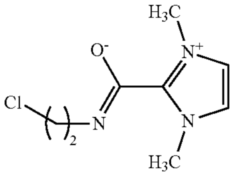
(1-1-19a)
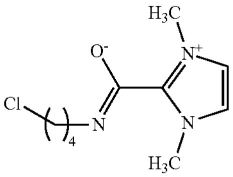
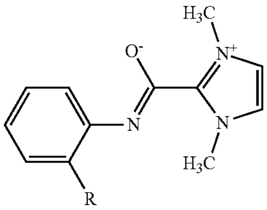
| | |
|---|---|
| R = H | (1-1-20a) |
| $CH_3$ | (1-1-21a) |
| $(CH_2)_3CH_3$ | (1-1-22a) |
| $(CH_2)_7CH_3$ | (1-1-23a) |
| $OCH_3$ | (1-1-24a) |
| $OCH_2CH_3$ | (1-1-25a) |
| $CH(CH_3)_2$ | (1-1-26a) |
| $C(CH_3)_3$ | (1-1-27a) |
| $N(CH_3)_2$ | (1-1-28a) |
| F | (1-1-29a) |
| Cl | (1-1-30a) |
| Br | (1-1-31a) |
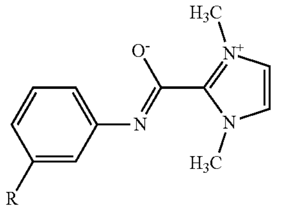
| | |
|---|---|
| R = $CH_3$ | (1-1-32a) |
| $(CH_2)_3CH_3$ | (1-1-33a) |
| $(CH_2)_7CH_3$ | (1-1-34a) |
| $OCH_3$ | (1-1-35a) |
| $OCH_2CH_3$ | (1-1-36a) |
| $CH(CH_3)_2$ | (1-1-37a) |
| $C(CH_3)_3$ | (1-1-38a) |
| $N(CH_3)_2$ | (1-1-39a) |
| F | (1-1-40a) |
| Cl | (1-1-41a) |
| Br | (1-1-42a) |
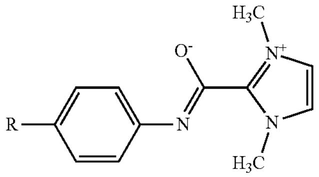
| | |
|---|---|
| R = $CH_3$ | (1-1-43a) |
| $(CH_2)_3CH_3$ | (1-1-44a) |
| $(CH_2)_7CH_3$ | (1-1-45a) |
| $OCH_3$ | (1-1-46a) |
| $OCH_2CH_3$ | (1-1-47a) |
| $CH(CH_3)_2$ | (1-1-48a) |
| $C(CH_3)_3$ | (1-1-49a) |
| $N(CH_3)_2$ | (1-1-50a) |
| F | (1-1-51a) |
| Cl | (1-1-52a) |
| Br | (1-1-53a) |
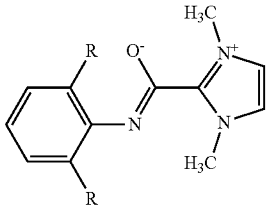
| | |
|---|---|
| R = $CH_3$ | (1-1-54a) |
| $(CH_2)_3CH_3$ | (1-1-55a) |
| $(CH_2)_7CH_3$ | (1-1-56a) |
| $OCH_3$ | (1-1-57a) |
| $OCH_2CH_3$ | (1-1-58a) |
| $CH(CH_3)_2$ | (1-1-59a) |
| $C(CH_3)_3$ | (1-1-60a) |
| $N(CH_3)_2$ | (1-1-61a) |
| F | (1-1-62a) |
| Cl | (1-1-63a) |
| Br | (1-1-64a) |

-continued
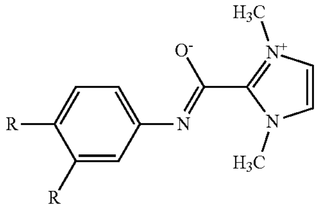
| | |
|---|---|
| R = $CH_3$ | (1-1-65a) |
| $(CH_2)_3CH_3$ | (1-1-66a) |
| $(CH_2)_7CH_3$ | (1-1-67a) |
| $OCH_3$ | (1-1-68a) |
| $OCH_2CH_3$ | (1-1-69a) |
| $CH(CH_3)_2$ | (1-1-70a) |
| $C(CH_3)_3$ | (1-1-71a) |
| $N(CH_3)_2$ | (1-1-72a) |
| F | (1-1-73a) |
| Cl | (1-1-74a) |
| Br | (1-1-75a) |
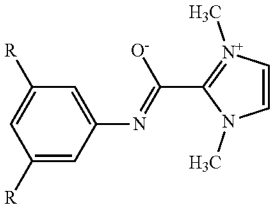
| | |
|---|---|
| R = $CH_3$ | (1-1-76a) |
| $(CH_2)_3CH_3$ | (1-1-77a) |
| $(CH_2)_7CH_3$ | (1-1-78a) |
| $OCH_3$ | (1-1-79a) |
| $OCH_2CH_3$ | (1-1-80a) |
| $CH(CH_3)_2$ | (1-1-81a) |
| $C(CH_3)_3$ | (1-1-82a) |
| $N(CH_3)_2$ | (1-1-83a) |
| F | (1-1-84a) |
| Cl | (1-1-85a) |
| Br | (1-1-86a) |
(1-1-87a)
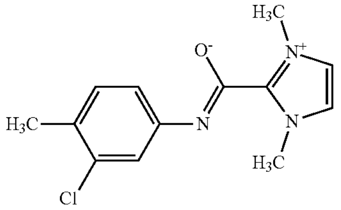
(1-1-88a)
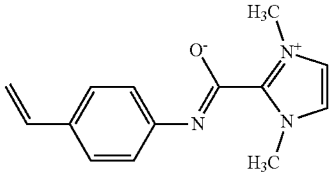
(1-1-89a)
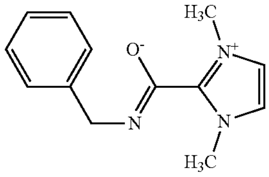
(1-1-90a)
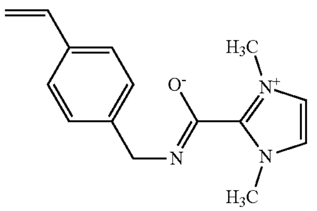
(1-1-1b)
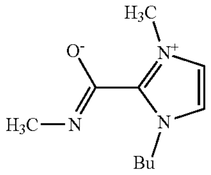
(1-1-2b)
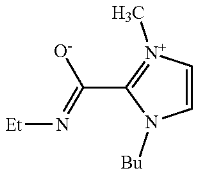
(1-1-3b)
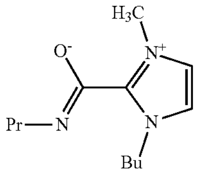
(1-1-4b
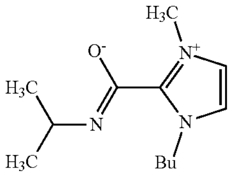
(1-1-5b)
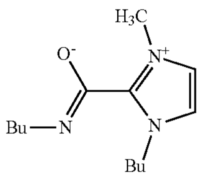
(1-1-6b)
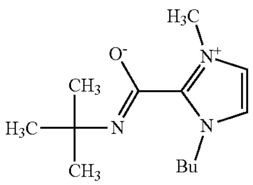

-continued
(1-1-7b)
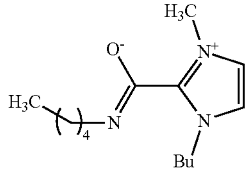
(1-1-8b)
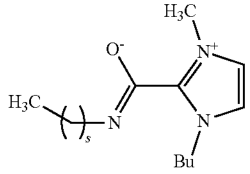
(1-1-9b)
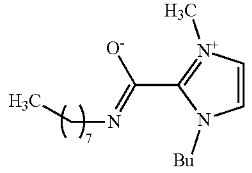
(1-1-10b)
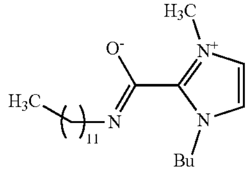
(1-1-11b)
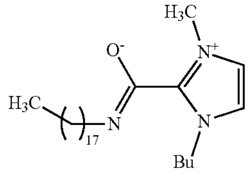
(1-1-12b)
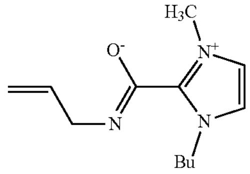
(1-1-13b)
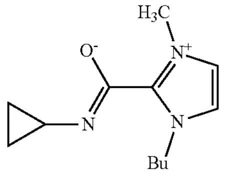
(1-1-14b)
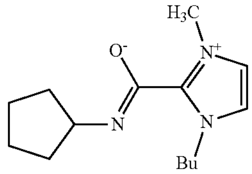
(1-1-15b)
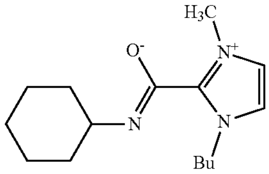
(1-1-16b)
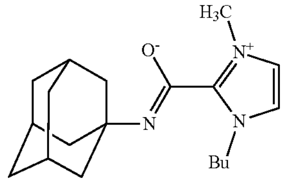
(1-1-17b)
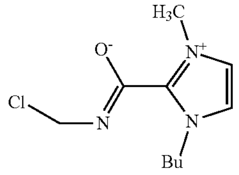
(1-1-18b)
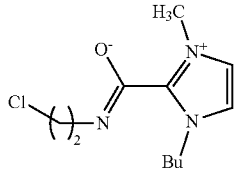
(1-1-19b)
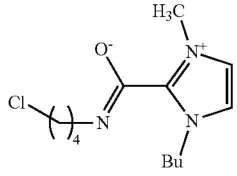
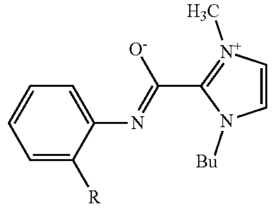
| | |
|---|---|
| R = H | (1-1-20b) |
| $CH_3$ | (1-1-21b) |
| $(CH_2)_3CH_3$ | (1-1-22b) |
| $(CH_2)_7CH_3$ | (1-1-23b) |
| $OCH_3$ | (1-1-24b) |
| $OCH_2CH_3$ | (1-1-25b) |
| $CH(CH_3)_2$ | (1-1-26b) |
| $C(CH_3)_3$ | (1-1-27b) |
| $N(CH_3)_2$ | (1-1-28b) |
| F | (1-1-29b) |
| Cl | (1-1-30b) |
| Br | (1-1-31b) |

-continued

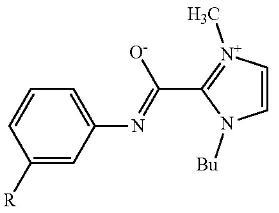

| | |
|---|---|
| R = $CH_3$ | (1-1-32b) |
| $(CH_2)_3CH_3$ | (1-1-33b) |
| $(CH_2)_7CH_3$ | (1-1-34b) |
| $OCH_3$ | (1-1-35b) |
| $OCH_2CH_3$ | (1-1-36b) |
| $CH(CH_3)_2$ | (1-1-37b) |
| $C(CH_3)_3$ | (1-1-38b) |
| $N(CH_3)_2$ | (1-1-39b) |
| F | (1-1-40b) |
| Cl | (1-1-41b) |
| Br | (1-1-42b) |

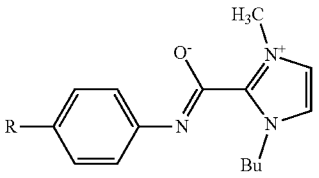

| | |
|---|---|
| R = $CH_3$ | (1-1-43b) |
| $(CH_2)_3CH_3$ | (1-1-44b) |
| $(CH_2)_7CH_3$ | (1-1-45b) |
| $OCH_3$ | (1-1-46b) |
| $OCH_2CH_3$ | (1-1-47b) |
| $CH(CH_3)_2$ | (1-1-48b) |
| $C(CH_3)_3$ | (1-1-49b) |
| $N(CH_3)_2$ | (1-1-50b) |
| F | (1-1-51b) |
| Cl | (1-1-52b) |
| Br | (1-1-53b) |

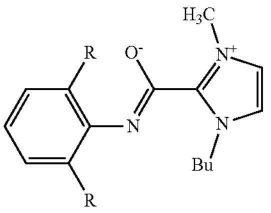

| | |
|---|---|
| R = $CH_3$ | (1-1-54b) |
| $(CH_2)_3CH_3$ | (1-1-55b) |
| $(CH_2)_7CH_3$ | (1-1-56b) |
| $OCH_3$ | (1-1-57b) |
| $OCH_2CH_3$ | (1-1-58b) |
| $CH(CH_3)_2$ | (1-1-59b) |
| $C(CH_3)_3$ | (1-1-60b) |
| $N(CH_3)_2$ | (1-1-61b) |
| F | (1-1-62b) |
| Cl | (1-1-63b) |
| Br | (1-1-64b) |

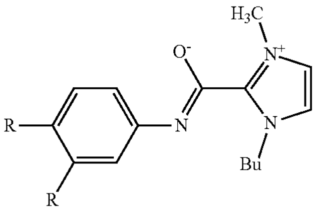

| | |
|---|---|
| R = $CH_3$ | (1-1-65b) |
| $(CH_2)_3CH_3$ | (1-1-66b) |
| $(CH_2)_7CH_3$ | (1-1-67b) |
| $OCH_3$ | (1-1-68b) |
| $OCH_2CH_3$ | (1-1-69b) |
| $CH(CH_3)_2$ | (1-1-70b) |
| $C(CH_3)_3$ | (1-1-71b) |
| $N(CH_3)_2$ | (1-1-72b) |
| F | (1-1-73b) |
| Cl | (1-1-74b) |
| Br | (1-1-75b) |

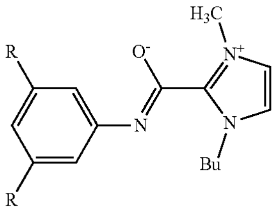

| | |
|---|---|
| R = $CH_3$ | (1-1-76b) |
| $(CH_2)_3CH_3$ | (1-1-77b) |
| $(CH_2)_7CH_3$ | (1-1-78b) |
| $OCH_3$ | (1-1-79b) |
| $OCH_2CH_3$ | (1-1-80b) |
| $CH(CH_3)_2$ | (1-1-81b) |
| $C(CH_3)_3$ | (1-1-82b) |
| $N(CH_3)_2$ | (1-1-83b) |
| F | (1-1-84b) |
| Cl | (1-1-85b) |
| Br | (1-1-86b) |

(1-1-87b)

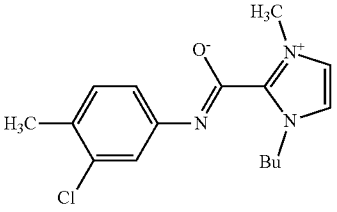

(1-1-88b)

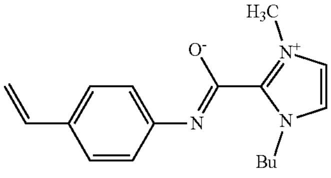

(1-1-89b)

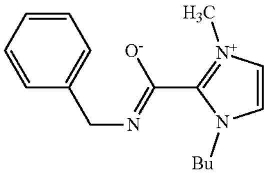

(1-1-90b)

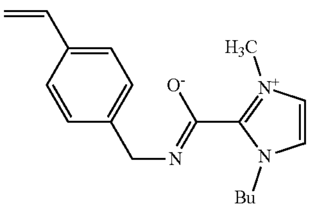

(1-1-1c)

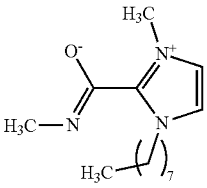

(1-1-2c)

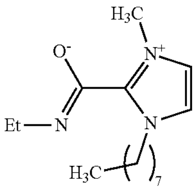

-continued
(1-1-3c)
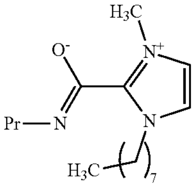
(1-1-4c)
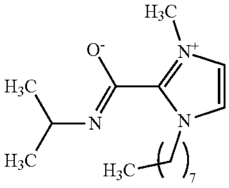
(1-1-5c)
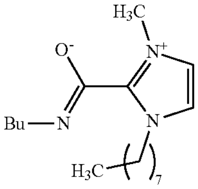
(1-1-6c)
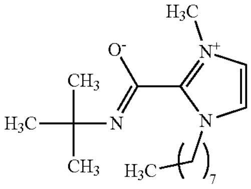
(1-1-7c)
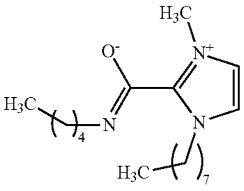
(1-1-8c)
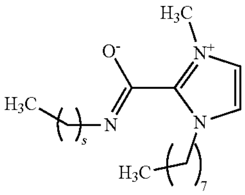
(1-1-9c)
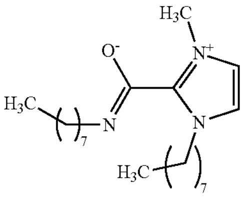
(1-1-10c)
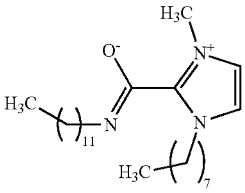
(1-1-11c)
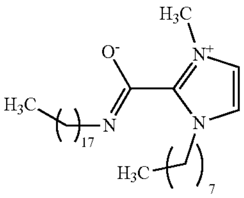
(1-1-12c)
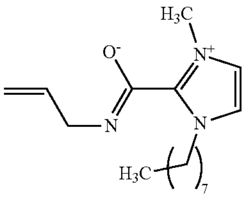
(1-1-13c)
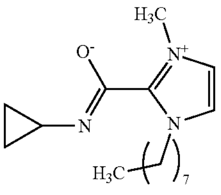
(1-1-14c)
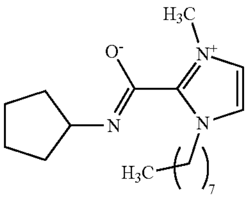
(1-1-15c)
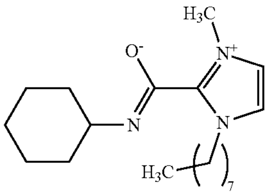
(1-1-16c)
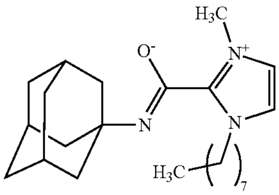
(1-1-17c)
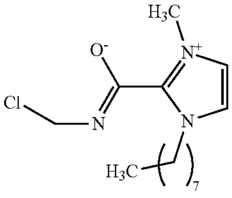
(1-1-18c)
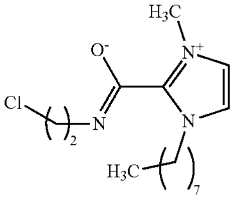

-continued (1-1-19c)

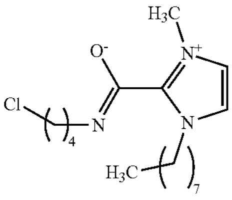

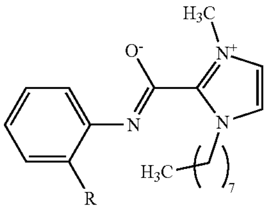

| | |
|---|---|
| R = H | (1-1-20c) |
| $CH_3$ | (1-1-21c) |
| $(CH_2)_3CH_3$ | (1-1-22c) |
| $(CH_2)_7CH_3$ | (1-1-23c) |
| $OCH_3$ | (1-1-24c) |
| $OCH_2CH_3$ | (1-1-25c) |
| $CH(CH_3)_2$ | (1-1-26c) |
| $C(CH_3)_3$ | (1-1-27c) |
| $N(CH_3)_2$ | (1-1-28c) |
| F | (1-1-29c) |
| Cl | (1-1-30c) |
| Br | (1-1-31c) |

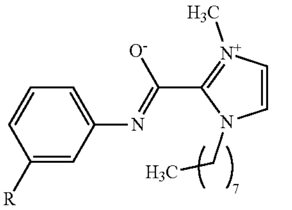

| | |
|---|---|
| R = $CH_3$ | (1-1-32c) |
| $(CH_2)_3CH_3$ | (1-1-33c) |
| $(CH_2)_7CH_3$ | (1-1-34c) |
| $OCH_3$ | (1-1-35c) |
| $OCH_2CH_3$ | (1-1-36c) |
| $CH(CH_3)_2$ | (1-1-37c) |
| $C(CH_3)_3$ | (1-1-38c) |
| $N(CH_3)_2$ | (1-1-39c) |
| F | (1-1-40c) |
| Cl | (1-1-41c) |
| Br | (1-1-42c) |

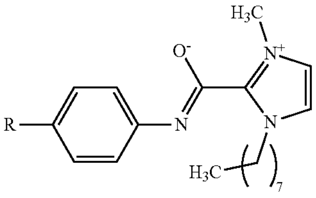

| | |
|---|---|
| R = $CH_3$ | (1-1-43c) |
| $(CH_2)_3CH_3$ | (1-1-44c) |
| $(CH_2)_7CH_3$ | (1-1-45c) |
| $OCH_3$ | (1-1-46c) |
| $OCH_2CH_3$ | (1-1-47c) |
| $CH(CH_3)_2$ | (1-1-48c) |
| $C(CH_3)_3$ | (1-1-49c) |
| $N(CH_3)_2$ | (1-1-50c) |
| F | (1-1-51c) |
| Cl | (1-1-52c) |
| Br | (1-1-53c) |

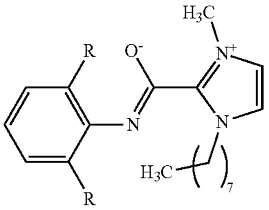

| | |
|---|---|
| R = $CH_3$ | (1-1-54c) |
| $(CH_2)_3CH_3$ | (1-1-55c) |
| $(CH_2)_7CH_3$ | (1-1-56c) |
| $OCH_3$ | (1-1-57c) |
| $OCH_2CH_3$ | (1-1-58c) |
| $CH(CH_3)_2$ | (1-1-59c) |
| $C(CH_3)_3$ | (1-1-60c) |
| $N(CH_3)_2$ | (1-1-61c) |
| F | (1-1-62c) |
| Cl | (1-1-63c) |
| Br | (1-1-64c) |

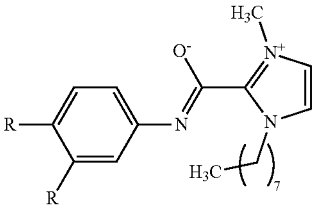

| | |
|---|---|
| R = $CH_3$ | (1-1-65c) |
| $(CH_2)_3CH_3$ | (1-1-66c) |
| $(CH_2)_7CH_3$ | (1-1-67c) |
| $OCH_3$ | (1-1-68c) |
| $OCH_2CH_3$ | (1-1-69c) |
| $CH(CH_3)_2$ | (1-1-70c) |
| $C(CH_3)_3$ | (1-1-71c) |
| $N(CH_3)_2$ | (1-1-72c) |
| F | (1-1-73c) |
| Cl | (1-1-74c) |
| Br | (1-1-75c) |

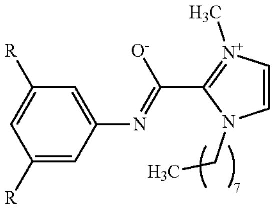

| | |
|---|---|
| R = $CH_3$ | (1-1-76c) |
| $(CH_2)_3CH_3$ | (1-1-77c) |
| $(CH_2)_7CH_3$ | (1-1-78c) |
| $OCH_3$ | (1-1-79c) |
| $OCH_2CH_3$ | (1-1-80c) |
| $CH(CH_3)_2$ | (1-1-81c) |
| $C(CH_3)_3$ | (1-1-82c) |
| $N(CH_3)_2$ | (1-1-83c) |
| F | (1-1-84c) |
| Cl | (1-1-85c) |
| Br | (1-1-86c) |

-continued
(1-1-87c)
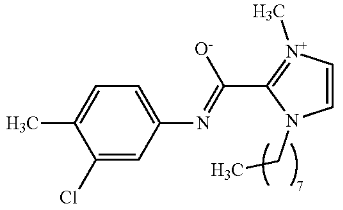
(1-1-88c)
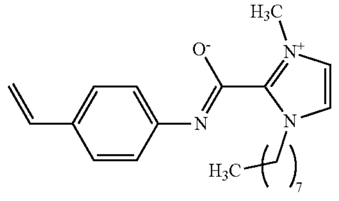
(1-1-89c)
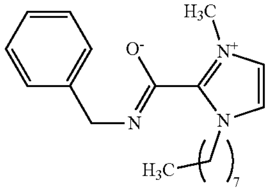
(1-1-90c)
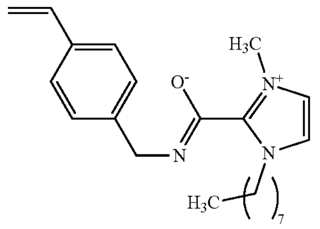
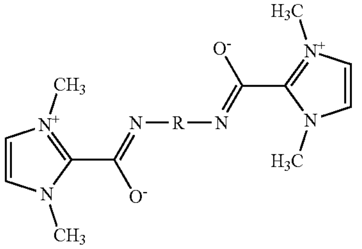
R = —$CH_2$— (1-2-1a)
—$CH_2CH_2$— (1-2-2a)
—$CH_2(CH_2)_2CH_2$— (1-2-3a)
—$CH_2(CH_2)_4CH_2$— (1-2-4a)
—$CH_2(CH_2)_6CH_2$— (1-2-5a)
—$CH_2(CH_2)_8CH_2$— (1-2-6a)
—$CH_2(CH_2)_{10}CH_2$— (1-2-7a)
(1-2-8a)
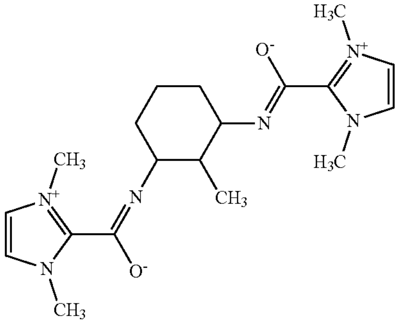
(1-2-9a)
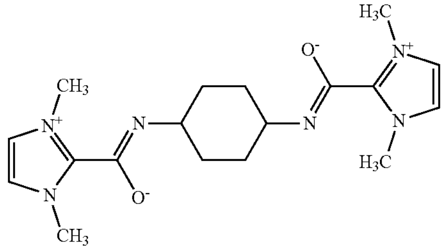
(1-2-10a)
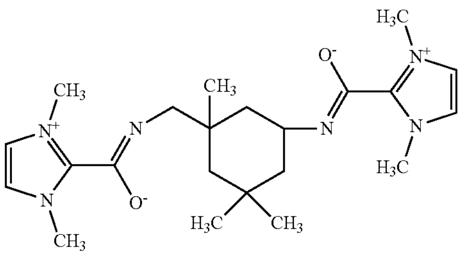
(1-2-11a)
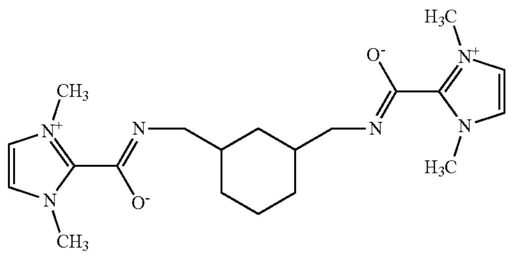

-continued
(1-2-12a)
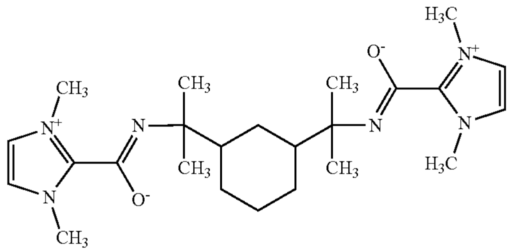
(1-2-13a)
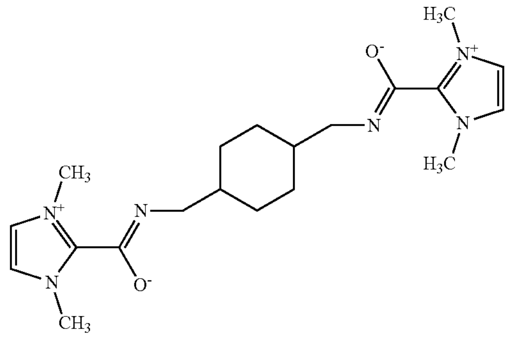
(1-2-14a)
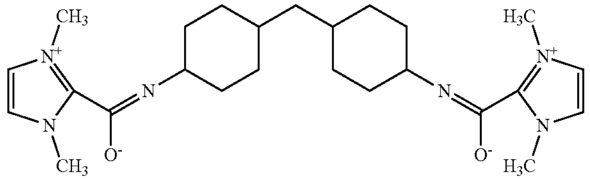
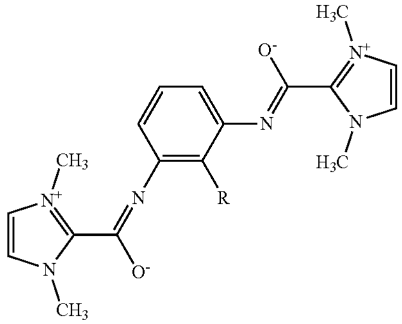
R = H (1-2-15a)
$CH_3$ (1-2-16a)
(1-2-17a)
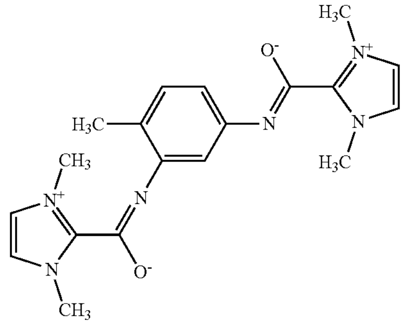
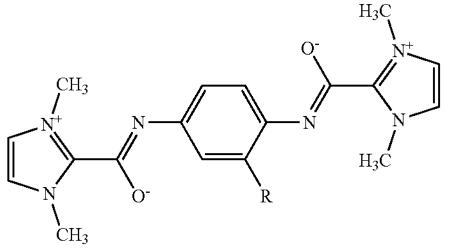
R = H (1-2-18a)
$CH_3$ (1-2-19a)
(1-2-20a)
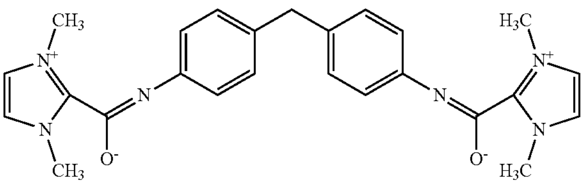
(1-2-21a)
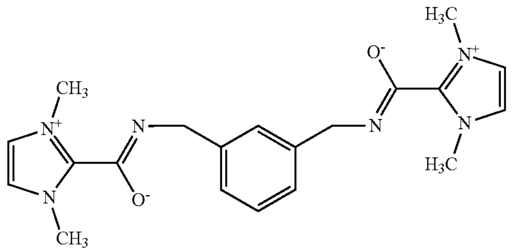
(1-2-22a)
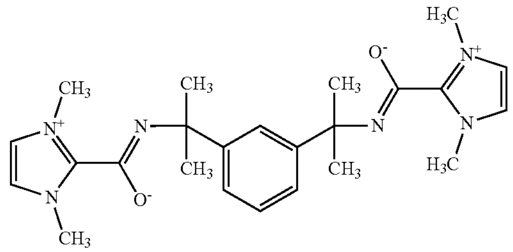

-continued
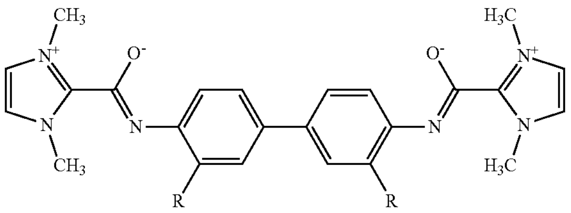
R = $CH_3$ (1-2-23a)
$CH_2CH_3$ (1-2-24a)
$OCH_3$ (1-2-25a)
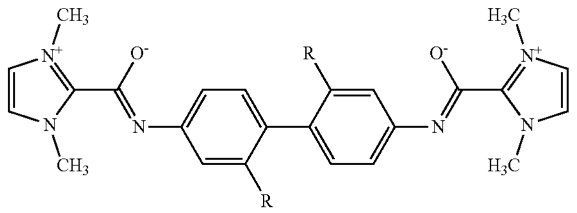
R = $CH_3$ (1-2-26a)
$CF_3$ (1-2-27a)
(1-2-28a)
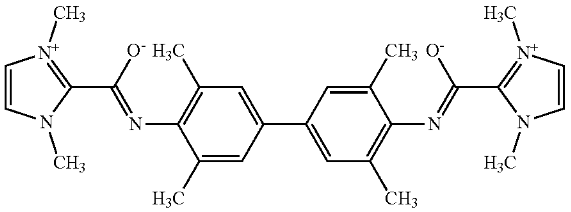
(1-2-29a)
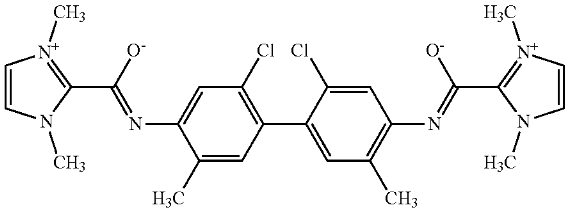
(1-2-30a)
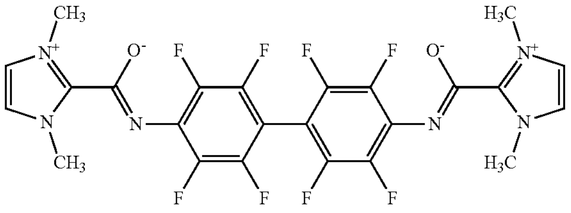
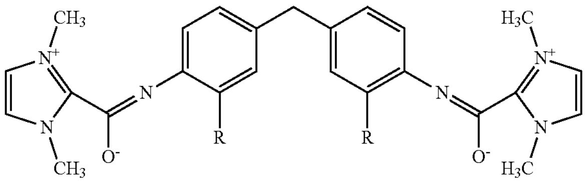
R = $CH_3$ (1-2-31a)
Cl (1-2-32a)
(1-2-33a)
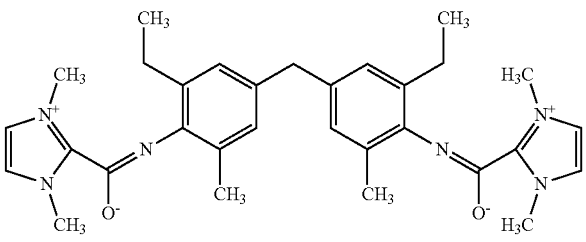

-continued
(1-2-34a)
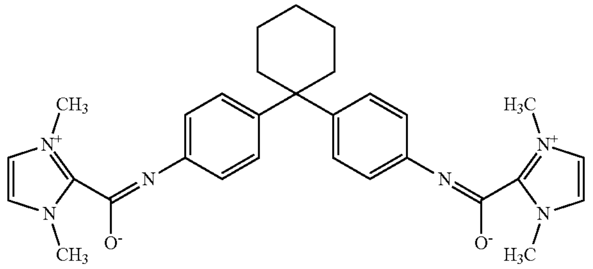
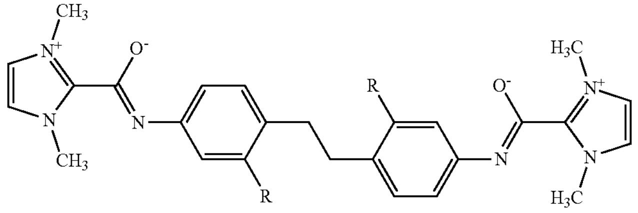
R = H (1-2-35a)
$CH_3$ (1-2-36a)
(1-2-37a)
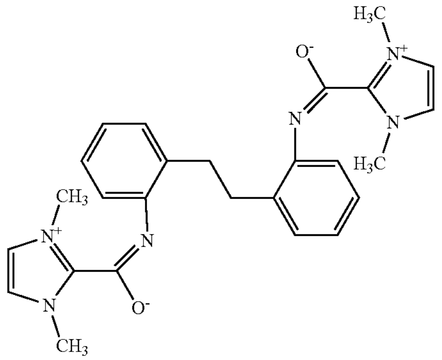
(1-2-38a)
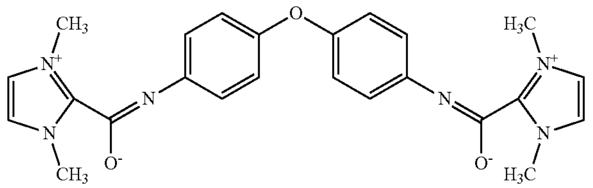
(1-2-39a)
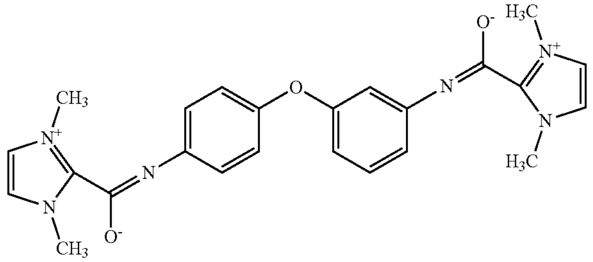
(1-2-40a)
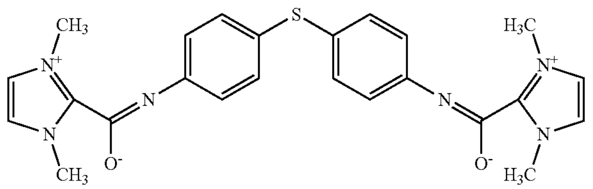

-continued
(1-2-41a)
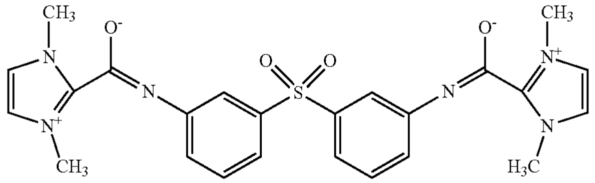
(1-2-42a)
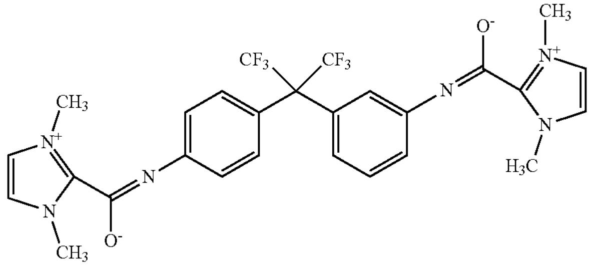
(1-2-43a)
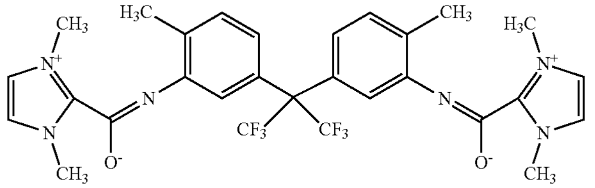
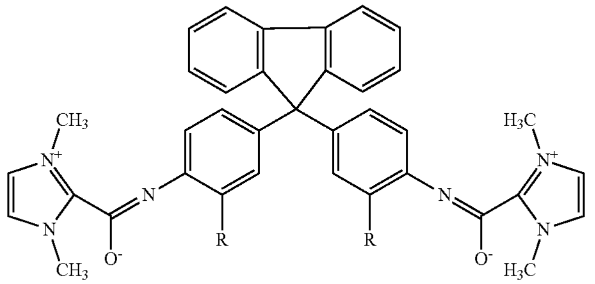
R = H (1-2-44a)
CH$_3$ (1-2-45a)
F (1-2-46a)
Cl (1-2-47a)
(1-2-48a)
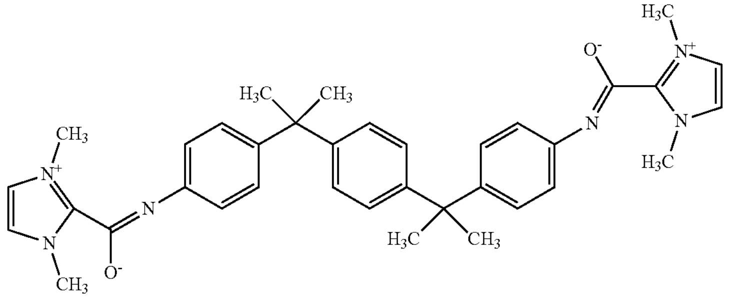
(1-2-49a)
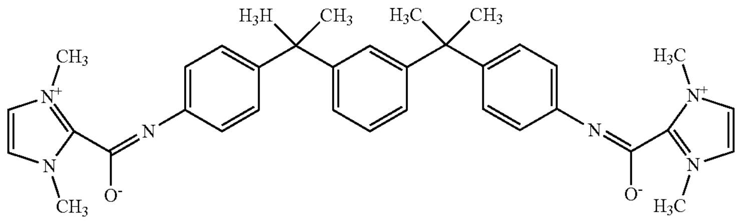

-continued
(1-2-50a)
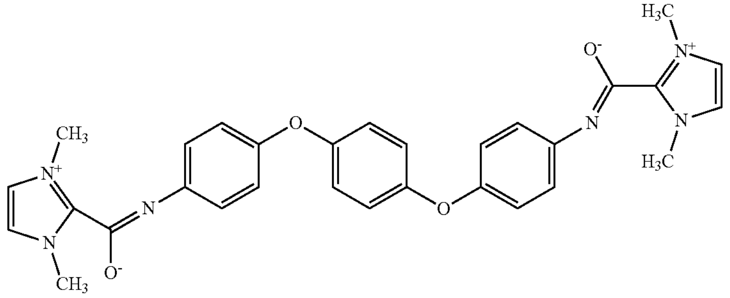
(1-2-51a)
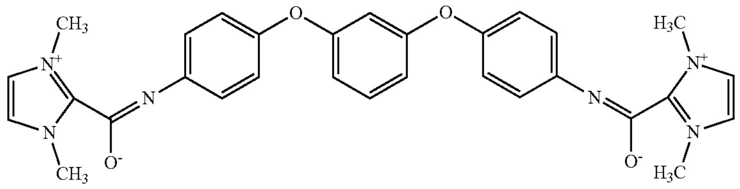
(1-2-52a)
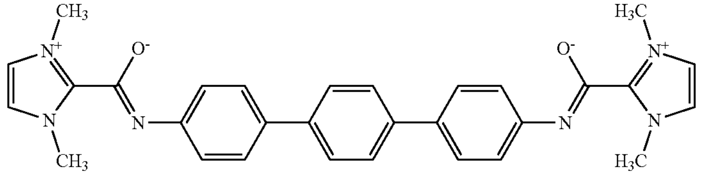
(1-2-53a)
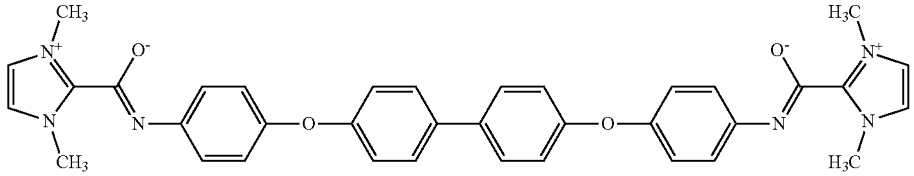
(1-2-54a)
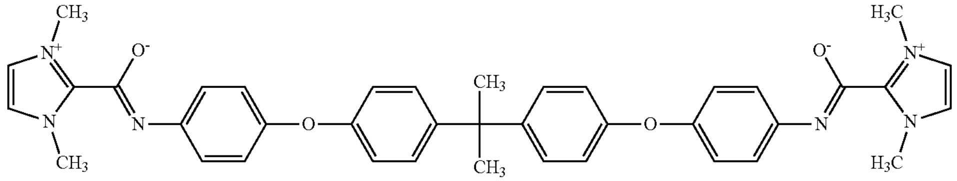
(1-2-55a)
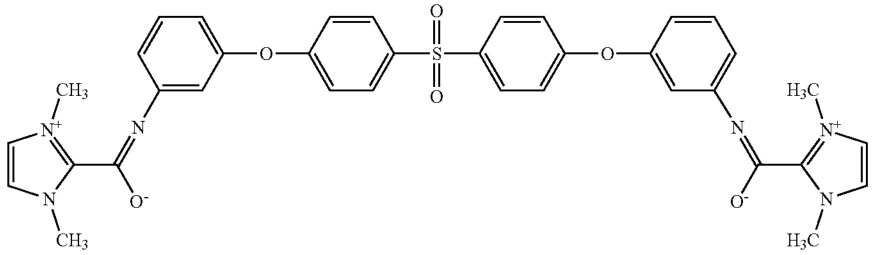
(1-2-56a)
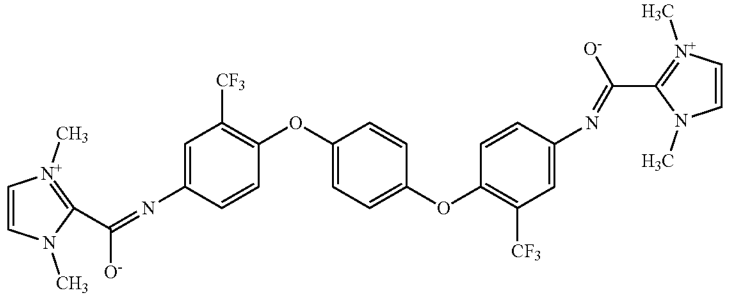

-continued
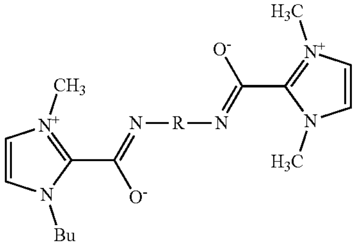
| | | |
|---|---|---|
| R = | $—CH_2—$ | (1-2-1b) |
| | $—CH_2CH_2—$ | (1-2-2b) |
| | $—CH_2(CH_2)_2CH_2—$ | (1-2-3b) |
| | $—CH_2(CH_2)_4CH_2—$ | (1-2-4b) |
| | $—CH_2(CH_2)_6CH_2—$ | (1-2-5b) |
| | $—CH_2(CH_2)_8CH_2—$ | (1-2-6b) |
| | $—CH_2(CH_2)_{10}CH_2—$ | (1-2-7b) |
(1-2-8b)
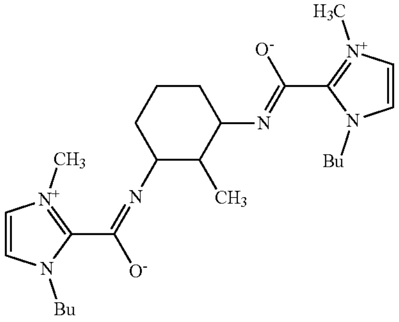
(1-2-9b)
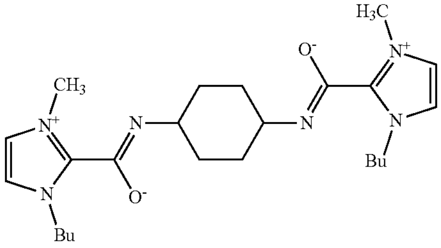
(1-2-10b)
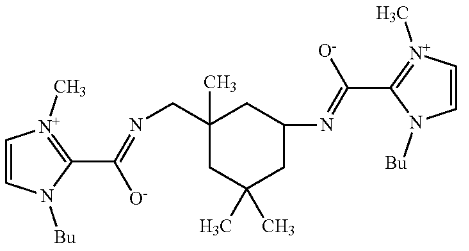
(1-2-11b)
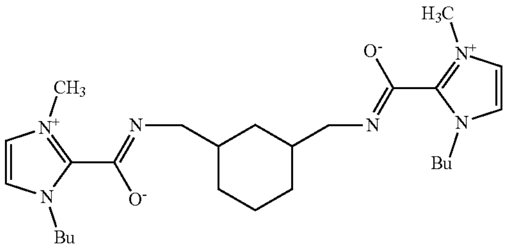
(1-2-12b)
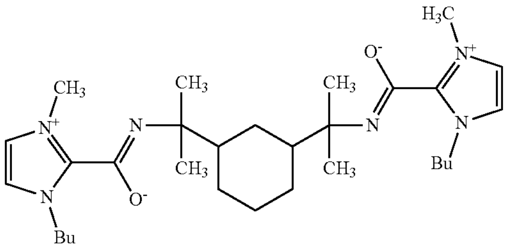
(1-2-13b)
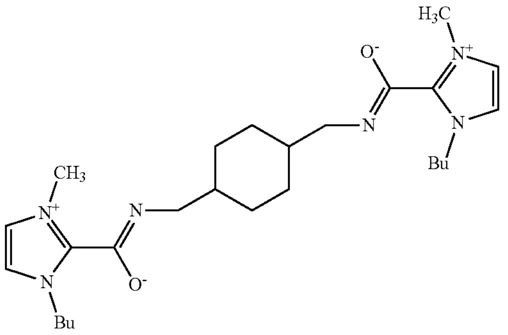
(1-2-14b)
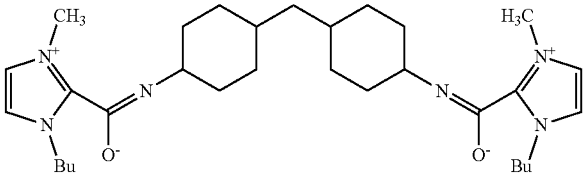

-continued
(1-2-17b)
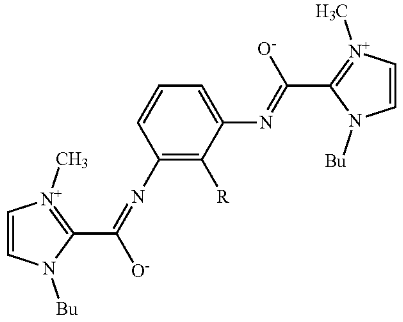
R = H (1-2-15b)
$CH_3$ (1-2-16b)
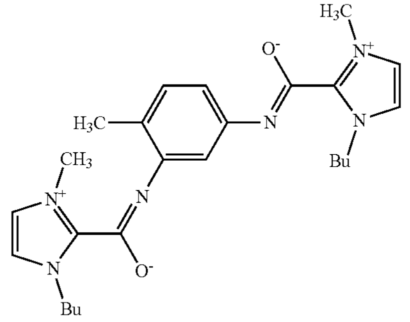
(1-2-20b)
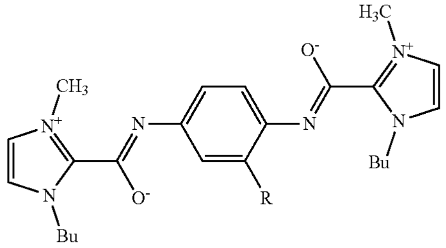
R = H (1-2-18b)
$CH_3$ (1-2-19b)
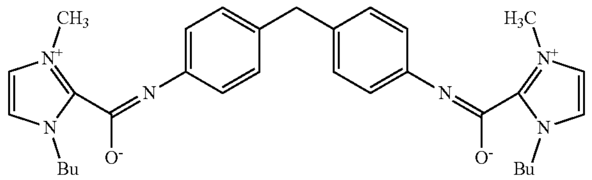
(1-2-21b)
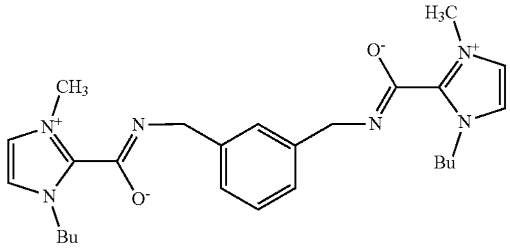
(1-2-22b)
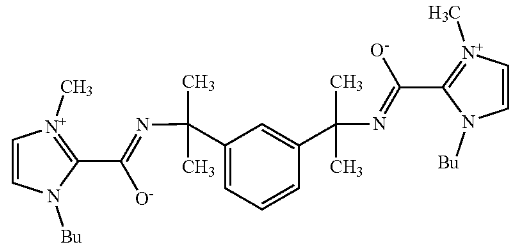
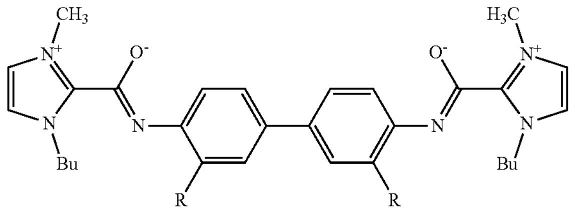
R = $CH_3$ (1-2-23b)
$CH_2CH_3$ (1-2-24b)
$OCH_3$ (1-2-25b)
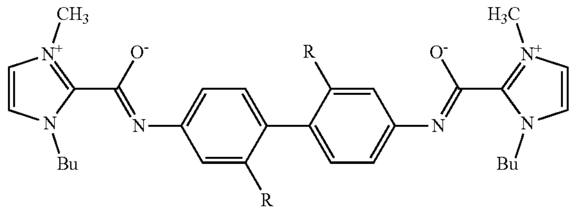
R = $CH_3$ (1-2-26b)
$CF_3$ (1-2-27b)
(1-2-28b)
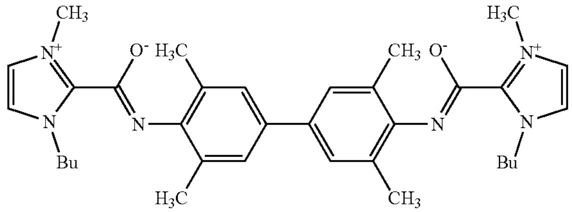

-continued
(1-2-29b)
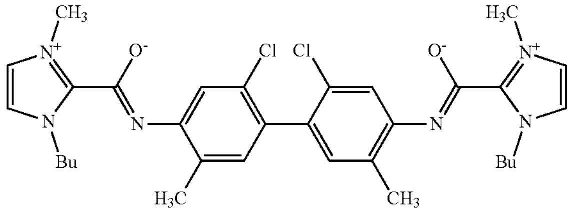
(1-2-30b)
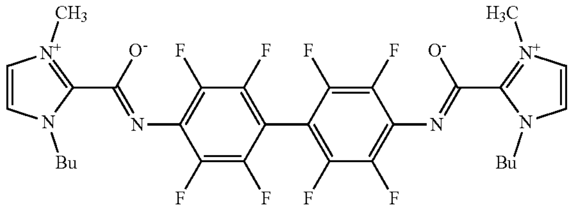
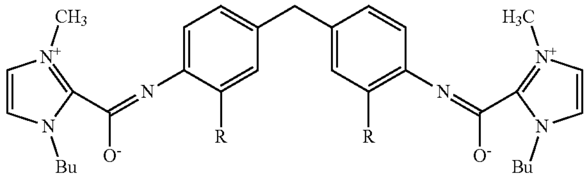
R = $CH_3$ (1-2-31b)
Cl (1-2-32b)
(1-2-33b)
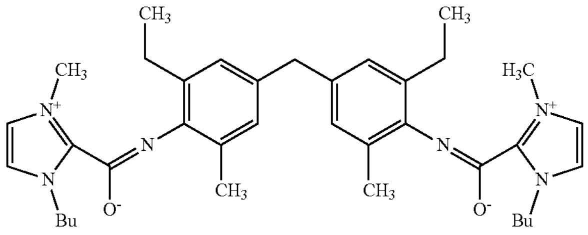
(1-2-34b)
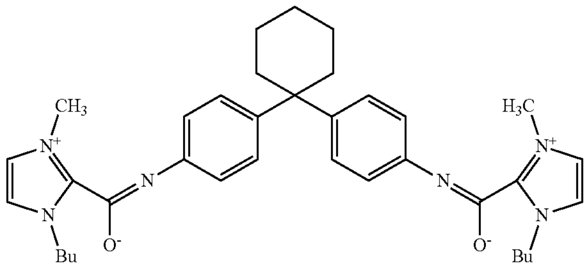
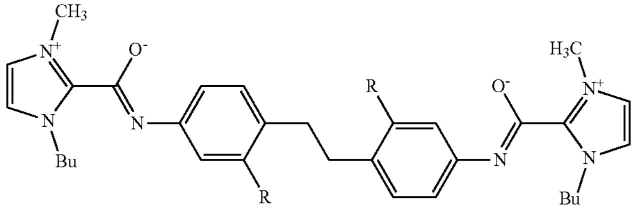
R = H (1-2-35b)
$CH_3$ (1-2-36b)

-continued
(1-2-37b)
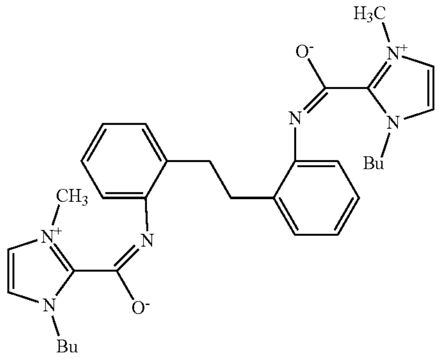
(1-2-38b)
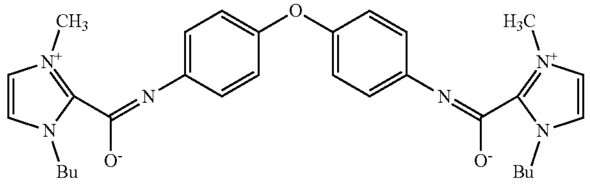
(1-2-39b)
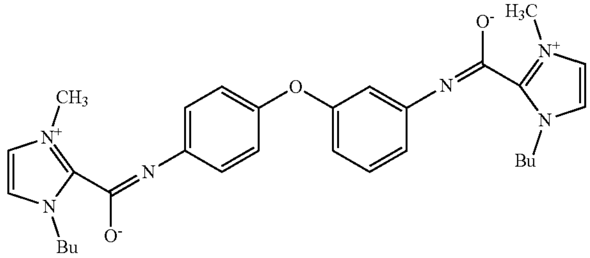
(1-2-40b)
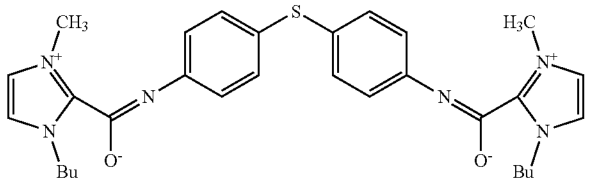
(1-2-41b)
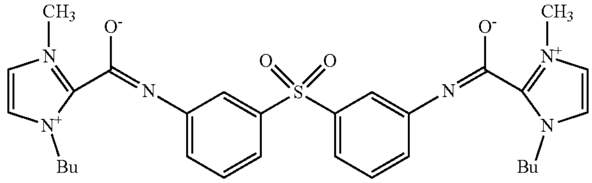
(1-2-42b)
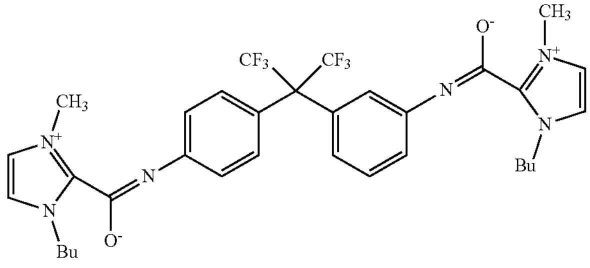

-continued
(1-2-43b
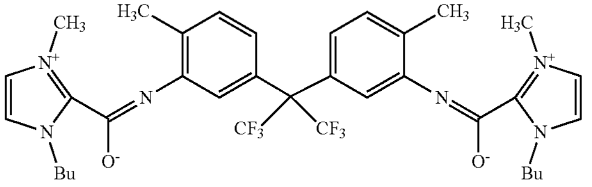
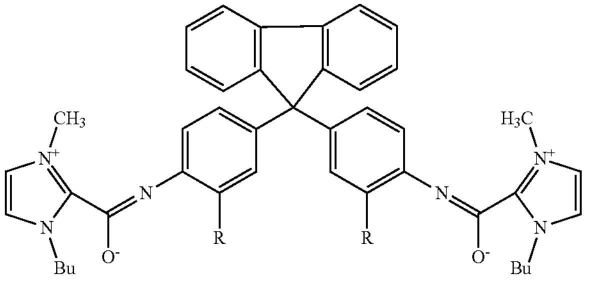
R = H (1-2-44b)
CH3 (1-2-45b)
F (1-2-46b)
Cl (1-2-47b)
(1-2-48b)
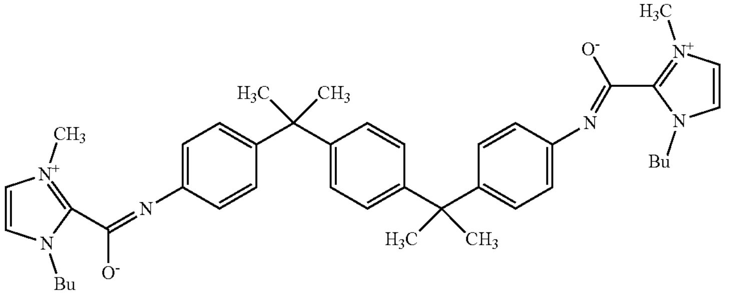
(1-2-49b)
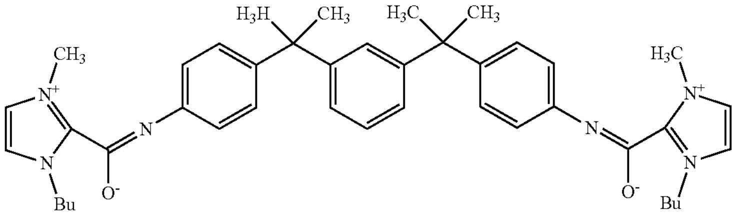
(1-2-50b)
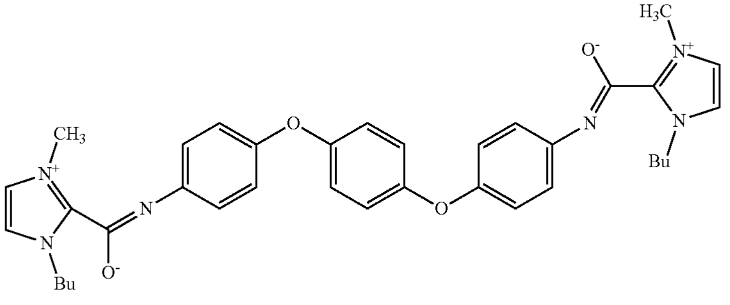
(1-2-51b)
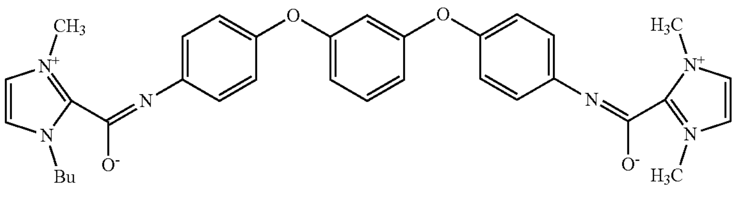

-continued
(1-2-52b)
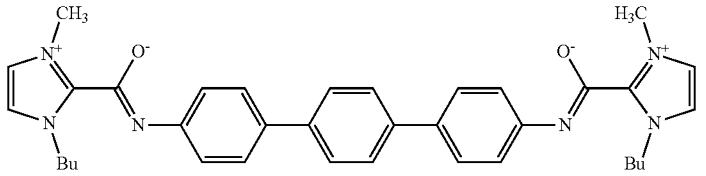
(1-2-53b)
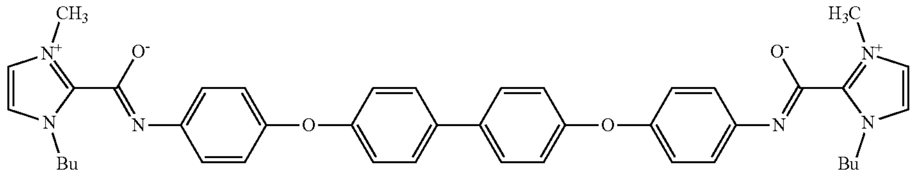
(1-2-54b)
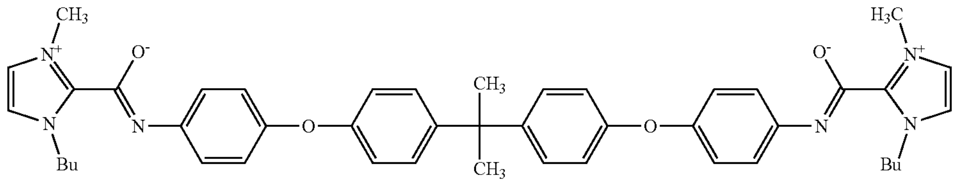
(1-2-55b)
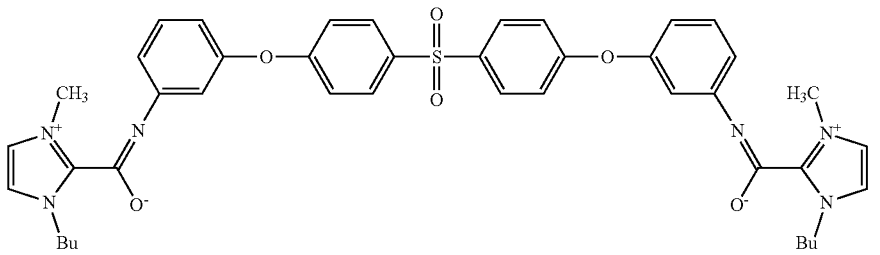
(1-2-56b)
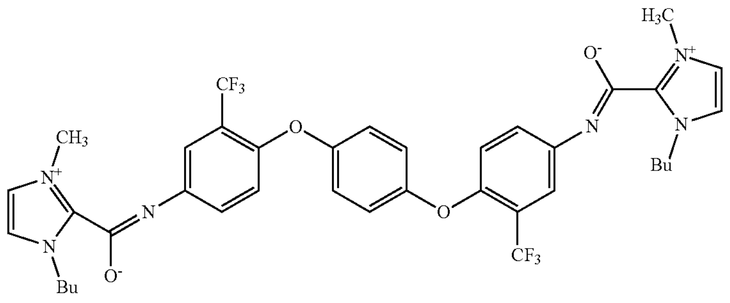

-continued
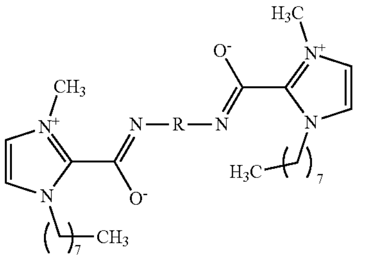
R = —$CH_2$— (1-2-1c)
—$CH_2CH_2$— (1-2-2c)
—$CH_2(CH_2)_2CH_2$— (1-2-3c)
—$CH_2(CH_2)_4CH_2$— (1-2-4c)
—$CH_2(CH_2)_6CH_2$— (1-2-5c)
—$CH_2(CH_2)_8CH_2$— (1-2-6c)
—$CH_2(CH_2)_{10}CH_2$— (1-2-7c)
(1-2-8c)
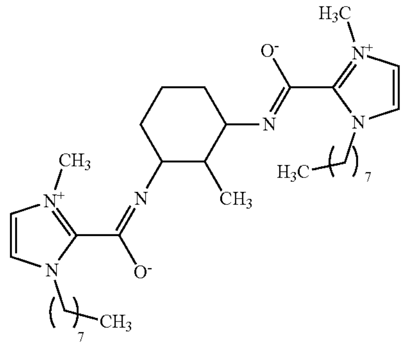
(1-2-9c)
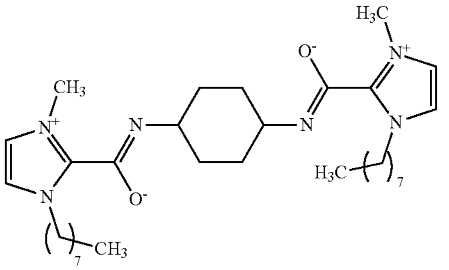
(1-2-10)
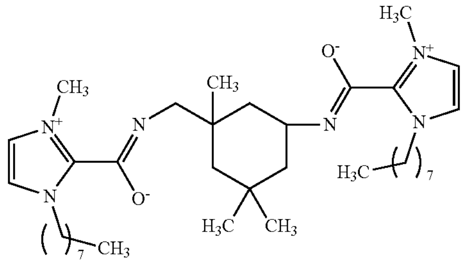
(1-2-11c)
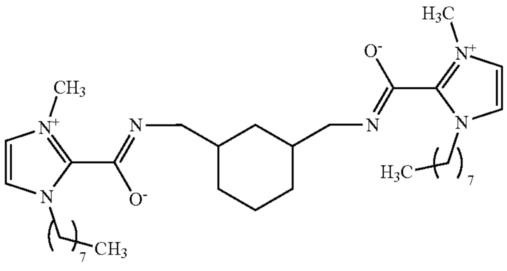
(1-2-12c)
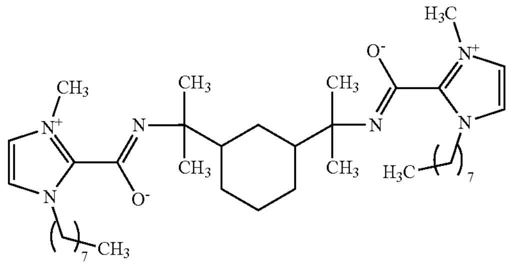
(1-2-13c)
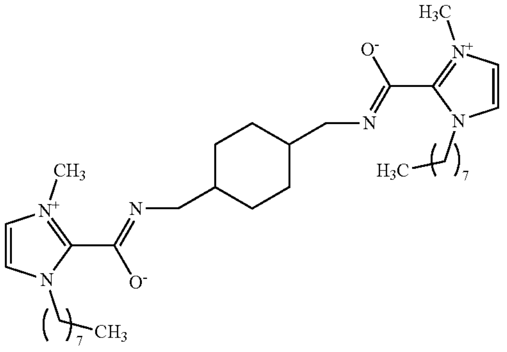

-continued
(1-2-14c)
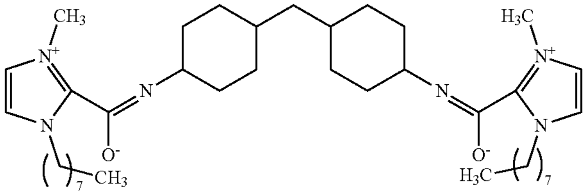
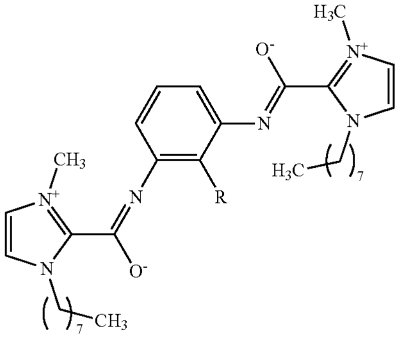
R = H (1-2-15c)
$CH_3$ (1-2-16c)
(1-2-17c)
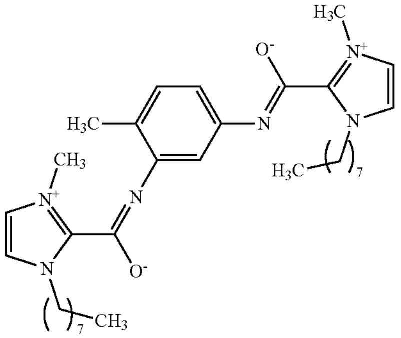
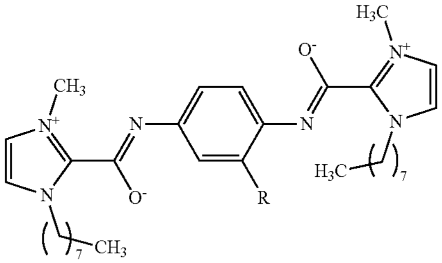
R = H (1-2-18c)
$CH_3$ (1-2-19c)
(1-2-20c)
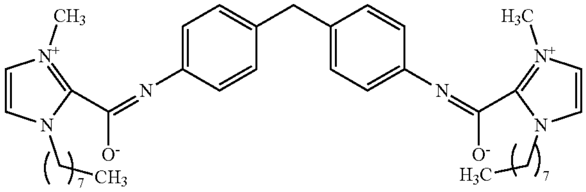
(1-2-21c)
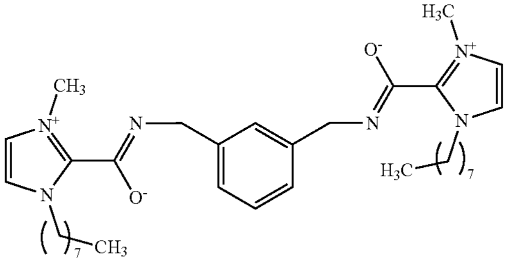
(1-2-22c)
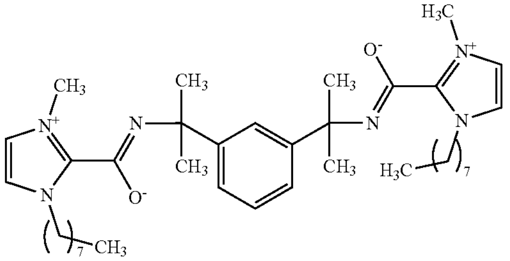

-continued
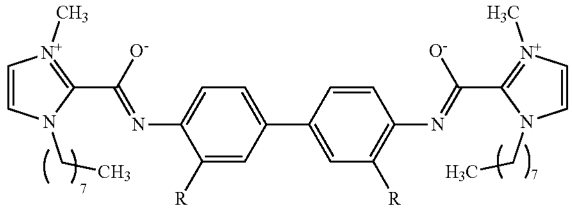
R = $CH_3$ (1-2-23c)
$CH_2CH_3$ (1-2-24c)
$OCH_3$ (1-2-25c)
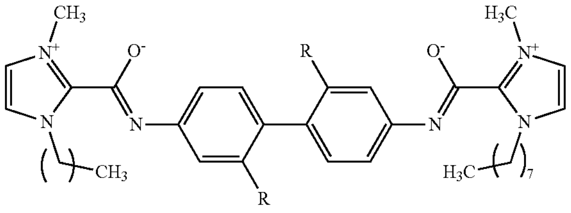
R = $CH_3$ (1-2-26c)
$CF_3$ (1-2-27c)
(1-2-28c)
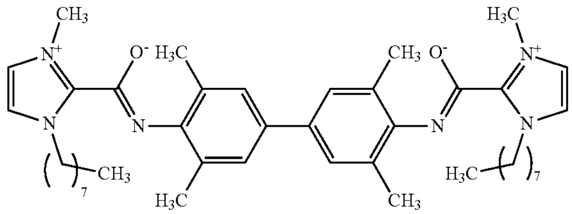
(1-2-29c)
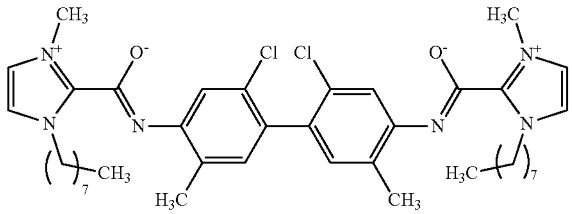
(1-2-30c)
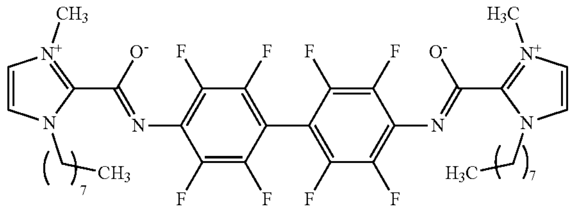
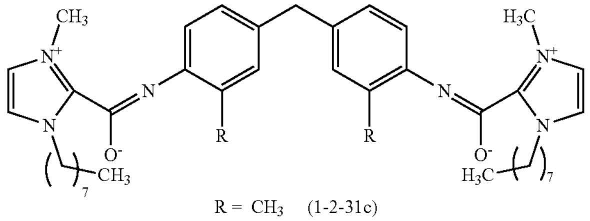
R = $CH_3$ (1-2-31c)
Cl (1-2-32c)
(1-2-33c)
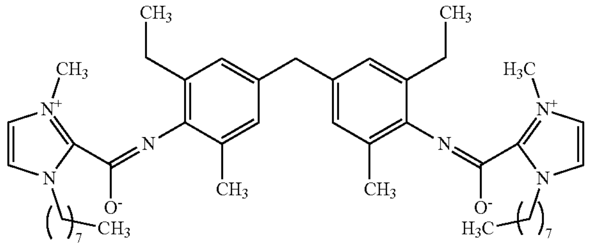

-continued
(1-2-34c)
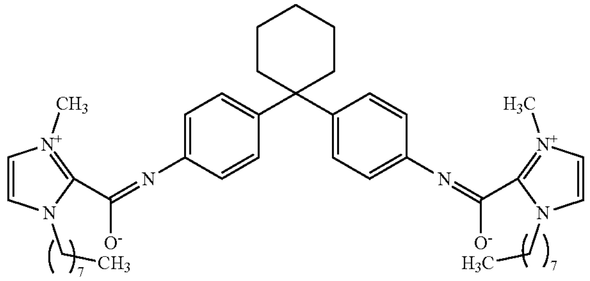
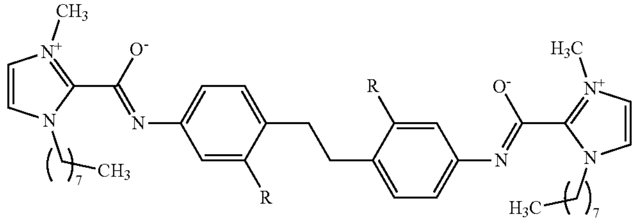
R = H (1-2-35c)
$CH_3$ (1-2-36c)
(1-2-37c)
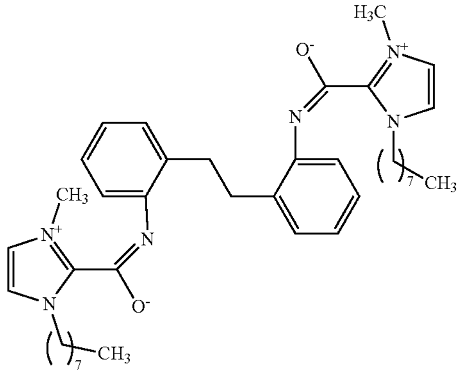
(1-2-38c)
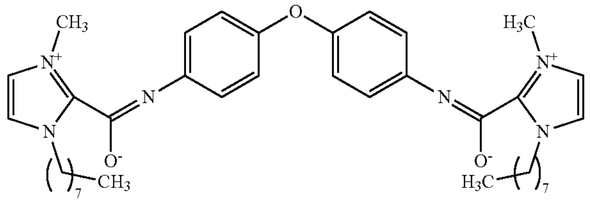
(1-2-39c)
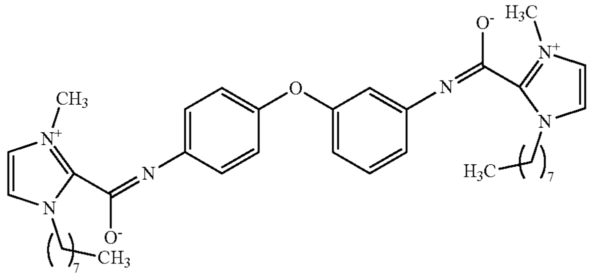

-continued
(1-2-40c)
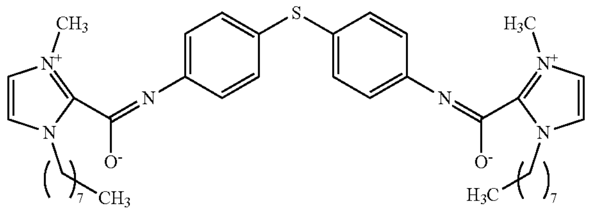
(1-2-41c)
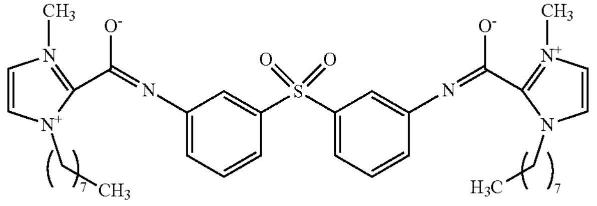
(1-2-42c)
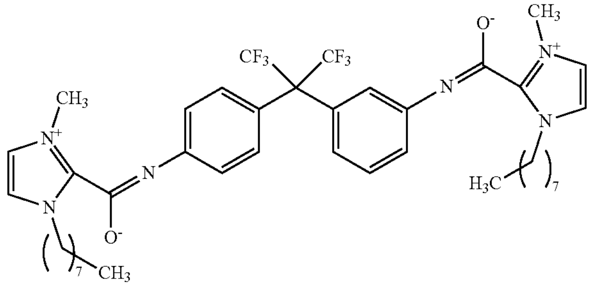
(1-2-43c)
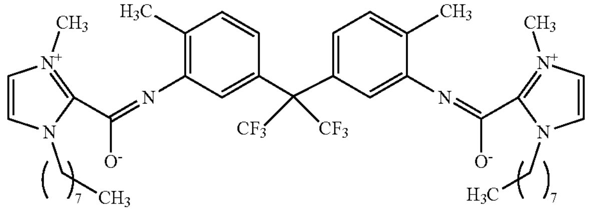
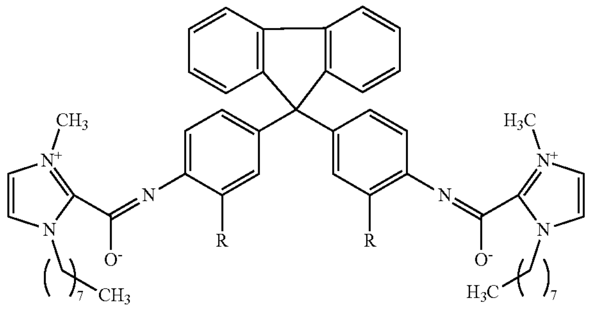
R = H (1-2-44c)
$CH_3$ (1-2-45c)
F (1-2-46c)
Cl (1-2-47c)

-continued
(1-2-48c)
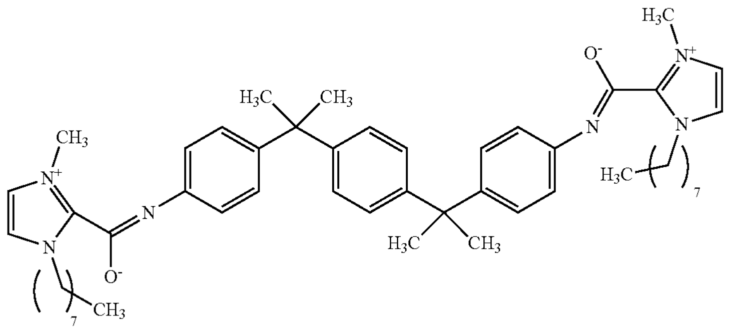
(1-2-49c)
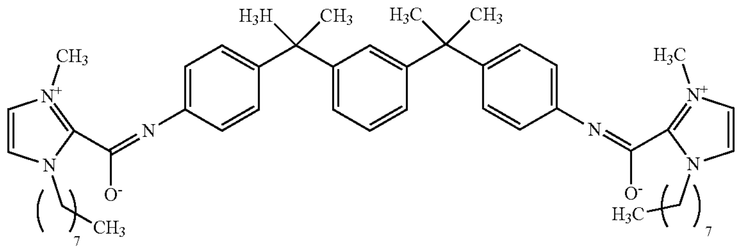
(1-2-50c)
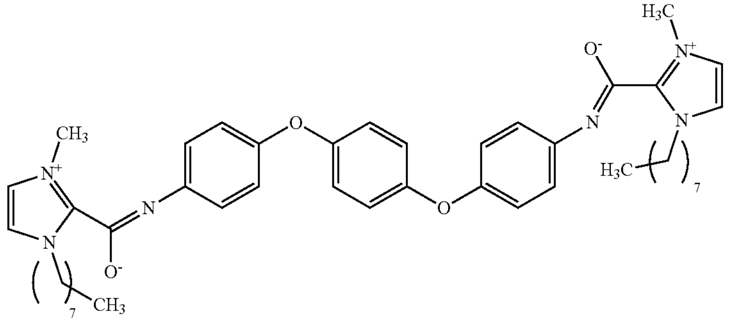
(1-2-51c)
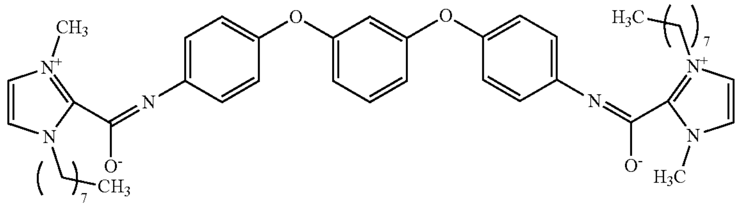
(1-2-52c)
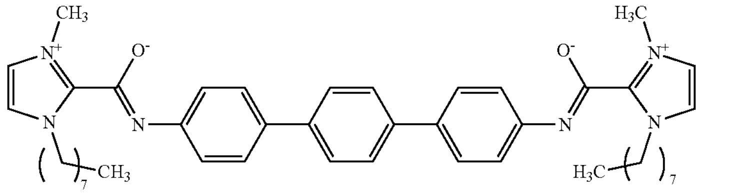
(1-2-53c)
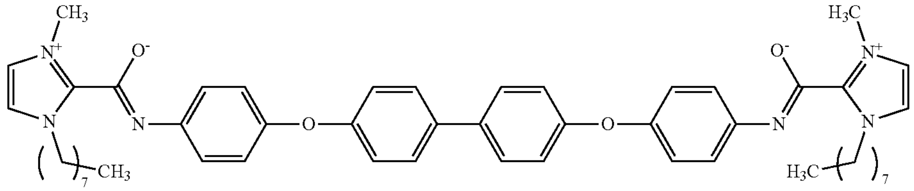

-continued
(1-2-54c)
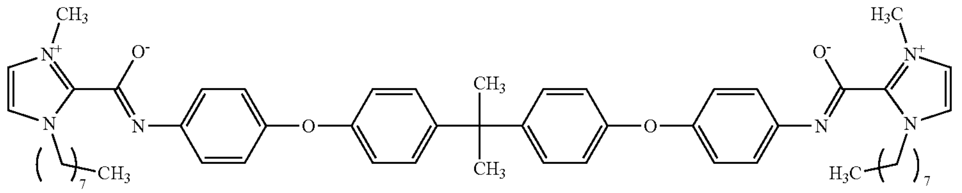
(1-2-55c)
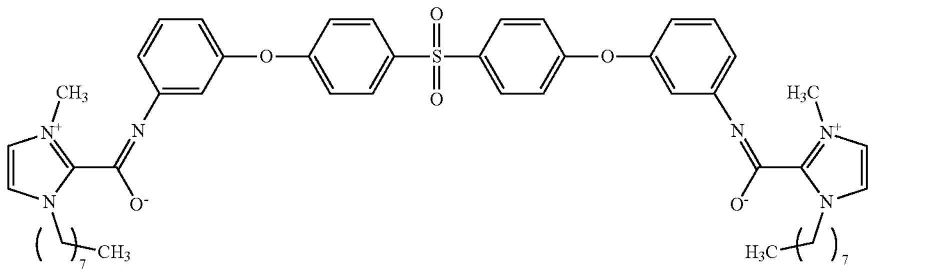
(1-2-56c)
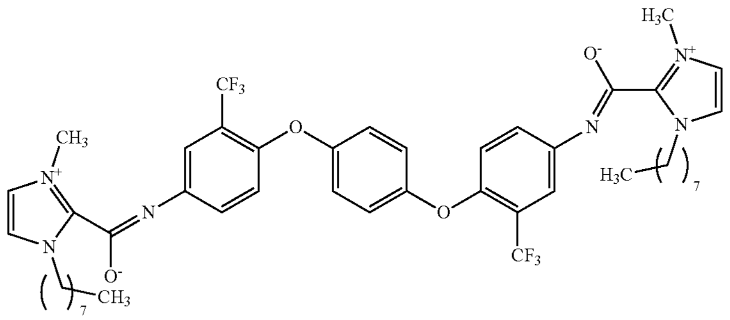
(1-3-1a)
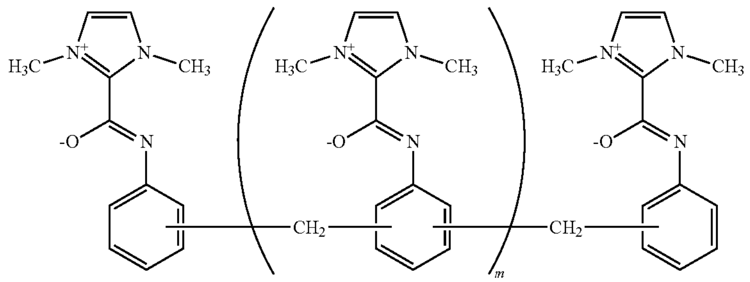
(1-3-1b)
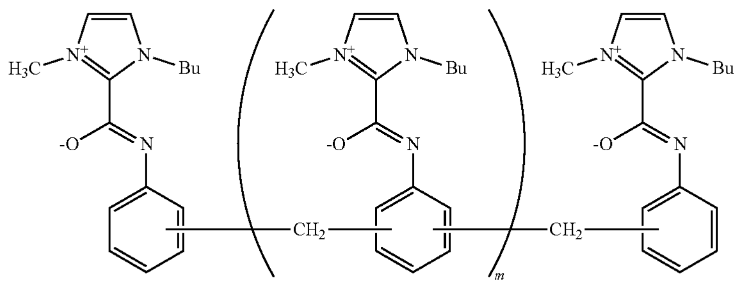

-continued (1-3-1c)

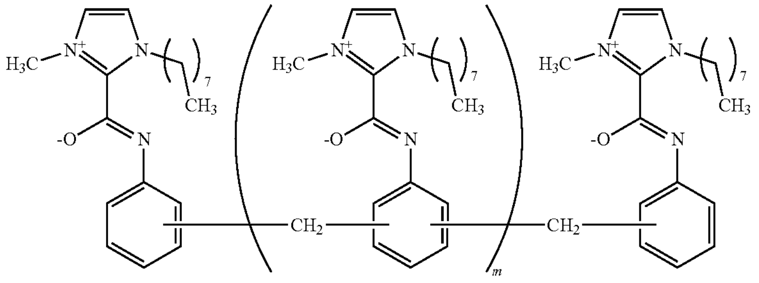

In the formulas (1-3-1a) to (1-3-1c), m is as defined above.

Preferable examples of the amidate compound (1) include compounds represented by the formulas (1-1-5a), (1-1-20a), (1-1-30a), (1-1-41a), (1-1-45a), (1-1-46a), (1-1-48a), (1-1-52a), (1-1-59a), (1-1-88a), (1-1-89a), (1-1-90a), (1-1-5b), (1-1-20b), (1-1-30b), (1-1-41b), (1-1-45b), (1-1-46b), (1-1-48b), (1-1-52b), (1-1-59b), (1-1-88b), (1-1-89b), (1-1-90b), (1-1-5c), (1-1-20c), (1-1-30c), (1-1-41c), (1-1-45c), (1-1-46c), (1-1-48c), (1-1-52c), (1-1-59c), (1-1-88c), (1-1-89c), (1-1-90c), (1-2-17a), (1-2-20a), (1-2-41a), (1-2-48a), (1-2-49a), (1-2-51a), (1-2-17b), (1-2-20b), (1-2-41b), (1-2-48b), (1-2-49b), (1-2-51b), (1-2-17c), (1-2-20c), (1-2-41c), (1-2-48c), (1-2-49c), and (1-2-51c); and particularly preferably compounds represented by the formulas (1-1-5a), (1-1-20a), (1-1-30a), (1-1-41a), (1-1-45a), (1-1-46a), (1-1-48a), (1-1-52a), (1-1-59a), (1-1-88a), (1-1-89a), (1-1-90a), (1-1-20b), (1-1-20c), (1-2-17a), (1-2-20a), (1-2-41a), (1-2-48a), (1-2-49a), (1-2-51a), and (1-2-20c).

In one embodiment of the present invention, the amidate compound (1) does not include 1,3-dimethylimidazolium-2-N-(p-chlorophenyl)amidate represented by (1-1-52a) and 1,3-dimethylimidazolium-2-N-(3',5'-dichlorophenyl)amidate represented by (1-1-85a).

When the amidate compound (1) of the present invention is an isomer, such as an enantiomer, a stereoisomer, or a regioisomer, the amidate compound (1) of the present invention includes a mixture of any isomers, unless the isomer is specified. For example, when the amidate compound (1) is an enantiomer, the amidate compound (1) of the present invention also includes enantiomers divided from the racemic form. These isomers can be obtained as single compounds by conventionally known separation methods (concentration, solvent extraction, column chromatography, recrystallization, etc.).

Moreover, the amidate compound (1) is considered to be isomerized by resonance. For example, the compound represented by the formula (1) wherein X is a nitrogen atom is considered to have the following resonance structure:

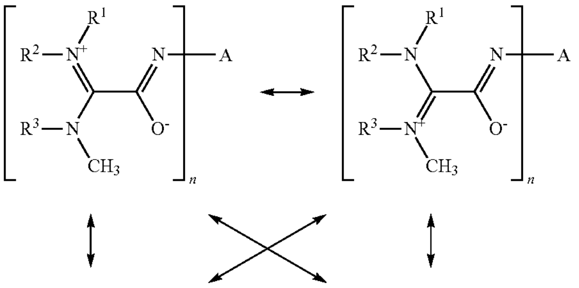

-continued

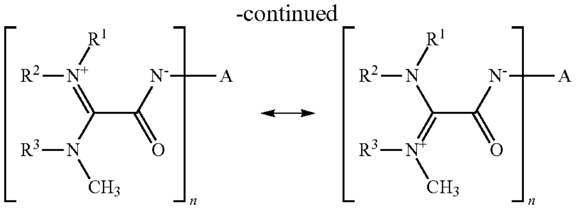

wherein A, $R^1$, $R^2$, $R^3$, and n are as defined above.

The amidate compound (1) of the present invention is produced by the following step 1 and the following step 2 or step 2'.

Step 1: reacting a nitrogen-containing organic compound represented by the following formula (3) (hereinafter referred to as the "nitrogen-containing compound (3)") and dimethyl carbonate to produce a carboxylate compound represented by the following formula (4) (hereinafter referred to as the "carboxylate compound (4)"):

Formula (3):

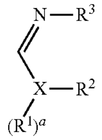

(3)

wherein $R^1$, $R^2$, $R^3$, X, and a are as defined above;

Formula (4):

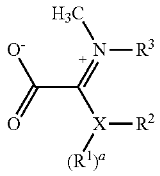

(4)

wherein $R^1$, $R^2$, $R^3$, X, and a are as defined above.

Step 2: reacting an isocyanate compound represented by the following formula (5) (hereinafter referred to as the "isocyanate compound (5)") and the carboxylate compound (4) to produce an amidate compound.

Formula (5):

$$A{-}[{-}NCO]_n \quad (5)$$

wherein A and n are as defined above.

Step 2': reacting a urethane compound represented by the following formula (6) (hereinafter referred to as the "urethane compound (6)") and the carboxylate compound (4) to produce an amidate compound (1).

Formula (6):

(6)

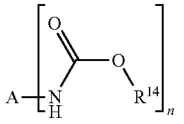

wherein $R^{14}$ is a hydrocarbon group that may contain a heteroatom, and A and n are as defined above.

First, step 1 is explained.

In the formula (3), $R^1$, $R^2$, $R^3$, X, and a are as defined above. In the present invention, $R^2$ and $R^3$ in the formula (3) are preferably bonded together to form a ring structure, in terms of easy availability. The nitrogen-containing organic compound (3) in which a ring is formed is preferably a nitrogen-containing organic compound represented by the following formula (3-1), (3-2), or (3-3); and particularly preferably a nitrogen-containing organic compound represented by the formula (3-1).

Formula (3-1):

(3-1)

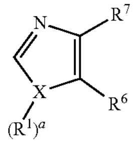

wherein $R^1$, $R^6$, $R^7$, X, and a are as defined above.

Formula (3-2):

(3-2)

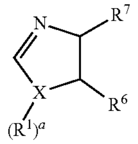

wherein $R^1$, $R^8$, $R^9$, X, and a are as defined above.

Formula (3-3):

(3-3)

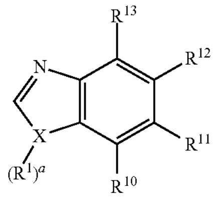

wherein $R^1$, $R^{10}$, $R^{11}$, $R^{12}$, $R^{13}$, X, and a are as defined above.

In the formula (3-1), $R^1$, $R^6$, $R^7$, X, and a are as defined above. Specific examples of the nitrogen-containing compound represented by the formula (3-1) include 1-methylimidazole, 1-ethylimidazole, 1-propylimidazole, 1-isopropylimidazole, 1-butylimidazole, 1-tert-butylimidazole, 1-pentylimidazole, 1-hexylimidazole, 1-heptylimidazole, 1-octylimidazole, 1-nonylimidazole, 1-decylimidazole, 1-allylimidazole, 1-benzylimidazole, 1-(2-methoxyethyl) imidazole, 1-(2-ethoxyethyl) imidazole, 1-(2-dimethylaminoethyl)imidazole, 1,4,5-trimethylimidazole,
oxazole, 5-methyloxazole, 4,5-dimethyloxazole,
thiazole, 4-methylthiazole, 5-methylthiazole, 4,5-dimethylthiazole, and the like; preferably 1-methylimidazole, 1-ethylimidazole, 1-propylimidazole, 1-butylimidazole, and 1-octylimidazole; and particularly preferably 1-methylimidazole, 1-butylimidazole, and 1-octylimidazole.

In the formula (3-2), $R^1$, $R^8$, $R^9$, X, and a are as defined above. Specific examples of the nitrogen-containing compound represented by the formula (3-2) include 1-methylimidazoline, 1-ethylimidazoline, 1-propylimidazoline, 1-isopropylimidazoline, 1-butylimidazoline, 1-tert-butylimidazoline, 1-pentylimidazoline, 1-hexylimidazoline, 1-heptylimidazoline, 1-octylimidazoline, 1-nonylimidazoline, 1-decylimidazoline, 1-allylimidazoline, 1-benzylimidazoline, 1-(2-methoxyethyl) imidazoline, 1-(2-ethoxyethyl) imidazoline, 1-(2-dimethylaminoethyl) imidazoline, 1,4,5-trimethylimidazoline,
oxazoline, 5-methyloxazoline, 4,5-dimethyloxazoline,
thiazoline, 4-methylthiazoline, 5-methylthiazoline, 4,5-dimethylthiazoline, and the like; preferably 1-methylimidazoline, 1-ethylimidazoline, 1-propylimidazoline, and 1-butylimidazoline; and particularly preferably 1-methylimidazoline.

In the formula (3-3), $R^1$, $R^{10}$, $R^{11}$, $R^{12}$, $R^{13}$, X, and a are as defined above. Specific examples of the nitrogen-containing compound represented by the formula (3-3) include 1-methylbenzimidazole, 1-ethylbenzimidazole, 1-propylbenzimidazole, 1-butylbenzimidazole, 1-pentylbenzimidazole, 1-hexylbenzimidazole, 1-heptylbenzimidazole, 1-octylbenzimidazole, 1-nonylbenzimidazole, 1-decylbenzimidazole, 1-allylbenzimidazole, 1-benzylbenzimidazole, 1,6-dimethylbenzimidazole, 1-acetyl-6-methylbenzimidazole, 1,6,7-trimethylbenzimidazole,
benzoxazole, benzothiazole, and the like; preferably 1-methylbenzimidazole, 1-ethylbenzimidazole, 1-propylbenzimidazole, and 1-butylbenzimidazole; and particularly preferably 1-methylbenzimidazole.

In the formula (4), $R^1$, $R^2$, $R^3$, X, and a are as defined above. In the present invention, $R^2$ and $R^3$ of the carboxylate compound represented by the formula (4) are preferably bonded together to form a ring structure. The carboxylate compound (4) in which a ring is formed is preferably a carboxylate compound represented by the following formula (4-1), (4-2), or (4-3); and particularly preferably a carboxylate compound represented by the formula (4-1).

Formula (4-1):

(4-1)

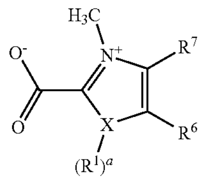

wherein $R^1$, $R^6$, $R^7$, X, and a are as defined above.

Formula (4-2)

(4-2)

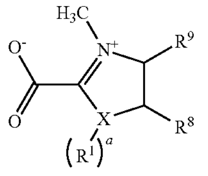

wherein $R^1$, $R^8$, $R^9$, X, and a are as defined above.

Formula (4-3)

(4-3)

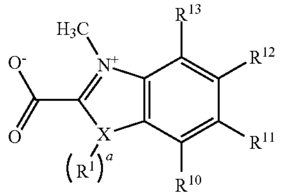

wherein $R^1$, $R^{10}$, $R^{11}$, $R^{12}$, $R^{13}$, X, and a are as defined above.

In the formula (4-1), $R^1$, $R^6$, $R^7$, X, and a are as defined above. Specific examples of the carboxylate compound represented by the formula (4-1) include 1,3-dimethylimidazolium-2-carboxylate, 1-ethyl-3-methylimidazolium-2-carboxylate, 1-methyl-3-propylimidazolium-2-carboxylate, 1-methyl-3-isopropylimidazolium-2-carboxylate, 1-butyl-3-methylimidazolium-2-carboxylate, 1-tert-butyl-3-methylimidazolium-2-carboxylate, 1-methyl-3-pentylimidazolium-2-carboxylate, 1-hexyl-3-methylimidazolium-2-carboxylate, 1-heptyl-3-methylimidazolium-2-carboxylate, 1-methyl-3-octylimidazolium-2-carboxylate, 1-methyl-3-nonylimidazolium-2-carboxylate, 1-decyl-3-methylimidazolium-2-carboxylate, 1-allyl-3-methylimidazolium-2-carboxylate, 1-benzyl-3-methylimidazolium-2-carboxylate, 1-(2-methoxyethyl)-3-methylimidazolium-2-carboxylate, 1-(2-ethoxyethyl)-3-methylimidazolium-2-carboxylate, 1-(2-dimethylaminoethyl)-3-methylimidazolium-2-carboxylate,
3-methyloxazolium-2-carboxylate, 3,5-dimethyloxazolium-2-carboxylate, 3,4,5-trimethyloxazolium-2-carboxylate,
3-methylthiazolium-2-carboxylate, 3,4-dimethylthiazolium-2-carboxylate, 3,5-dimethylthiazolium-2-carboxylate, 3,4,5-trimethylthiazolium-2-carboxylate, and the like; preferably 1,3-dimethylimidazolium-2-carboxylate, 1-ethyl-3-methylimidazolium-2-carboxylate, l-methyl-3-propylimidazolium-2-carboxylate, 1-butyl-3-methylimidazolium-2-carboxylate, and 1-methyl-3-octylimidazolium-2-carboxylate; and particularly preferably 1,3-dimethylimidazolium-2-carboxylate, 1-butyl-3-methylimidazolium-2-carboxylate, and 1-methyl-3-octylimidazolium-2-carboxylate.

In the formula (4-2), $R^1$, R, $R^9$, X, and a are as defined above. Specific examples of the carboxylate compound represented by the formula (4-2) include 1,3-dimethylimidazolinium-2-carboxylate, 1-ethyl-3-methylimidazolinium-2-carboxylate, 1-methyl-3-propylimidazolinium-2-carboxylate, 1-butyl-3-methylimidazolinium-2-carboxylate, 1-methyl-3-pentylimidazolinium-2-carboxylate, 1-hexyl-3-methylimidazolinium-2-carboxylate, 1-heptyl-3-methylimidazolinium-2-carboxylate, 1-methyl-3-octylimidazolinium-2-carboxylate, 1-methyl-3-nonyl imidazolinium-2-carboxylate, 1-decyl-3-methylimidazolinium-2-carboxylate, 1-allyl-3-methylimidazolinium-2-carboxylate, 1-benzyl-3-methylimidazolinium-2-carboxylate, 1-(2-methoxyethyl)-3-methylimidazolinium-2-carboxylate, 1-(2-ethoxyethyl)-3-methylimidazolinium-2-carboxylate, 1-(2-dimethylaminoethyl)-3-methylimidazolinium-2-carboxylate,
3-methyloxazolinium-2-carboxylate, 3,4-dimethyloxazolinium-2-carboxylate, 3,5-dimethyloxazolinium-2-carboxylate, 3,4,5-trimethyloxazolinium-2-carboxylate,
3-methylthiazolinium-2-carboxylate, 3,4-dimethylthiazolinium-2-carboxylate, 3,5-dimethylthiazolinium-2-carboxylate, 3,4,5-trimethylthiazolinium-2-carboxylate, and the like; preferably 1,3-dimethylimidazolinium-2-carboxylate, l-ethyl-3-methylimidazolinium-2-carboxylate, l-methyl-3-propylimidazolinium-2-carboxylate, 1-butyl-3-methylimidazolinium-2-carboxylate, and 1-octyl-3-methylimidazolinium-2-carboxylate; particularly preferably 1,3-dimethylimidazolinium-2-carboxylate, 1-butyl-3-methylimidazolinium-2-carboxylate, and 1-methyl-3-octylimidazolinium-2-carboxylate.

In the formula (4-3), $R^1$, $R^{10}$, $R^{11}$, $R^{12}$, $R^{13}$, X, and a are as defined above. Specific examples of the carboxylate compound represented by the formula (4-3) include 1,3-dimethylbenzimidazolium-2-carboxylate, l-ethyl-3-methylbenzimidazolium-2-carboxylate, 1-methyl-3-propylbenzimidazolium-2-carboxylate, l-butyl-3-methylbenzimidazolium-2-carboxylate, 1-methyl-3-pentylbenzimidazolium-2-carboxylate, 1-hexyl-3-methylbenzimidazolium-2-carboxylate, 1-heptyl-3-methylbenzimidazolium-2-carboxylate, 1-methyl-3-octylbenzimidazolium-2-carboxylate, 1-methyl-3-nonylbenzimidazolium-2-carboxylate, 1-decyl-3-methylbenzimidazolium-2-carboxylate, 1-allyl-3-methylbenzimidazolium-2-carboxylate, 1-benzyl-3-methylbenzimidazolium-2-carboxylate, 1,3,6-trimethylbenzimidazolium-2-carboxylate, 1-acetyl-3,6-dimethylbenzimidazolium-2-carboxylate, 1,3,6,7-tetramethylbenzimidazolium-2-carboxylate, 1,3-dibenzyl-6,7-dimethylbenzimidazolium-2-carboxylate,
3-methylbenzoxazolium-2-carboxylate,
3-methylbenzothiazolium-2-carboxylate, and the like; preferably 1,3-dimethylbenzimidazolium-2-carboxylate, 1-ethyl-3-methylbenzimidazolium-2-carboxylate, 1-methyl-3-propylbenzimidazolium-2-carboxylate, and 1-butyl-3-methylbenzimidazolium-2-carboxylate; and particularly preferably 1,3-dimethylbenzimidazolium-2-carboxylate.

The amount of dimethyl carbonate used is generally 1 mol or more, and preferably 1 to 6 mol, per mol of the nitrogen-containing organic compound (3).

The optimal reaction temperature in step 1 varies depending on the raw materials, solvents, etc., used, but is generally room temperature or higher, and preferably 20 to 200° C. In the present specification, room temperature generally means about 20° C.

In step 1, a solvent may or may not be used. When a solvent is used, the solvent used is not particularly limited, as long as it does not affect the reaction. Specific examples of solvents include monovalent alcohol solvents, such as methanol, ethanol, propanol, butanol, pentanol, hexanol, 1-methoxy-2-propanol, and ethoxyethanol; polyol solvents, such as ethylene glycol, propylene glycol, and diethylene glycol; glycol monoalkyl ether solvents, such as dipropylene glycol mono-n-butyl ether, dipropylene glycol monomethyl ether, tripropylene glycol monomethyl ether, propylene glycol mono-n-propyl ether, dipropylene glycol mono-n-propyl ether, propylene glycol mono-n-butyl ether, tripropylene glycol mono-n-butyl ether, propylene glycol monomethyl ether, and diethylene glycol monoethyl ether; and the like. Preferable among these are monovalent alcohol solvents, and particularly preferable is methanol. The amount of solvent used is generally 50 parts by weight or less, and preferably 10 parts by weight or less, per part by weight of the nitrogen-containing organic compound (3).

In step 1, the reaction may be performed, if necessary, in an inert gas atmosphere, such as nitrogen, argon, or helium, which do not affect the reaction.

After completion of the reaction, the carboxylate compound (4) can be isolated by concentrating the reaction mixture, and removing the solvent. When an unreacted nitrogen-containing organic compound (3) and dimethyl carbonate remain in the reaction mixture, they can also be removed by concentrating the reaction mixture. Moreover, the reaction mixture can be directly used for the reaction with the isocyanate compound (5) or the urethane compound (6) without removing the carboxylate compound (4) from the reaction mixture. The concentration step is not required, and the production process is more simplified; thus, it is advantageous for industrial production. Accordingly, in the present invention, it is preferable to use the reaction mixture as it is in step 2 or step 2'.

Next, step 2 is explained.

In the formula (5), A and n are as defined above. The isocyanate compound (5) is preferably an isocyanate compound represented by the following formula (5-1), (5-2), or (5-3); and particularly preferably an isocyanate compound represented by the formula (5-1) or (5-2).

Formula (5-1):

$R^4$—NCO (5-1)

wherein $R^4$ is as defined above.

Formula (5-2):

OCN—$R^5$—NCO (5-2)

wherein $R^5$ is as defined above.

Formula (5-3)

(5-3)

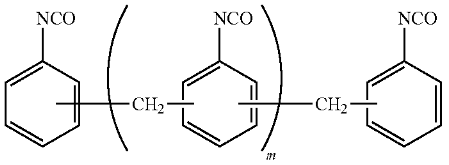

wherein m is as defined above.

In the formula (5-1), $R^4$ is as defined above.

In the formula (5-2), $R^5$ is as defined above.

In the formula (5-3), m is as defined above.

Although specific examples of the isocyanate compound (5) are shown below, the present invention is not limited thereto. In the following specific examples, Et represents an ethyl group, Pr represents a n-propyl group, and Bu represents a n-butyl group.

(5-1-1)

$H_3C$—NCO (5-1-2)

Et—NCO (5-1-3)

Pr—NCO (5-1-4)

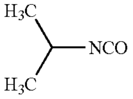

(5-1-5)

Bu—NCO (5-1-6)

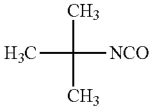

(5-1-7)

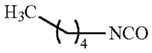

(5-1-8)

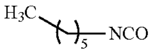

(5-1-9)

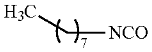

(5-1-10)

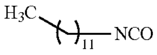

(5-1-11)

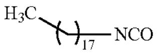

(5-1-12)

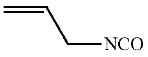

(5-1-13)

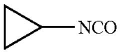

(5-1-14)

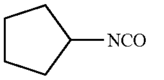

(5-1-15)

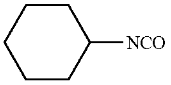

(5-1-16)

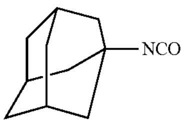

(5-1-17)

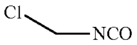

(5-1-18)

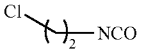

(5-1-19)

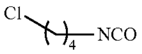

-continued

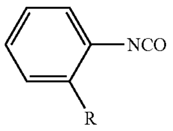

| | | |
|---|---|---|
| R = | H | (5-1-20) |
| | $CH_3$ | (5-1-21) |
| | $(CH_2)_3CH_3$ | (5-1-22) |
| | $(CH_2)_7CH_3$ | (5-1-23) |
| | $OCH_3$ | (5-1-24) |
| | $OCH_2CH_3$ | (5-1-25) |
| | $CH(CH_3)_2$ | (5-1-26) |
| | $C(CH_3)_3$ | (5-1-27) |
| | $N(CH_3)_2$ | (5-1-28) |
| | F | (5-1-29) |
| | Cl | (5-1-30) |
| | Br | (5-1-31) |

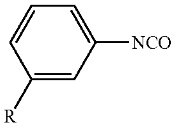

| | | |
|---|---|---|
| R = | $CH_3$ | (5-1-32) |
| | $(CH_2)_3CH_3$ | (5-1-33) |
| | $(CH_2)_7CH_3$ | (5-1-34) |
| | $OCH_3$ | (5-1-35) |
| | $OCH_2CH_3$ | (5-1-36) |
| | $CH(CH_3)_2$ | (5-1-37) |
| | $C(CH_3)_3$ | (5-1-38) |
| | $N(CH_3)_2$ | (5-1-39) |
| | F | (5-1-40) |
| | Cl | (5-1-41) |
| | Br | (5-1-42) |

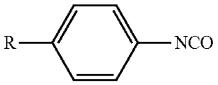

| | | |
|---|---|---|
| R = | $CH_3$ | (5-1-43) |
| | $(CH_2)_3CH_3$ | (5-1-44) |
| | $(CH_2)_7CH_3$ | (5-1-45) |
| | $OCH_3$ | (5-1-46) |
| | $OCH_2CH_3$ | (5-1-47) |
| | $CH(CH_3)_2$ | (5-1-48) |
| | $C(CH_3)_3$ | (5-1-49) |
| | $N(CH_3)_2$ | (5-1-50) |
| | F | (5-1-51) |
| | Cl | (5-1-52) |
| | Br | (5-1-53) |

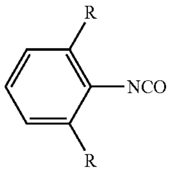

| | | |
|---|---|---|
| R = | $CH_3$ | (5-1-54) |
| | $(CH_2)_3CH_3$ | (5-1-55) |
| | $(CH_2)_7CH_3$ | (5-1-56) |
| | $OCH_3$ | (5-1-57) |
| | $OCH_2CH_3$ | (5-1-58) |
| | $CH(CH_3)_2$ | (5-1-59) |
| | $C(CH_3)_3$ | (5-1-60) |
| | $N(CH_3)_2$ | (5-1-61) |
| | F | (5-1-62) |
| | Cl | (5-1-63) |
| | Br | (5-1-64) |

-continued

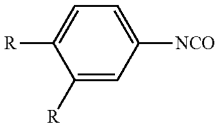

| | | |
|---|---|---|
| R = | $CH_3$ | (5-1-65) |
| | $(CH_2)_3CH_3$ | (5-1-66) |
| | $(CH_2)_7CH_3$ | (5-1-67) |
| | $OCH_3$ | (5-1-68) |
| | $OCH_2CH_3$ | (5-1-69) |
| | $CH(CH_3)_2$ | (5-1-70) |
| | $C(CH_3)_3$ | (5-1-71) |
| | $N(CH_3)_2$ | (5-1-72) |
| | F | (5-1-73) |
| | Cl | (5-1-74) |
| | Br | (5-1-75) |

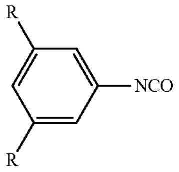

| | | |
|---|---|---|
| R = | $CH_3$ | (5-1-76) |
| | $(CH_2)_3CH_3$ | (5-1-77) |
| | $(CH_2)_7CH_3$ | (5-1-78) |
| | $OCH_3$ | (5-1-79) |
| | $OCH_2CH_3$ | (5-1-80) |
| | $CH(CH_3)_2$ | (5-1-81) |
| | $C(CH_3)_3$ | (5-1-82) |
| | $N(CH_3)_2$ | (5-1-83) |
| | F | (5-1-84) |
| | Cl | (5-1-85) |
| | Br | (5-1-86) |

(5-1-87)

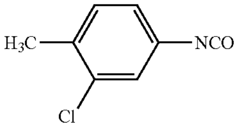

(5-1-88)

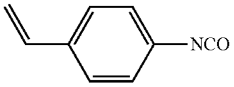

(5-1-89)

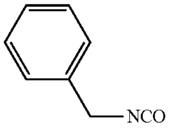

(5-1-90)

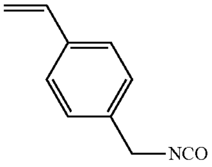

OCN—R—NCO

| | | |
|---|---|---|
| R = | $—CH_2—$ | (5-2-1) |
| | $—CH_2CH_2—$ | (5-2-2) |
| | $—CH_2(CH_2)_2CH_2—$ | (5-2-3) |
| | $—CH_2(CH_2)_4CH_2—$ | (5-2-4) |
| | $—CH_2(CH_2)_6CH_2—$ | (5-2-5) |
| | $—CH_2(CH_2)_8CH_2—$ | (5-2-6) |
| | $—CH_2(CH_2)_{10}CH_2—$ | (5-2-7) |

-continued (5-2-8)

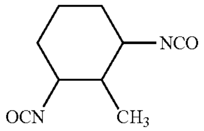

(5-2-9)

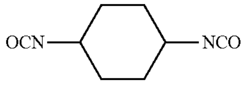

(5-2-10)

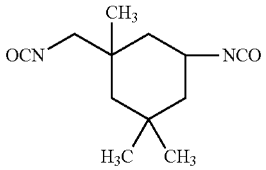

(5-2-11)

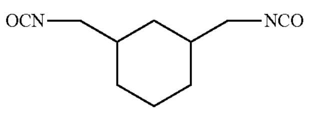

(5-2-12)

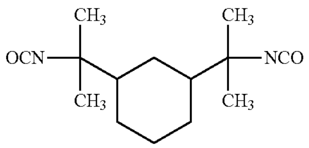

(5-2-13)

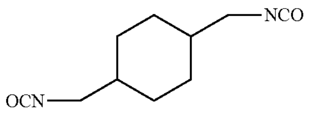

(5-2-14)

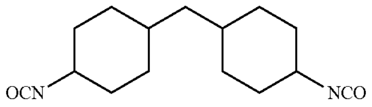

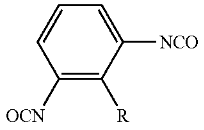

R = H (5-2-15)
$CH_3$ (5-2-16)

(5-2-17)

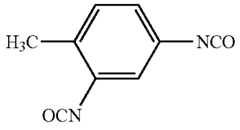

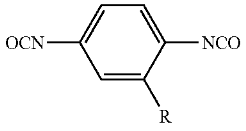

R = H (5-2-18)
$CH_3$ (5-2-19)

(5-2-20)

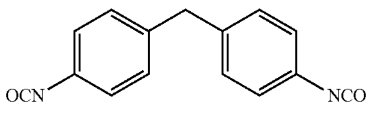

-continued (5-2-21)

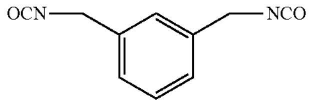

(5-2-22)

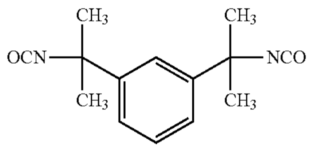

The isocyanate compound (5) is preferably a compound represented by the formula (5-1-5), (5-1-20), (5-1-52), or (5-2-17).

In step 2, the carboxylate compound (4) is generally reacted in an amount of 0.8 mol or more, and preferably 1 to 3 mol, per mol of isocyanate groups contained in the isocyanate compound (5).

In step 2, a solvent may or may not be used. When a solvent is used, a hydrocarbon solvent is suitably used. Examples of hydrocarbon solvents include aromatic hydrocarbon solvents, such as toluene, benzene, and xylene; aliphatic or alicyclic hydrocarbon solvents, such as methylcyclohexane, cyclohexane, n-hexane, n-heptane, and octane; halogenated aliphatic hydrocarbon solvents, such as dichloromethane and chloroform; halogenated aromatic hydrocarbon solvents, such as chlorobenzene and dichlorobenzene; and the like. Preferable among these are aromatic hydrocarbon solvents and halogenated aromatic hydrocarbon solvents; and particularly preferable are toluene, xylene, and chlorobenzene. The solvents can be used as a mixture of two or more, if necessary.

When a reaction mixture obtained by the reaction of the nitrogen-containing organic compound (3) and dimethyl carbonate is used as the carboxylate compound (4), the solvent in the reaction mixture can be directly used as a solvent for the reaction of the isocyanate compound (5) and the carboxylate compound (4). In this case, the reaction may be performed while adding a solvent, if necessary.

When a solvent is used, the amount of solvent used is generally 50 parts by weight or less, and preferably 0.1 parts by weight or more and 35 parts by weight or less, per part by weight of the carboxylate compound (4).

The reaction temperature is not particularly limited, but may be equal to or less than the boiling point of the solvent. The reaction temperature is generally 10° C. or more, preferably 40 to 200° C., and particularly preferably 80 to 150° C.

The reaction of the isocyanate compound (5) and the carboxylate compound (4) may be performed, if necessary, in an inert gas atmosphere, such as nitrogen, argon, or helium, which do not affect the reaction.

After completion of the reaction, the solvent can be removed by concentration or filtration of the reaction mixture to thereby obtain an amidate compound (1). Moreover, the obtained amidate compound (1) can be purified by a method, such as recrystallization.

Step 2' is explained.

In the formula (6), A and n are as defined above. $R^{14}$ is a hydrocarbon group that may contain a heteroatom, preferably a $C_1$-$C_{50}$ hydrocarbon group that may contain a heteroatom, more preferably a $C_1$-$C_{30}$ hydrocarbon group, and particularly preferably a $C_1$-$C_8$ hydrocarbon group. Examples of the hydrocarbon group that may contain a heteroatom include a methyl group, an ethyl group, a propyl group, an isopropyl group, a n-butyl group, a s-butyl group, a t-butyl group, a n-pentyl group, a n-hexyl group, a n-octyl group, a n-decyl group, a n-dodecyl group, an allyl group, a benzyl group, a cyclohexyl group, an adamantyl group, a phenyl group, a 2,6-diisopropylphenyl group, a 2,4,6-trimethylphenyl group, a 2-methoxyethyl group, a 2-ethoxyethyl group, a 2-(dimethylamino)ethyl group, and the like; preferably a methyl group, an ethyl group, a propyl group, an isopropyl group, a t-butyl group, a n-octyl group, a cyclopentyl group, a cyclohexyl group, and a 2,4,6-trimethylphenyl group; more preferably a methyl group, an ethyl group, an isopropyl group, a t-butyl group, a n-octyl group, and a phenyl group; and particularly preferably a methyl group, an isopropyl group, a t-butyl group, a n-octyl group, and a phenyl group.

In the present invention, the urethane compound represented by the formula (6) (hereinafter referred to as the "urethane compound (6)") is preferably a urethane compound represented by the following formula (6-1), (6-2), or (6-3); and particularly preferably a urethane compound represented by the formula (6-1) or (6-2).

Formula (6-1)

(6-1)

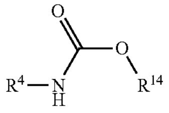

wherein $R^4$ and $R^{14}$ are as defined above.

Formula (6-2)

(6-2)

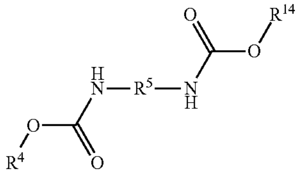

wherein $R^5$ and $R^{14}$ are as defined above.

Formula (6-3)

(6-3)

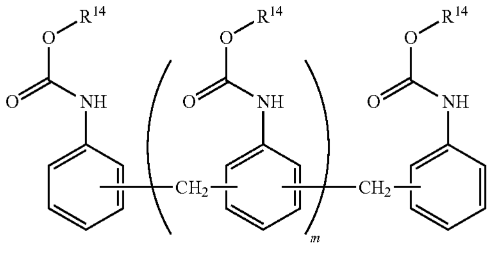

wherein $R^{14}$ is as defined above.

In the formula (6-1), $R^4$ is as defined above.

In the formula (6-2), $R^5$ is as defined above.

In the formula (6-3), m is as defined above.

Although specific examples of the urethane compound (6) are shown below, the present invention is not limited thereto. In the following specific examples, Et represents an ethyl group, Pr represents a n-propyl group, and Bu represents a n-butyl group.

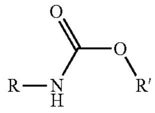

| R | R' | |
|---|---|---|
| $CH_3$ | $CH_3$ | (6-1-1p) |
| Et | $CH_3$ | (6-1-2p) |
| Pr | $CH_3$ | (6-1-3p) |
| $CH(CH_3)_2$ | $CH_3$ | (6-1-4p) |
| Bu | $CH_3$ | (6-1-5p) |
| $C(CH_3)_3$ | $CH_3$ | (6-1-6p) |
| $(CH_2)_4CH_3$ | $CH_3$ | (6-1-7p) |
| $(CH_2)_5CH_3$ | $CH_3$ | (6-1-8p) |
| $(CH_2)_7CH_3$ | $CH_3$ | (6-1-9p) |
| $(CH_2)_{11}CH_3$ | $CH_3$ | (6-1-10p) |
| $(CH_2)_{17}CH_3$ | $CH_3$ | (6-1-11p) |
| 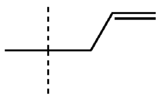 | $CH_3$ | (6-1-12p) |
| 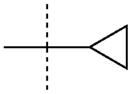 | $CH_3$ | (6-1-13p) |
| 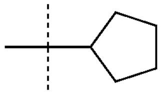 | $CH_3$ | (6-1-14p) |
| 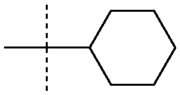 | $CH_3$ | (6-1-15p) |
| 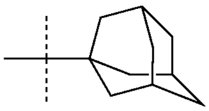 | $CH_3$ | (6-1-16p) |
| 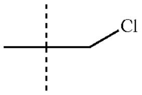 | $CH_3$ | (6-1-17p) |
| 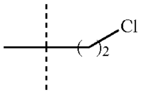 | $CH_3$ | (6-1-18p) |
| 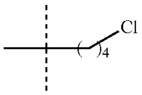 | $CH_3$ | (6-1-19p) |
| $CH_3$ | $CH(CH_3)_2$ | (6-1-1q) |
| Et | $CH(CH_3)_2$ | (6-1-2q) |
| Pr | $CH(CH_3)_2$ | (6-1-3q) |
| $CH(CH_3)_2$ | $CH(CH_3)_2$ | (6-1-4q) |
| Bu | $CH(CH_3)_2$ | (6-1-5q) |
| $C(CH_3)_3$ | $CH(CH_3)_2$ | (6-1-6q) |
| $(CH_2)_4CH_3$ | $CH(CH_3)_2$ | (6-1-7q) |
| $(CH_2)_5CH_3$ | $CH(CH_3)_2$ | (6-1-8q) |
| $(CH_2)_7CH_3$ | $CH(CH_3)_2$ | (6-1-9q) |
| $(CH_2)_{11}CH_3$ | $CH(CH_3)_2$ | (6-1-10q) |

-continued

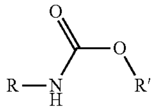

| R | R' | |
|---|---|---|
| $(CH_2)_{17}CH_3$ | $CH(CH_3)_2$ | (6-1-11q) |
| 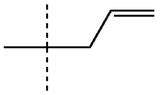 | $CH(CH_3)_2$ | (6-1-12q) |
| 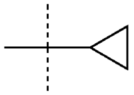 | $CH(CH_3)_2)$ | (6-1-13q |
| 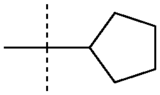 | $CH(CH_3)_2$ | (6-1-14q) |
| 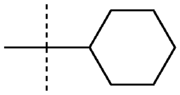 | $CH(CH_3)_2$ | (6-1-15q) |
| 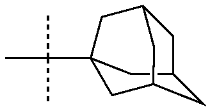 | $CH(CH_3)_2$ | (6-1-16q) |
| 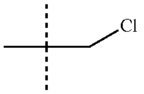 | $CH(CH_3)_2$ | (6-1-17q) |
| 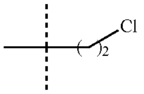 | $CH(CH_3)_2$ | (6-1-18q) |
| 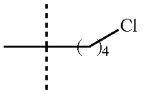 | $CH(CH_3)_2$ | (6-1-19q) |
| $CH_3$ | $C(CH_3)_3$ | (6-1-1r) |
| Et | $C(CH_3)_3$ | (6-1-2r) |
| Pr | $C(CH_3)_3$ | (6-1-3r) |
| $CH(CH_3)_2$ | $C(CH_3)_3$ | (6-1-4r) |
| Bu | $C(CH_3)_3$ | (6-1-5r) |
| $C(CH_3)_3$ | $C(CH_3)_3$ | (6-1-6r) |
| $(CH_2)_4CH_3$ | $C(CH_3)_3$ | (6-1-7r) |
| $(CH_2)_5CH_3$ | $C(CH_3)_3$ | (6-1-8r) |
| $(CH_2)_7CH_3$ | $C(CH_3)_3$ | (6-1-9r) |
| $(CH_2)_{11}CH_3$ | $C(CH_3)_3$ | (6-1-10r) |
| $(CH_2)_{17}CH_3$ | $C(CH_3)_3$ | (6-1-11r) |
| 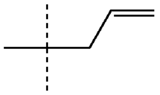 | $C(CH_3)_3$ | (6-1-12r) |
| 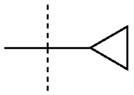 | $C(CH_3)_3$ | (6-1-13r) |

-continued

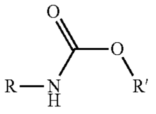

| R | R' | |
|---|---|---|
| 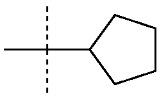 | $C(CH_3)_3$ | (6-1-14r) |
| 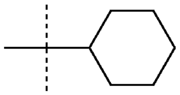 | $C(CH_3)_3$ | (6-1-15r) |
| 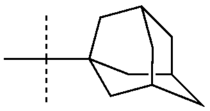 | $C(CH_3)_3$ | (6-1-16r) |
| 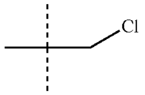 | $C(CH_3)_3$ | (6-1-17r) |
| 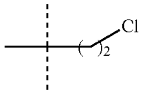 | $C(CH_3)_3$ | (6-1-18r) |
| 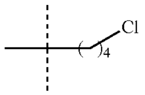 | $C(CH_3)_3$ | (6-1-19r) |

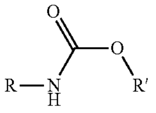

| R | R' | |
|---|---|---|
| $CH_3$ | $(CH_2)_7CH_3$ | (6-1-1s) |
| Et | $(CH_2)_7CH_3$ | (6-1-2s) |
| Pr | $(CH_2)_7CH_3$ | (6-1-3s) |
| $CH(CH_3)_2$ | $(CH_2)_7CH_3$ | (6-1-4s) |
| Bu | $(CH_2)_7CH_3$ | (6-1-5s) |
| $C(CH_3)_3$ | $(CH_2)_7CH_3$ | (6-1-6s) |
| $(CH_2)_4CH_2$ | $(CH_2)_7CH_3$ | (6-1-7s) |
| $(CH_2)_5CH_3$ | $(CH_2)_7CH_3$ | (6-1-8s) |
| $(CH_2)_7CH_3$ | $(CH_2)_7CH_3$ | (6-1-9s) |
| $(CH_2)_{11}CH_3$ | $(CH_2)_7CH_3$ | (6-1-10s) |
| $(CH_2)_{17}CH_3$ | $(CH_2)_7CH_3$ | (6-1-11s) |
| 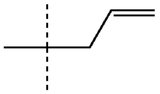 | $(CH_2)_7CH_3$ | (6-1-12s) |
| 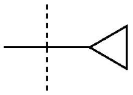 | $(CH_2)_7CH_3$ | (6-1-13s) |
| 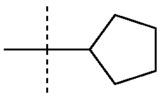 | $(CH_2)_7CH_3$ | (6-1-14s) |

-continued

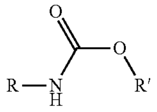

| R | R' | |
|---|---|---|
| 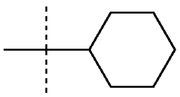 | $(CH_2)_7CH_3$ | (6-1-15s) |
| 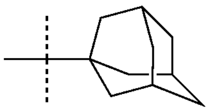 | $(CH_2)_7CH_3$ | (6-1-16s) |
| 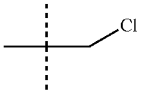 | $(CH_2)_7CH_3$ | (6-1-17s) |
| 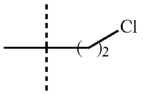 | $(CH_2)_7CH_3$ | (6-1-18s) |
| 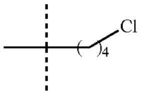 | $(CH_2)_7CH_3$ | (6-1-19s) |
| $CH_3$ | Ph | (6-1-1t) |
| Et | Ph | (6-1-2t) |
| Pr | Ph | (6-1-3t) |
| $CH(CH_3)_2$ | Ph | (6-1-4t) |
| Bu | Ph | (6-1-5t) |
| $C(CH_3)_3$ | Ph | (6-1-6t) |
| $(CH_2)_4CH_3$ | Ph | (6-1-7t) |
| $(CH_2)_5CH_3$ | Ph | (6-1-8t) |
| $(CH_2)_7CH_3$ | Ph | (6-1-9t) |
| $(CH_2)_{11}CH_3$ | Ph | (6-1-10t) |
| $(CH_2)_{17}CH_3$ | Ph | (6-1-11t) |
| 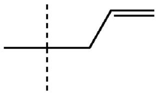 | Ph | (6-1-12t) |
| 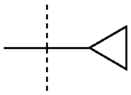 | Ph | (6-1-13t) |
| 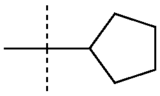 | Ph | (6-1-14t) |
| 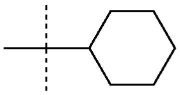 | Ph | (6-1-15t) |
| 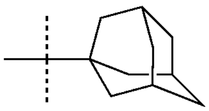 | Ph | (6-1-16t) |

-continued

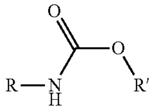

| R | R' | |
|---|---|---|
| 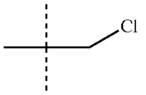 | Ph | (6-1-17t) |
| 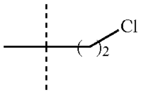 | Ph | (6-1-18t) |
| 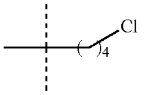 | Ph | (6-1-19t) |

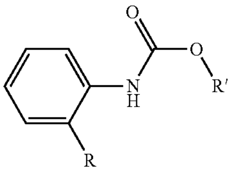

| R | R' | |
|---|---|---|
| H | $CH_3$ | (6-1-20p) |
| $CH_3$ | $CH_3$ | (6-1-21p) |
| $(CH_2)_3CH_3$ | $CH_3$ | (6-1-22p) |
| $(CH_2)_7CH_3$ | $CH_3$ | (6-1-23p) |
| $OCH_3$ | $CH_3$ | (6-1-24p) |
| $OCH_2CH_3$ | $CH_3$ | (6-1-25p) |
| $CH(CH_3)_2$ | $CH_3$ | (6-1-26p) |
| $C(CH_3)_3$ | $CH_3$ | (6-1-27p) |
| $N(CH_3)_2$ | $CH_3$ | (6-1-28p) |
| F | $CH_3$ | (6-1-29p) |
| Cl | $CH_3$ | (6-1-30p) |
| Br | $CH_3$ | (6-1-31p) |
| H | $CH(CH_3)_2$ | (6-1-20q) |
| $CH_3$ | $CH(CH_3)_2$ | (6-1-21q) |
| $(CH_2)_3CH_3$ | $CH(CH_3)_2$ | (6-1-22q) |
| $(CH_2)_7CH_3$ | $CH(CH_3)_2$ | (6-1-23q) |
| $OCH_3$ | $CH(CH_3)_2$ | (9-1-24q) |
| $OCH_2CH_3$ | $CH(CH_3)_2$ | (6-1-25q) |
| $CH(CH_3)_2$ | $CH(CH_3)_2$ | (6-1-26q) |
| $C(CH_3)_3$ | $CH(CH_3)_2$ | (6-1-27q) |
| $N(CH_3)_2$ | $CH(CH_3)_2$ | (6-1-28q) |
| F | $CH(CH_3)_2$ | (6-1-29q) |
| Cl | $CH(CH_3)_2$ | (6-1-30q) |
| Br | $CH(CH_3)_2$ | (6-1-31q) |
| H | $C(CH_3)_3$ | (6-1-20r) |
| $CH_3$ | $C(CH_3)_3$ | (6-1-21r) |
| $(CH_2)_3CH_3$ | $C(CH_3)_3$ | (6-1-22r) |
| $(CH_2)_7CH_3$ | $C(CH_3)_3$ | (6-1-23r) |
| $OCH_3$ | $C(CH_3)_3$ | (6-1-24r) |
| $OCH_2CH_3$ | $C(CH_3)_3$ | (6-1-25r) |
| $CH(CH_3)_2$ | $C(CH_3)_3$ | (6-1-26r) |
| $C(CH_3)_3$ | $C(CH_3)_3$ | (6-1-27r) |
| $N(CH_3)_2$ | $C(CH_3)_3$ | (6-1-28r) |
| F | $C(CH_3)_3$ | (6-1-29r) |
| Cl | $C(CH_3)_3$ | (6-1-30r) |
| Br | $C(CH_3)_3$ | (6-1-31r) |
| H | $(CH_2)_7CH_3$ | (6-1-20s) |
| $CH_3$ | $(CH_2)_7CH_3$ | (6-1-21s) |
| $(CH_2)_3CH_3$ | $(CH_2)_7CH_3$ | (6-1-22s) |
| $(CH_2)_7CH_3$ | $(CH_2)_7CH_3$ | (6-1-23s) |
| $OCH_3$ | $(CH_2)_7CH_3$ | (6-1-24s) |

-continued

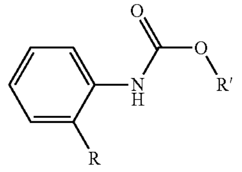

| R | R' | |
|---|---|---|
| $OCH_2CH_3$ | $(CH_2)_7CH_3$ | (6-1-25s) |
| $CH(CH_3)_2$ | $(CH_2)_7CH_3$ | (6-1-26s) |
| $C(CH_3)_3$ | $(CH_2)_7CH_3$ | (6-1-27s) |
| $N(CH_3)_2$ | $(CH_2)_7CH_3$ | (6-1-28s) |
| F | $(CH_2)_7CH_3$ | (6-1-29s) |
| Cl | $(CH_3)_7CH_3$ | (6-1-30s) |
| Br | $(CH_3)_7CH_3$ | (6-1-31s) |
| H | Ph | (6-1-20t) |
| $CH_3$ | Ph | (6-1-21t) |
| $(CH_2)_3CH_3$ | Ph | (6-1-22t) |
| $(CH_2)_7CH_3$ | Ph | (6-1-23t) |
| $OCH_3$ | Ph | (6-1-24t) |
| $OCH_2CH_3$ | Ph | (6-1-25t) |
| $CH(CH_3)_2$ | Ph | (6-1-26t) |
| $C(CH_3)_3$ | Ph | (6-1-27t) |
| $N(CH)_2$ | Ph | (6-1-28t) |
| F | Ph | (6-1-29t) |
| Cl | Ph | (6-1-30t) |
| Br | Ph | (6-1-31t) |

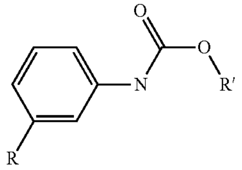

| R | R' | |
|---|---|---|
| $CH_3$ | $CH_3$ | (6-1-32p) |
| $(CH_2)_3CH_3$ | $CH_3$ | (6-1-33p) |
| $(CH_2)_7CH_3$ | $CH_3$ | (6-1-34p) |
| $OCH_3$ | $CH_3$ | (6-1-35p) |
| $OCH_2CH_3$ | $CH_3$ | (6-1-36p) |
| $CH(CH_3)_2$ | $CH_3$ | (6-1-37p) |
| $C(CH_3)_3$ | $CH_3$ | (6-1-38p) |
| $N(CH_3)_2$ | $CH_3$ | (6-1-39p) |
| F | $CH_3$ | (6-1-40p) |
| Cl | $CH_3$ | (6-1-41p) |
| Br | $CH_3$ | (6-1-42p) |
| $CH_3$ | $CH(CH_3)_2$ | (6-1-32q) |
| $(CH_2)_3CH_3$ | $CH(CH_3)_2$ | (6-1-33q) |
| $(CH_2)_7CH_3$ | $CH(CH_3)_2$ | (6-1-34q) |
| $OCH_3$ | $CH(CH_3)_2$ | (6-1-35q) |
| $OCH_2CH_3$ | $CH(CH_3)_2$ | (6-1-36q) |
| $CH(CH_3)_2$ | $CH(CH_3)_2$ | (6-1-37q) |
| $C(CH_3)_3$ | $CH(CH_3)_2$ | (6-1-38q) |
| $N(CH_3)_2$ | $CH(CH_3)_2$ | (6-1-39q) |
| F | $CH(CH_3)_2$ | (6-1-40q) |
| Cl | $CH(CH_3)_2$ | (6-1-41q) |
| Br | $CH(CH_3)_2$ | (6-1-42q) |
| $CH_3$ | $C(CH_3)_3$ | (6-1-32r) |
| $(CH_2)_3CH_3$ | $C(CH_3)_3$ | (6-4-33r) |
| $(CH_2)_7CH_3$ | $C(CH_3)_3$ | (6-1-34r) |
| $OCH_3$ | $C(CH_3)_2$ | (6-1-35r) |
| $OCH_2CH_3$ | $C(CH_3)_2$ | (6-1-36r) |
| $CH(CH_3)_2$ | $C(CH_3)_2$ | (6-1-37r) |
| $C(CH_3)_3$ | $C(CH_3)_2$ | (6-1-38r) |
| $N(CH_3)_2$ | $C(CH_3)_2$ | (6-1-39r) |
| F | $C(CH_3)_2$ | (6-1-40r) |
| Cl | $C(CH_3)_2$ | (6-1-41r) |
| Br | $C(CH_3)_2$ | (6-1-42r) |
| $CH_3$ | $(CH_2)_7CH_3$ | (6-1-32s) |

-continued

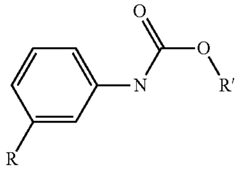

| R | R' | |
|---|---|---|
| $(CH_2)_3CH_3$ | $(CH_2)_7CH_3$ | (6-1-33s) |
| $(CH_2)_7CH_3$ | $(CH_2)_7CH_3$ | (6-1-34s) |
| $OCH_3$ | $(CH_2)_7CH_3$ | (6-1-35s) |
| $OCH_2CH_3$ | $(CH_2)_7CH_3$ | (6-1-36s) |
| $CH(CH_3)_2$ | $(CH_2)_7CH_3$ | (6-1-37s) |
| $C(CH_3)_3$ | $(CH_2)_7CH_3$ | (6-1-38s) |
| $N(CH_3)_2$ | $(CH_2)_7CH_3$ | (6-1-39s) |
| F | $(CH_2)_7CH_3$ | (6-1-40s) |
| Cl | $(CH_2)_7CH_3$ | (6-1-41s) |
| Br | $(CH_2)_7CH_3$ | (6-1-42s) |
| $CH_3$ | Ph | (6-1-32t) |
| $(CH_2)_3CH_3$ | Ph | (6-1-33t) |
| $(CH_2)_7CH_3$ | Ph | (6-1-34t) |
| $OCH_3$ | Ph | (6-1-35t) |
| $OCH_2CH_3$ | Ph | (6-1-36t) |
| $CH(CH_3)_2$ | Ph | (6-1-37t) |
| $C(CH_3)_3$ | Ph | (6-1-38t) |
| $N(CH_3)_2$ | Ph | (6-1-39t) |
| F | Ph | (6-1-40t) |
| Cl | Ph | (6-1-41t) |
| Br | Ph | (6-1-42t) |

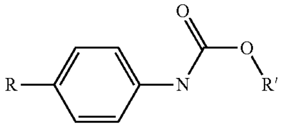

| R | R' | |
|---|---|---|
| $CH_3$ | $CH_3$ | (6-1-43p) |
| $(CH_2)_3CH_3$ | $CH_3$ | (6-1-44p) |
| $(CH_2)_7CH_3$ | $CH_3$ | (6-1-45p) |
| $OCH_3$ | $CH_3$ | (6-1-46p) |
| $OCH_2CH_3$ | $CH_3$ | (6-1-47p) |
| $CH(CH_3)_2$ | $CH_3$ | (6-1-48p) |
| $C(CH_3)_3$ | $CH_3$ | (6-1-49p) |
| $N(CH_3)_2$ | $CH_3$ | (6-1-50p) |
| F | $CH_3$ | (6-1-51p) |
| Cl | $CH_3$ | (6-1-52p) |
| Br | $CH_3$ | (6-1-53p) |
| $CH_3$ | $CH(CH_3)_2$ | (6-1-43q) |
| $(CH_2)_3CH_3$ | $CH(CH_3)_2$ | (6-1-44q) |
| $(CH_2)_7CH_3$ | $CH(CH_3)_2$ | (6-1-45q) |
| $OCH_3$ | $CH(CH_3)_2$ | (6-1-46q) |
| $OCH_2CH_3$ | $CH(CH_3)_2$ | (6-1-47q) |
| $CH(CH_3)_2$ | $CH(CH_3)_2$ | (6-1-48q) |
| $C(CH_3)_3$ | $CH(CH_3)_2$ | (6-1-49q) |
| $N(CH_3)_2$ | $CH(CH_3)_2$ | (6-1-50q) |
| F | $CH(CH_3)_2$ | (6-1-51q) |
| Cl | $CH(CH_3)_2$ | (6-1-52q) |
| Br | $CH(CH_3)_2$ | (6-1-53q) |
| $CH_3$ | $C(CH_3)_3$ | (6-1-43r) |
| $(CH_2)_3CH_3$ | $C(CH_3)_3$ | (6-1-44r) |
| $(CH_2)_7CH_3$ | $C(CH_3)_3$ | (6-1-45r) |
| $OCH_3$ | $C(CH_3)_3$ | (6-1-46r) |
| $OCH_2CH_3$ | $C(CH_3)_3$ | (6-1-47r) |
| $CH(CH_3)_2$ | $C(CH_3)_3$ | (6-1-48r) |
| $C(CH_3)_3$ | $C(CH_3)_3$ | (6-1-49r) |
| $N(CH_3)_2$ | $C(CH_3)_3$ | (6-1-50r) |
| F | $C(CH_3)_3$ | (6-1-51r) |
| Cl | $C(CH_3)_3$ | (6-1-52r) |
| Br | $C(CH_3)_3$ | (6-1-53r) |
| $CH_3$ | $(CH_2)_7CH_3$ | (6-1-43s) |

-continued

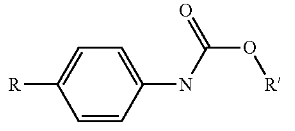

| R | R' | |
|---|---|---|
| $(CH_2)_3CH_3$ | $(CH_2)_7CH_3$ | (6-1-44s) |
| $(CH_2)_7CH_3$ | $(CH_2)_7CH_3$ | (6-1-45s) |
| $OCH_3$ | $(CH_2)_7CH_3$ | (6-1-46s) |
| $OCH_2CH_3$ | $(CH_2)_7CH_3$ | (6-1-47s) |
| $CH(CH_3)_2$ | $(CH_2)_7CH_3$ | (6-1-48s) |
| $C(CH_3)_3$ | $(CH_2)_7CH_3$ | (6-1-49s) |
| $N(CH_3)_2$ | $(CH_2)_7CH_3$ | (6-1-50s) |
| F | $(CH_2)_7CH_3$ | (6-1-51s) |
| Cl | $(CH_2)_7CH_3$ | (6-1-52s) |
| Br | $(CH_2)_7CH_3$ | (6-1-53s) |
| $CH_3$ | Ph | (6-1-43t) |
| $(CH_2)_3CH_3$ | Ph | (6-1-44t) |
| $(CH_2)_7CH_3$ | Ph | (6-1-45t) |
| $OCH_3$ | Ph | (6-1-46t) |
| $OCH_2CH_3$ | Ph | (6-1-47t) |
| $CH(CH_3)_2$ | Ph | (6-1-48t) |
| $C(CH_3)_3$ | Ph | (6-1-49t) |
| $N(CH_3)_2$ | Ph | (6-1-50t) |
| F | Ph | (6-1-51t) |
| Cl | Ph | (6-1-52t) |
| Br | Ph | (6-1-53t) |

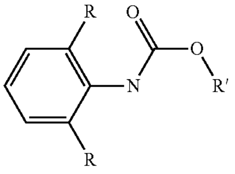

| R | R' | |
|---|---|---|
| $CH_3$ | $CH_3$ | (6-1-54p) |
| $(CH_2)_3CH_3$ | $CH_3$ | (6-1-55p) |
| $(CH_2)_7CH_3$ | $CH_3$ | (6-1-56p) |
| $OCH_3$ | $CH_3$ | (6-1-57p) |
| $OCH_2CH_3$ | $CH_3$ | (6-1-58p) |
| $CH(CH_3)_2$ | $CH_3$ | (6-1-59p) |
| $C(CH_3)_3$ | $CH_3$ | (6-1-60p) |
| $N(CH_3)_2$ | $CH_3$ | (6-1-61p) |
| F | $CH_3$ | (6-1-62p) |
| Cl | $CH_3$ | (6-1-63p) |
| Br | $CH_3$ | (6-1-64p) |
| $CH_3$ | $CH(CH_3)_2$ | (6-1-54q) |
| $(CH_2)_3CH_3$ | $CH(CH_3)_2$ | (6-1-55q) |
| $(CH_2)_7CH_3$ | $CH(CH_3)_2$ | (6-1-56q) |
| $OCH_3$ | $CH(CH_3)_2$ | (6-1-57q) |
| $OCH_2CH_3$ | $CH(CH_3)_2$ | (6-1-58q) |
| $CH(CH_3)_2$ | $CH(CH_3)_2$ | (6-1-59q) |
| $C(CH_3)_3$ | $CH(CH_3)_2$ | (6-1-60q) |
| $N(CH_3)_2$ | $CH(CH_3)_2$ | (6-1-61q) |
| F | $CH(CH_3)_2$ | (6-1-62q) |
| Cl | $CH(CH_3)_2$ | (6-1-63q) |
| Br | $CH(CH_3)_2$ | (6-1-64q) |
| $CH_3$ | $C(CH_3)_3$ | (6-1-54r) |
| $(CH_2)_3CH_3$ | $C(CH_3)_3$ | (6-1-55r) |
| $(CH_2)_7CH_3$ | $C(CH_3)_3$ | (6-1-56r) |
| $OCH_3$ | $C(CH_3)_3$ | (6-1-57r) |
| $OCH_2CH_3$ | $C(CH_3)_3$ | (6-1-58r) |
| $CH(CH_3)_2$ | $C(CH_3)_3$ | (6-1-59r) |
| $C(CH_3)_3$ | $C(CH_3)_3$ | (6-1-60r) |
| $N(CH_3)_2$ | $C(CH_3)_3$ | (6-1-61r) |
| F | $C(CH_3)_3$ | (6-1-62r) |
| Cl | $C(CH_3)_3$ | (6-1-63r) |
| Br | $C(CH_3)_3$ | (6-1-64r) |
| $CH_3$ | $(CH_2)_7CH_3$ | (6-1-54s) |

-continued

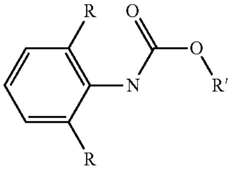

| R | R' | |
|---|---|---|
| $(CH_2)_3CH_3$ | $(CH_2)_7CH_3$ | (6-1-55s) |
| $(CH_2)_7CH_3$ | $(CH_2)_7CH_3$ | (6-1-56s) |
| $OCH_3$ | $(CH_2)_7CH_3$ | (6-1-57s) |
| $OCH_2CH_3$ | $(CH_2)_7CH_3$ | (6-1-58s) |
| $CH(CH_3)_2$ | $(CH_2)_7CH_3$ | (6-1-59s) |
| $C(CH_3)_3$ | $(CH_2)_7CH_3$ | (6-1-60s) |
| $N(CH_3)_2$ | $(CH_2)_7CH_3$ | (6-1-61s) |
| F | $(CH_2)_7CH_3$ | (6-1-62s) |
| Cl | $(CH_2)_7CH_3$ | (6-1-63s) |
| Br | $(CH_2)_7CH_3$ | (6-1-64s) |
| $CH_3$ | Ph | (6-1-54t) |
| $(CH_2)_3CH_3$ | Ph | (6-1-55t) |
| $(CH_2)_7CH_3$ | Ph | (6-1-56t) |
| $OCH_3$ | Ph | (6-1-57t) |
| $OCH_2CH_3$ | Ph | (6-1-58t) |
| $CH(CH_3)_2$ | Ph | (6-1-59t) |
| $C(CH_3)_3$ | Ph | (6-1-60t) |
| $N(CH_3)_2$ | Ph | (6-1-61t) |
| F | Ph | (6-1-62t) |
| Cl | Ph | (6-1-63t) |
| Br | Ph | (6-1-64t) |

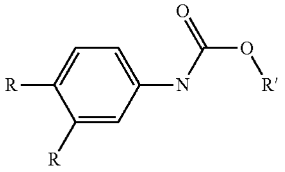

| R | R' | |
|---|---|---|
| $CH_3$ | $CH_3$ | (6-1-65p) |
| $(CH_2)_3CH_3$ | $CH_3$ | (6-1-66p) |
| $(CH_2)_7CH_3$ | $CH_3$ | (6-1-67p) |
| $OCH_3$ | $CH_3$ | (6-1-68p) |
| $OCH_2CH_3$ | $CH_3$ | (6-1-69p) |
| $CH(CH_3)_2$ | $CH_3$ | (6-1-70p) |
| $C(CH_3)_3$ | $CH_3$ | (6-1-71p) |
| $N(CH_3)_2$ | $CH_3$ | (6-1-72p) |
| F | $CH_3$ | (6-1-73p) |
| Cl | $CH_3$ | (6-1-74p) |
| Br | $CH_3$ | (6-1-75p) |
| $CH_3$ | $CH(CH_3)_2$ | (6-1-65q) |
| $(CH_2)_3CH_3$ | $CH(CH_3)_2$ | (6-1-66q) |
| $(CH_2)_7CH_3$ | $CH(CH_3)_2$ | (6-1-67q) |
| $OCH_3$ | $CH(CH_3)_2$ | (6-1-68q) |
| $OCH_2CH_3$ | $CH(CH_3)_2$ | (0-1-69q) |
| $CH(CH_3)_2$ | $CH(CH_3)_2$ | (6-1-70q) |
| $C(CH_3)_3$ | $CH(CH_3)_2$ | (6-1-71q) |
| $N(CH_3)_2$ | $CH(CH_3)_2$ | (6-1-72q) |
| F | $CH(CH_3)_2$ | (6-1-73q) |
| Cl | $CH(CH_3)_2$ | (6-1-74q) |
| Br | $CH(CH_3)_2$ | (6-1-75q) |
| $CH_3$ | $C(CH_3)_3$ | (6-1-65r) |
| $(CH_2)_3CH_3$ | $C(CH_3)_3$ | (6-1-66r) |
| $(CH_2)_7CH_3$ | $C(CH_3)_3$ | (6-1-67r) |
| $OCH_3$ | $C(CH_3)_3$ | (6-1-68r) |
| $OCH_2CH_3$ | $C(CH_3)_3$ | (6-1-69r) |
| $CH(CH_3)_2$ | $C(CH_3)_3$ | (6-1-70r) |
| $C(CH_3)_3$ | $C(CH_3)_3$ | (6-1-71r) |
| $N(CH_3)_2$ | $C(CH_3)_3$ | (6-1-72r) |
| F | $C(CH_3)_3$ | (6-1-73r) |
| Cl | $C(CH_3)_3$ | (6-1-74r) |

-continued

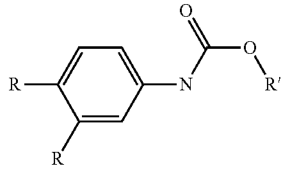

| R | R' | |
|---|---|---|
| Br | $C(CH_3)_3$ | (6-1-75r) |
| $CH_3$ | $(CH_2)_7CH_3$ | (6-1-65s) |
| $(CH_2)_3CH_3$ | $(CH_2)_7CH_3$ | (6-1-66s) |
| $(CH_2)_7CH_3$ | $(CH_2)_7CH_3$ | (6-1-67s) |
| $OCH_3$ | $(CH_2)_7CH_3$ | (6-1-68s) |
| $OCH_2CH_3$ | $(CH_2)_7CH_3$ | (6-1-69s) |
| $CH(CH_3)_2$ | $(CH_2)_7CH_3$ | (6-1-70s) |
| $C(CH_3)_3$ | $(CH_2)_7CH_3$ | (6-1-71s) |
| $N(CH_3)_2$ | $(CH_3)_7CH_3$ | (6-1-72s) |
| F | $(CH_2)_7CH_3$ | (6-1-73s) |
| Cl | $(CH_2)_7CH_3$ | (6-1-74s) |
| Br | $(CH_2)_7CH_3$ | (6-1-75s) |
| $CH_3$ | Ph | (6-1-65t) |
| $(CH_2)_3CH_3$ | Ph | (6-1-66t) |
| $(CH_2)_7CH_3$ | Ph | (6-1-67t) |
| $OCH_3$ | Ph | (6-1-68t) |
| $OCH_2CH_3$ | Ph | (6-1-69t) |
| $CH(CH_3)_2$ | Ph | (6-1-70t) |
| $C(CH_3)_3$ | Ph | (6-1-71t) |
| $N(CH_3)_2$ | Ph | (6-1-72t) |
| F | Ph | (6-1-73t) |
| Cl | Ph | (6-1-74t) |
| Br | Ph | (6-1-75t) |

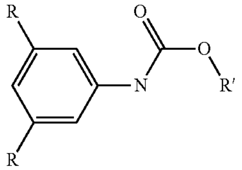

| R | R' | |
|---|---|---|
| $CH_3$ | $CH_3$ | (6-1-76p) |
| $(CH_2)_3CH_3$ | $CH_3$ | (6-1-77p) |
| $(CH_2)_7CH_3$ | $CH_3$ | (6-1-78p) |
| $OCH_3$ | $CH_3$ | (6-1-79p) |
| $OCH_2CH_3$ | $CH_3$ | (6-1-80p) |
| $CH(CH_3)_2$ | $CH_3$ | (6-1-81p) |
| $C(CH_3)_3$ | $CH_3$ | (6-1-82p) |
| $N(CH_3)_2$ | $CH_3$ | (6-1-83p) |
| F | $CH_3$ | (6-1-84p) |
| Cl | $CH_3$ | (6-1-85p) |
| Br | $CH_3$ | (6-1-86p) |
| $CH_3$ | $CH(CH_3)_2$ | (6-1-76q) |
| $(CH_2)_3CH_3$ | $CH(CH_3)_2$ | (6-1-77q) |
| $(CH_2)_7CH_3$ | $CH(CH_3)_2$ | (6-1-78q) |
| $OCH_3$ | $CH(CH_3)_2$ | (6-1-79q) |
| $OCH_2CH_3$ | $CH(CH_3)_2$ | (6-1-80q) |
| $CH(CH_3)_2$ | $CH(CH_3)_2$ | (6-1-81q) |
| $C(CH_3)_3$ | $CH(CH_3)_2$ | (6-1-82q) |
| $N(CH_3)_2$ | $CH(CH_3)_2$ | (6-1-83q) |
| F | $CH(CH_3)_2$ | (6-1-84q) |
| Cl | $CH(CH_3)_2$ | (6-1-85q) |
| Br | $CH(CH_3)_2$ | (6-1-86q) |
| $CH_3$ | $C(CH_3)_3$ | (6-1-76r) |
| $(CH_2)_3CH_3$ | $C(CH_3)_3$ | (6-1-77r) |
| $(CH_2)_7CH_3$ | $C(CH_3)_3$ | (6-1-78r) |
| $OCH_3$ | $C(CH_3)_3$ | (6-1-79r) |
| $OCH_2CH_3$ | $C(CH_3)_3$ | (6-1-80r) |
| $CH(CH_3)_2$ | $C(CH_3)_3$ | (6-1-81r) |
| $C(CH_3)_3$ | $C(CH_3)_3$ | (6-1-82r) |
| $N(CH_3)_2$ | $C(CH_3)_3$ | (6-1-83r) |

-continued

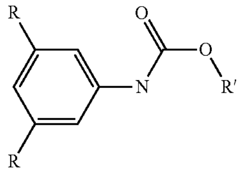

| R | R' | |
|---|---|---|
| F | $C(CH_3)_3$ | (6-1-84r) |
| Cl | $C(CH_3)_3$ | (6-1-85r) |
| Br | $C(CH_3)_3$ | (6-1-86r) |
| $CH_3$ | $(CH_2)_7CH_3$ | (6-1-76s) |
| $(CH_2)_3CH_3$ | $(CH_2)_7CH_3$ | (6-1-77s) |
| $(CH_2)_7CH_3$ | $(CH_2)_7CH_3$ | (6-1-78s) |
| $OCH_3$ | $(CH_2)_7CH_3$ | (6-1-79s) |
| $OCH_2CH_3$ | $(CH_2)_7CH_3$ | (6-1-80s) |
| $CH(CH_3)_2$ | $(CH_2)_7CH_3$ | (6-1-81s) |
| $C(CH_3)_3$ | $(CH_2)_7CH_3$ | (6-1-82s) |
| $N(CH_3)_2$ | $(CH_2)_7CH_3$ | (6-1-83s) |
| F | $(CH_2)_7CH_3$ | (6-1-84s) |
| Cl | $(CH_2)_7CH_3$ | (6-1-85s) |
| Br | $(CH_2)_7CH_3$ | (6-1-86s) |
| $CH_3$ | Ph | (6-1-76t) |
| $(CH_2)_3CH_3$ | Ph | (6-1-77t) |
| $(CH_2)_7CH_3$ | Ph | (6-1-78t) |
| $OCH_3$ | Ph | (6-1-79t) |
| $OCH_2CH_3$ | Ph | (6-1-80t) |
| $CH(CH_3)_2$ | Ph | (6-1-81t) |
| $C(CH_3)_3$ | Ph | (6-1-82t) |
| $N(CH_3)_2$ | Ph | (6-1-83t) |
| F | Ph | (6-1-84t) |
| Cl | Ph | (6-1-85t) |
| Br | Ph | (6-1-86t) |

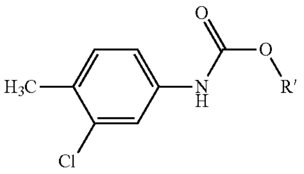

| | |
|---|---|
| R' = $CH_3$ | (6-1-87p) |
| $CH(CH_3)_2$ | (6-1-87q) |
| $C(CH_3)_3$ | (6-1-87r) |
| $(CH_2)_7CH_3$ | (6-1-87s) |
| Ph | (6-1-87t) |

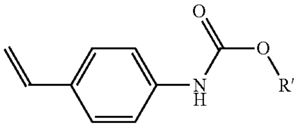

| | |
|---|---|
| R' = $CH_3$ | (6-1-88p) |
| $CH(CH_3)_2$ | (6-1-88q) |
| $C(CH_3)_3$ | (6-1-88r) |
| $(CH_2)_7CH_3$ | (6-1-88s) |
| Ph | (6-1-88t) |

-continued

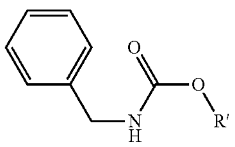

R′ = $CH_3$ (6-1-89p)
$CH(CH_3)_2$ (6-1-89q)
$C(CH_3)_3$ (6-1-89r)
$(CH_2)_7CH_3$ (6-1-89s)
Ph (6-1-89t)

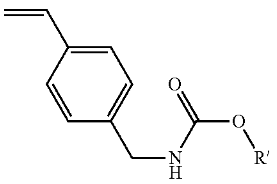

R′ = $CH_3$ (6-1-90p)
$CH(CH_3)_2$ (6-1-90q)
$C(CH_3)_3$ (6-1-90r)
$(CH_2)_7CH_3$ (6-1-90s)
Ph (6-1-90t)

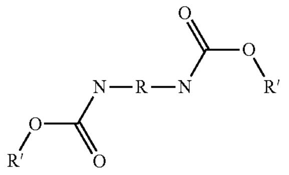

| R | R′ | |
|---|---|---|
| $—CH_2—$ | $CH_3$ | (6-2-1p) |
| $—CH_2CH_2—$ | $CH_3$ | (6-2-2p) |
| $—CH_2(CH_2)_2CH_2—$ | $CH_3$ | (6-2-3p) |
| $—CH_2(CH_2)_4CH_2—$ | $CH_3$ | (6-2-4p) |
| $—CH_2(CH_2)_6CH_2—$ | $CH_3$ | (6-2-5p) |
| $—CH_2(CH_2)_8CH_2—$ | $CH_3$ | (6-2-6p) |
| $—CH_2(CH_2)_{10}CH_2—$ | $CH_3$ | (6-2-7p) |
| $—CH_2—$ | $(CH_3)_2CH$ | (6-2-1q) |
| $—CH_2CH_2—$ | $(CH_3)_2CH$ | (6-2-2q) |
| $—CH_2(CH_2)_2CH_2—$ | $(CH_3)_2CH$ | (6-2-3q) |
| $—CH_2(CH_2)_4CH_2—$ | $(CH_3)_2CH$ | (6-2-4q) |
| $—CH_2(CH_2)_6CH_2—$ | $(CH_3)_2CH$ | (6-2-5q) |
| $—CH_2(CH_2)_8CH_2—$ | $(CH_3)_2CH$ | (6-2-6q) |
| $—CH_2(CH_2)_{10}CH_2—$ | $(CH_3)_2CH$ | (6-2-7q) |
| $—CH_2—$ | $(CH_3)_3C$ | (6-2-1r) |
| $—CH_2CH_2—$ | $(CH_3)_3C$ | (6-2-2r) |
| $—CH_2(CH_2)_2CH_2—$ | $(CH_3)_3C$ | (6-2-3r) |
| $—CH_2(CH_2)_4CH_2—$ | $(CH_3)_3C$ | (6-2-4r) |
| $—CH_2(CH_2)_6CH_2—$ | $(CH_3)_3C$ | (6-2-5r) |
| $—CH_2(CH_2)_8CH_2—$ | $(CH_3)_3C$ | (6-2-6r) |
| $—CH_2(CH_2)_{10}CH_2—$ | $(CH_3)_3C$ | (6-2-7r) |
| $—CH_2—$ | $CH_3(CH_3)_7$ | (6-2-1s) |
| $—CH_2CH_2—$ | $CH_3(CH_3)_7$ | (6-2-2s) |
| $—CH_2(CH_2)_2CH_2—$ | $CH_3(CH_3)_7$ | (6-2-3s) |
| $—CH_2(CH_2)_4CH_2—$ | $CH_3(CH_3)_7$ | (6-2-4s) |
| $—CH_2(CH_2)_6CH_2—$ | $CH_3(CH_3)_7$ | (6-2-5s) |
| $—CH_2(CH_2)_8CH_2—$ | $CH_3(CH_3)_7$ | (6-2-6s) |
| $—CH_2(CH_2)_{10}CH_2—$ | $CH_3(CH_3)_7$ | (6-2-7s) |
| $—CH_2—$ | Ph | (6-2-1t) |
| $—CH_2CH_2—$ | Ph | (6-2-2t) |
| $—CH_2(CH_2)_2CH_2—$ | Ph | (6-2-3t) |
| $—CH_2(CH_2)_4CH_2—$ | Ph | (6-2-4t) |
| $—CH_2(CH_2)_6CH_2—$ | Ph | (6-2-5t) |
| $—CH_2(CH_2)_8CH_2—$ | Ph | (6-2-6t) |
| $—CH_2(CH_2)_{10}CH_2—$ | Ph | (6-2-7t) |

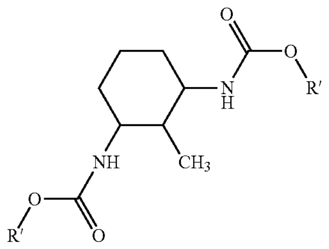

R′ = $CH_3$ (6-2-8p)
$CH(CH_3)_2$ (6-2-8q)
$C(CH_3)_3$ (6-2-8r)
$(CH_2)_7CH_3$ (6-2-8s)
Ph (6-2-8t)

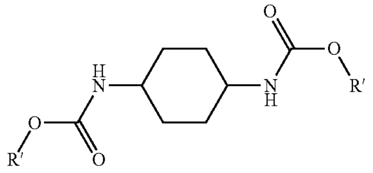

R′ = $CH_3$ (6-2-9p)
$CH(CH_3)_2$ (6-2-9q)
$C(CH_3)_3$ (6-2-9r)
$(CH_2)_7CH_3$ (6-2-9s)
Ph (6-2-9t)

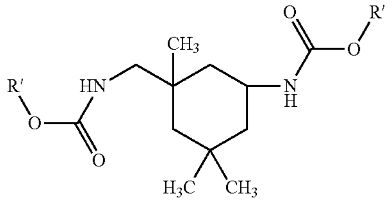

R′ = $CH_3$ (6-2-10p)
$CH(CH_3)_2$ (6-2-10q)
$C(CH_3)_3$ (6-2-10r)
$(CH_2)_7CH_3$ (6-2-10s)
Ph (6-2-10t)

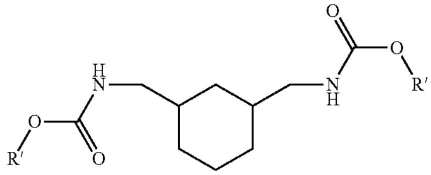

R′ = $CH_3$ (6-2-11p)
$CH(CH_3)_2$ (6-2-11q)
$C(CH_3)_3$ (6-2-11r)
$(CH_2)_7CH_3$ (6-2-11s)
Ph (6-2-11t)

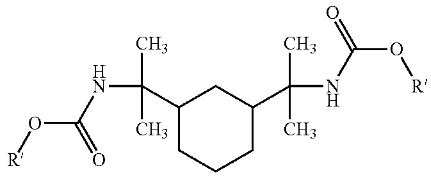

R′ = $CH_3$ (6-2-12p)
$CH(CH_3)_2$ (6-2-12q)
$C(CH_3)_3$ (6-2-12r)
$(CH_2)_7CH_3$ (6-2-12s)
Ph (6-2-12t)

-continued

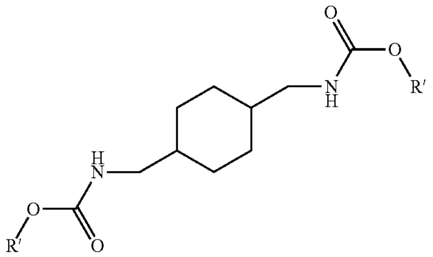

R′ = $CH_3$ (6-2-13p)
$CH(CH_3)_2$ (6-2-13q)
$C(CH_3)_3$ (6-2-13r)
$(CH_2)_7CH_3$ (6-2-13s)
Ph (6-2-13t)

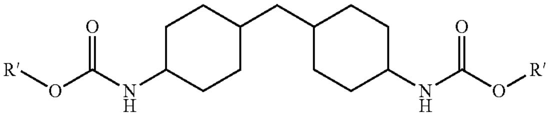

R′ = $CH_3$ (6-2-14p)
$CH(CH_3)_2$ (6-2-14q)
$C(CH_3)_3$ (6-2-14r)
$(CH_2)_7CH_3$ (6-2-14s)
Ph (6-2-14t)

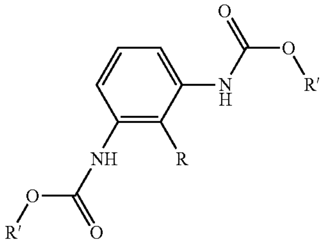

| R | R' | |
|---|---|---|
| H | $CH_3$ | (6-2-15p) |
| H | $CH(CH_3)_2$ | (6-2-15q) |
| H | $C(CH_3)_3$ | (6-2-15r) |
| H | $(CH_2)_7CH_3$ | (6-2-15s) |
| H | Ph | (6-2-15t) |
| $CH_3$ | $CH_3$ | (6-2-16p) |
| $CH_3$ | $CH(CH_3)_2$ | (6-2-16q) |
| $CH_3$ | $C(CH_3)_3$ | (6-2-16r) |
| $CH_3$ | $(CH_2)_7CH_3$ | (6-2-16s) |
| $CH_3$ | Ph | (6-2-16t) |

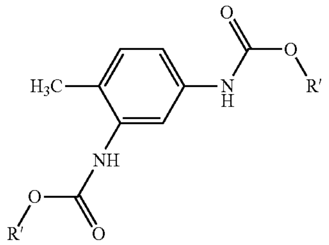

R′ = $CH_3$ (6-2-17p)
$CH(CH_3)_2$ (6-2-17q)
$C(CH_3)_3$ (6-2-17r)
$(CH_2)_7CH_3$ (6-2-17s)
Ph (6-2-17t)

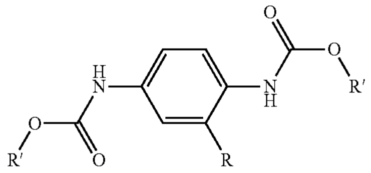

| R | R' | |
|---|---|---|
| H | $CH_3$ | (6-2-18p) |
| H | $CH(CH_3)_2$ | (6-2-18q) |
| H | $C(CH_3)_3$ | (6-2-18r) |
| H | $(CH_2)_7CH_3$ | (6-2-18s) |
| H | Ph | (6-2-18t) |
| $CH_3$ | $CH_3$ | (6-2-19p) |
| $CH_3$ | $CH(CH_3)_2$ | (6-2-19q) |
| $CH_3$ | $C(CH_3)_3$ | (6-2-19r) |
| $CH_3$ | $(CH_2)_7CH_3$ | (6-2-19s) |
| $CH_3$ | Ph | (6-2-19t) |

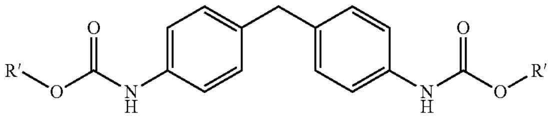

R′ = $CH_3$ (6-2-20p)
$CH(CH_3)_2$ (6-2-20q)
$C(CH_3)_3$ (6-2-20r)
$(CH_2)_7CH_3$ (6-2-20s)
Ph (6-2-20t)

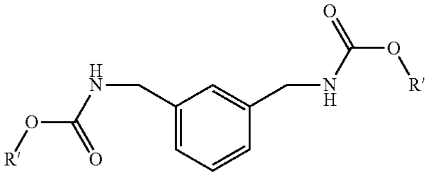

R′ = $CH_3$ (6-2-21p)
$CH(CH_3)_2$ (6-2-21q)
$C(CH_3)_3$ (6-2-21r)
$(CH_2)_7CH_3$ (6-2-21s)
Ph (6-2-21t)

-continued

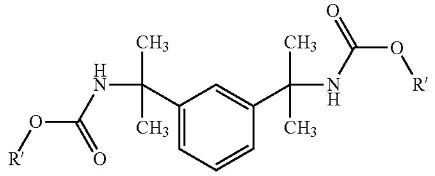

R' = $CH_3$ (6-2-22p)
$CH(CH_3)_2$ (6-2-22q)
$C(CH_3)_3$ (6-2-22r)
$(CH_2)_7CH_3$ (6-2-22s)
Ph (6-2-22t)

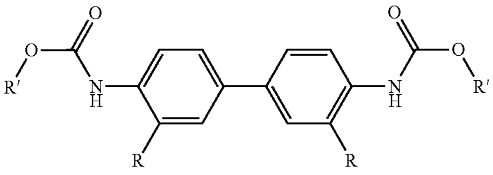

| R | R' | |
|---|---|---|
| $CH_3$ | $CH_3$ | (6-2-23p) |
| $CH_3$ | $CH(CH_3)_2$ | (6-2-23q) |
| $CH_3$ | $C(CH_3)_3$ | (6-2-23r) |
| $CH_3$ | $(CH_2)_7CH_3$ | (6-2-23s) |
| $CH_3$ | Ph | (6-2-23t) |
| $CH_2CH_3$ | $CH_3$ | (6-2-24p) |
| $CH_2CH_3$ | $CH(CH_3)_2$ | (6-2-24q) |
| $CH_2CH_3$ | $C(CH_3)_3$ | (6-2-24r) |
| $CH_2CH_3$ | $(CH_2)_7CH_3$ | (6-2-24s) |
| $CH_2CH_3$ | Ph | (6-2-24t) |
| $OCH_3$ | $CH_3$ | (6-2-25p) |
| $OCH_3$ | $CH(CH_3)_2$ | (6-2-25q) |
| $OCH_3$ | $C(CH_3)_3$ | (6-2-25r) |
| $OCH_3$ | $(CH_2)_7CH_3$ | (6-2-25s) |
| $OCH_3$ | Ph | (6-2-25t) |

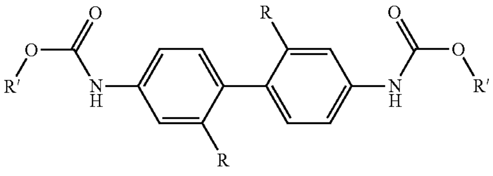

| R | R' | |
|---|---|---|
| $CH_3$ | $CH_3$ | (6-2-26p) |
| $CH_3$ | $CH(CH_3)_2$ | (6-2-26q) |
| $CH_3$ | $C(CH_3)_3$ | (6-2-26r) |
| $CH_3$ | $(CH_2)_7CH_3$ | (6-2-26s) |
| $CH_3$ | Ph | (6-2-26t) |
| $CF_3$ | $CH_3$ | (6-2-27p) |
| $CF_3$ | $CH(CH_3)_2$ | (6-2-27q) |
| $CF_3$ | $C(CH_3)_3$ | (6-2-27r) |
| $CF_3$ | $(CH_2)_7CH_3$ | (6-2-27s) |
| $CF_3$ | Ph | (6-2-27t) |

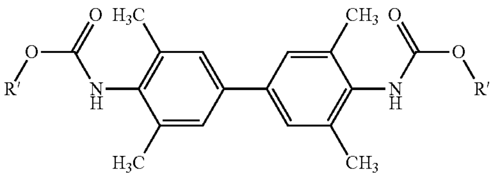

R' = $CH_3$ (6-2-28p)
$CH(CH_3)_2$ (6-2-28q)
$C(CH_3)_3$ (6-2-28r)
$(CH_2)_7CH_3$ (6-2-28s)
Ph (6-2-28t)

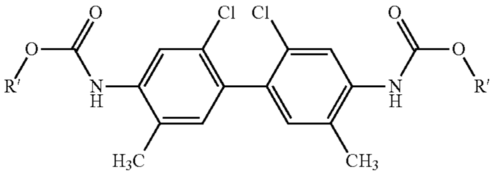

R' = $CH_3$ (6-2-29p)
$CH(CH_3)_2$ (6-2-29q)
$C(CH_3)_3$ (6-2-29r)
$(CH_2)_7CH_3$ (6-2-29s)
Ph (6-2-29t)

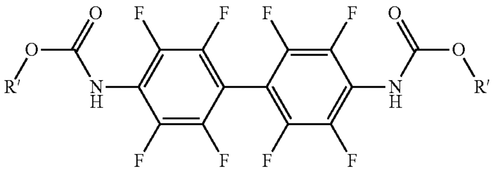

R' = $CH_3$ (6-2-30p)
$CH(CH_3)_2$ (6-2-30q)
$C(CH_3)_3$ (6-2-30r)
$(CH_2)_7CH_3$ (6-2-30s)
Ph (6-2-30t)

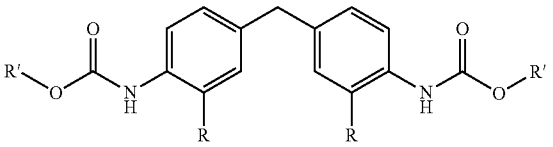

| R | R' | |
|---|---|---|
| $CH_3$ | $CH_3$ | (6-2-31p) |
| $CH_3$ | $CH(CH_3)_2$ | (6-2-31q) |
| $CH_3$ | $C(CH_3)_3$ | (6-2-31r) |
| $CH_3$ | $(CH_2)_7CH_3$ | (6-2-31s) |
| $CH_3$ | Ph | (6-2-31t) |
| Cl | $CH_3$ | (6-2-32p) |
| Cl | $CH(CH_3)_2$ | (6-2-32q) |
| Cl | $C(CH_3)_3$ | (6-2-32r) |
| Cl | $(CH_2)_7CH_3$ | (6-2-32s) |
| Cl | Ph | (6-2-32t) |

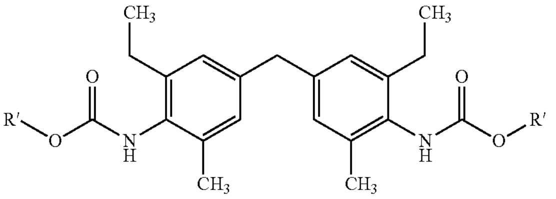
| | |
|---|---|
| R′ = $CH_3$ | (6-2-33p) |
| $CH(CH_3)_2$ | (6-2-33q) |
| $C(CH_3)_3$ | (6-2-33r) |
| $(CH_2)_7CH_3$ | (6-2-33s) |
| Ph | (6-2-33t) |
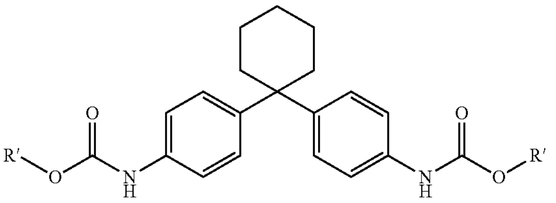
| | |
|---|---|
| R′ = $CH_3$ | (6-2-34p) |
| $CH(CH_3)_2$ | (6-2-34q) |
| $C(CH_3)_3$ | (6-2-34r) |
| $(CH_2)_7CH_3$ | (6-2-34s) |
| Ph | (6-2-34t) |
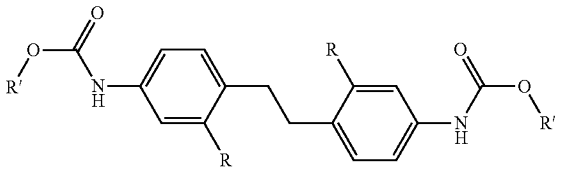
| R | R' | |
|---|---|---|
| H | $CH_3$ | (6-2-35p) |
| H | $CH(CH_3)_2$ | (6-2-35q) |
| H | $C(CH_3)_3$ | (6-2-35r) |
| H | $(CH_2)_7CH_3$ | (6-2-35s) |
| H | Ph | (6-2-35t) |
| $CH_3$ | $CH_3$ | (6-2-36p) |
| $CH_3$ | $CH(CH_3)_2$ | (6-2-36q) |
| $CH_3$ | $C(CH_3)_3$ | (6-2-36r) |
| $CH_3$ | $(CH_2)_7CH_3$ | (6-2-36s) |
| $CH_3$ | Ph | (6-2-36t) |
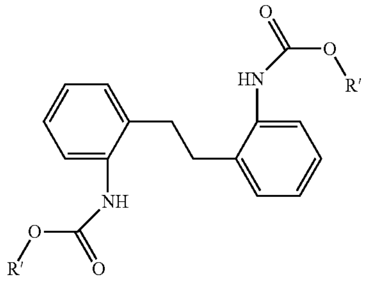
| | |
|---|---|
| R′ = $CH_3$ | (6-2-37p) |
| $CH(CH_3)_2$ | (6-2-37q) |
| $C(CH_3)_3$ | (6-2-37r) |
| $(CH_2)_7CH_3$ | (6-2-37s) |
| Ph | (6-2-37t) |
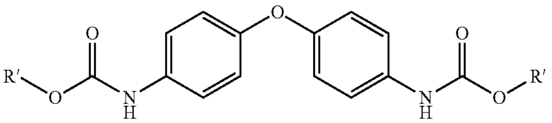
| | |
|---|---|
| R′ = $CH_3$ | (6-2-38p) |
| $CH(CH_3)_2$ | (6-2-38q) |
| $C(CH_3)_3$ | (6-2-38r) |
| $(CH_2)_7CH_3$ | (6-2-38s) |
| Ph | (6-2-38t) |
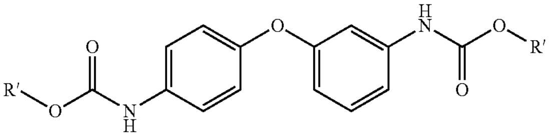
| | |
|---|---|
| R′ = $CH_3$ | (6-2-39p) |
| $CH(CH_3)_2$ | (6-2-39q) |
| $C(CH_3)_3$ | (6-2-39r) |
| $(CH_2)_7CH_3$ | (6-2-39s) |
| Ph | (6-2-39t) |
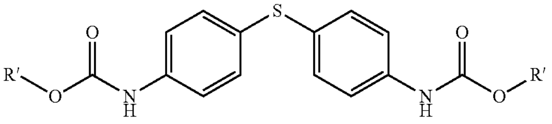
| | |
|---|---|
| R′ = $CH_3$ | (6-2-40p) |
| $CH(CH_3)_2$ | (6-2-40q) |
| $C(CH_3)_3$ | (6-2-40r) |
| $(CH_2)_7CH_3$ | (6-2-40s) |
| Ph | (6-2-40t) |

-continued

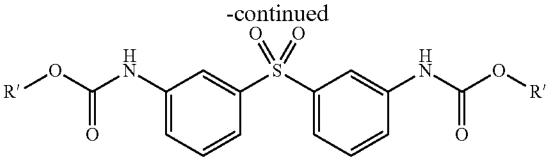

R′ = $CH_3$ (6-2-41p)
$CH(CH_3)_2$ (6-2-41q)
$C(CH_3)_3$ (6-2-41r)
$(CH_2)_7CH_3$ (6-2-41s)
Ph (6-2-41t)

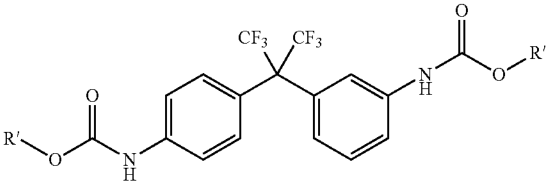

R′ = $CH_3$ (6-2-42p)
$CH(CH_3)_2$ (6-2-42q)
$C(CH_3)_3$ (6-2-42r)
$(CH_2)_7CH_3$ (6-2-42s)
Ph (6-2-42t)

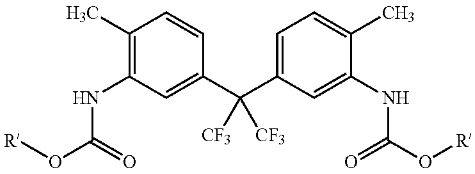

R′ = $CH_3$ (6-2-43p)
$CH(CH_3)_2$ (6-2-43q)
$C(CH_3)_3$ (6-2-43r)
$(CH_2)_7CH_3$ (6-2-43s)
Ph (6-2-43t)

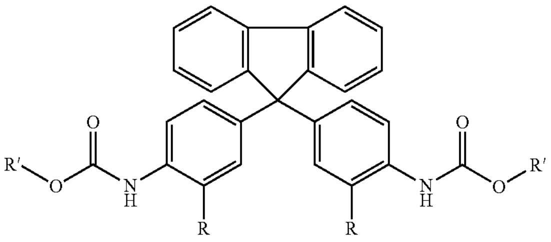

| R | R' | |
|---|---|---|
| H | $CH_3$ | (6-2-44p) |
| H | $CH(CH_3)_2$ | (6-2-44q) |
| H | $C(CH_3)_3$ | (6-2-44r) |
| H | $(CH_2)_7CH_3$ | (6-2-44s) |
| H | Ph | (6-2-44t) |
| $CH_3$ | $CH_3$ | (6-2-45p) |
| $CH_3$ | $CH(CH_3)_2$ | (6-2-45q) |
| $CH_3$ | $C(CH_3)_3$ | (6-2-45r) |
| $CH_3$ | $(CH_2)_7CH_3$ | (6-2-45s) |
| $CH_3$ | Ph | (6-2-45t) |
| F | $CH_3$ | (6-2-46p) |
| F | $CH(CH_3)_2$ | (6-2-46q) |
| F | $C(CH_3)_3$ | (6-2-46r) |
| F | $(CH_2)_7CH_3$ | (6-2-46s) |
| F | Ph | (6-2-46t) |
| Cl | $CH_3$ | (6-2-47p) |
| Cl | $CH(CH_3)_2$ | (6-2-47q) |
| Cl | $C(CH_3)_3$ | (6-2-47r) |
| Cl | $(CH_2)_7CH_3$ | (6-2-47s) |
| Cl | Ph | (6-2-47t) |

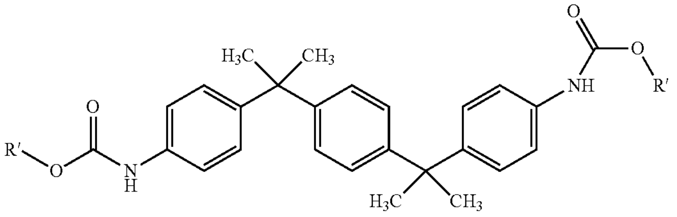

R′ = $CH_3$ (6-2-48p)
$CH(CH_3)_2$ (6-2-48q)
$C(CH_3)_3$ (6-2-48r)
$(CH_2)_7CH_3$ (6-2-48s)
Ph (6-2-48t)

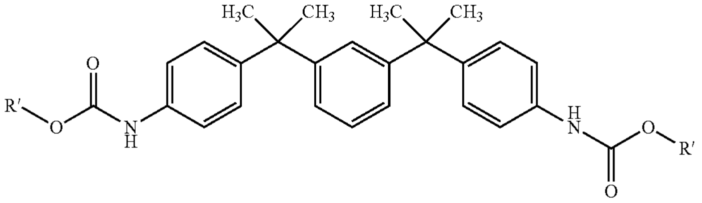

R′ = $CH_3$ (6-2-49p)
$CH(CH_3)_2$ (6-2-49q)
$C(CH_3)_3$ (6-2-49r)
$(CH_2)_7CH_3$ (6-2-49s)
Ph (6-2-49t)

-continued
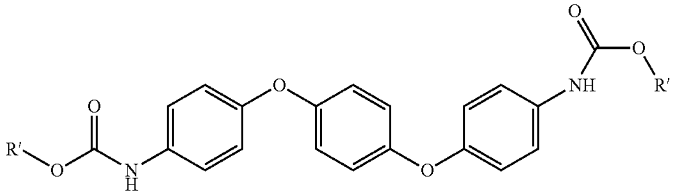
R′ = $CH_3$ (6-2-50p)
$CH(CH_3)_2$ (6-2-50q)
$C(CH_3)_3$ (6-2-50r)
$(CH_2)_7CH_3$ (6-2-50s)
Ph (6-2-50t)
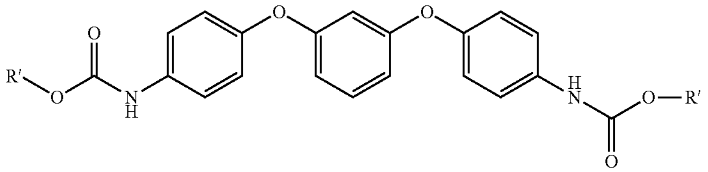
R′ = $CH_3$ (6-2-51p)
$CH(CH_3)_2$ (6-2-51q)
$C(CH_3)_3$ (6-2-51r)
$(CH_2)_7CH_3$ (6-2-51s)
Ph (6-2-51t)
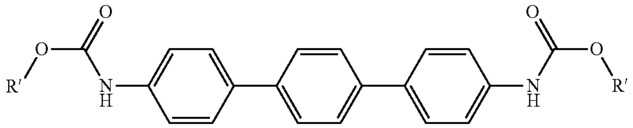
R′ = $CH_3$ (6-2-52p)
$CH(CH_3)_2$ (6-2-52q)
$C(CH_3)_3$ (6-2-52r)
$(CH_2)_7CH_3$ (6-2-52s)
Ph (6-2-52t)
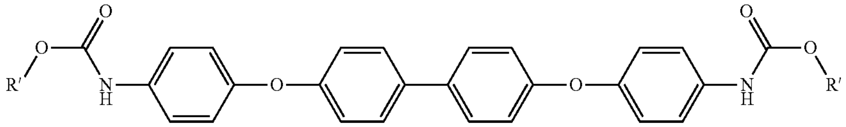
R′ = $CH_3$ (6-2-53p)
$CH(CH_3)_2$ (6-2-53q)
$C(CH_3)_3$ (6-2-53r)
$(CH_2)_7CH_3$ (6-2-53s)
Ph (6-2-53t)
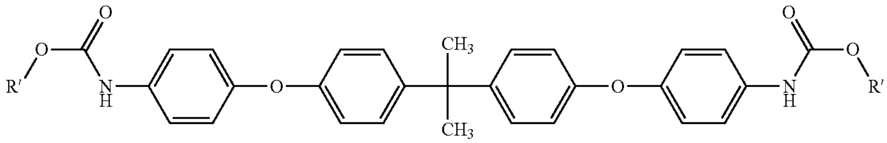
R′ = $CH_3$ (6-2-54p)
$CH(CH_3)_2$ (6-2-54q)
$C(CH_3)_3$ (6-2-54r)
$(CH_2)_7CH_3$ (6-2-54s)
Ph (6-2-54t)

-continued

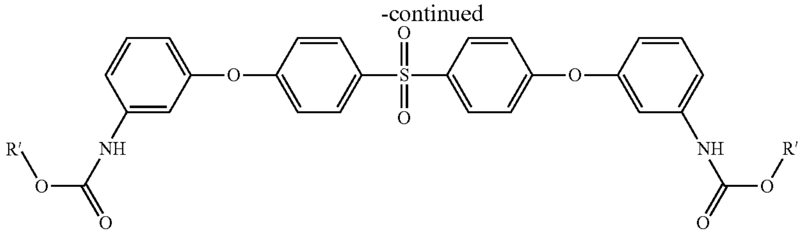

| | | |
|---|---|---|
| R' = | $CH_3$ | (6-2-55p) |
| | $CH(CH_3)_2$ | (6-2-55q) |
| | $C(CH_3)_3$ | (6-2-55r) |
| | $(CH_2)_7CH_3$ | (6-2-55s) |
| | Ph | (6-2-55t) |

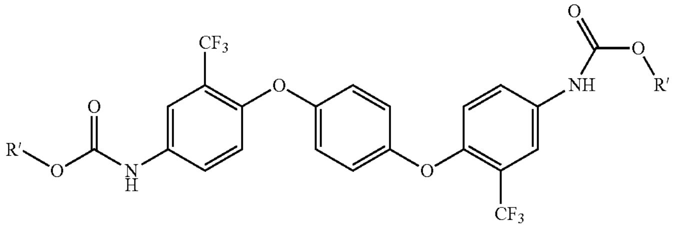

| | | |
|---|---|---|
| R' = | $CH_3$ | (6-2-56p) |
| | $CH(CH_3)_2$ | (6-2-56q) |
| | $C(CH_3)_3$ | (6-2-56r) |
| | $(CH_2)_7CH_3$ | (6-2-56s) |
| | Ph | (6-2-56t) |

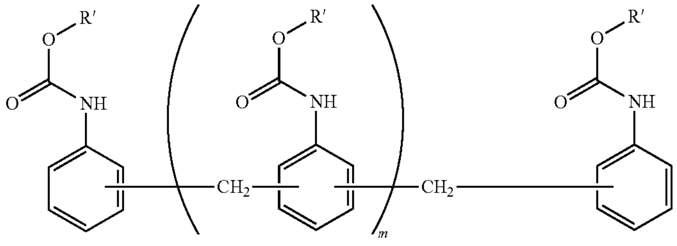

| | | |
|---|---|---|
| R' = | $CH_3$ | (6-3-1p) |
| | $CH(CH_3)_2$ | (6-3-1q) |
| | $C(CH_3)_3$ | (6-3-1r) |
| | $(CH_2)_7CH_3$ | (6-3-1s) |
| | Ph | (6-3-1t) |

Preferable examples of the urethane compound (6) include compounds represented by the formulas (6-1-30p), (6-1-30q), (6-1-30r), (6-1-30s), (6-1-30t), (6-1-41p), (6-1-41q), (6-1-41r), (6-1-41s), (6-1-41t), (6-1-45p), (6-1-45q), (6-1-45r), (6-1-45s), (6-1-45t), (6-1-46p), (6-1-46q), (6-1-46r), (6-1-46s), (6-1-46t), (6-1-48p), (6-1-48q), (6-1-48r), (6-1-48s), (6-1-48t), (6-1-52p), (6-1-52q), (6-1-52r), (6-1-52s), (6-1-52t), (6-1-59p), (6-1-59q), (6-1-59r), (6-1-59s), (6-1-59t), (6-1-88p), (6-1-88q), (6-1-88r), (6-1-88s), (6-1-88t), (6-1-89p), (6-1-89q), (6-1-89r), (6-1-89s), (6-1-89t), (6-1-90p), (6-1-90q), (6-1-90r), (6-1-90s), (6-1-90t), (6-2-20p), (6-2-20q), (6-2-20r), (6-2-20s), (6-2-20t), (6-2-30p), (6-2-30q), (6-2-30r), (6-2-30s), (6-2-30t), (6-2-41p), (6-2-41q), (6-2-41r), (6-2-41s), (6-2-41t), (6-2-48p), (6-2-48q), (6-2-48r), (6-2-48s), (6-2-48t), (6-2-49p), (6-2-49q), (6-2-49r), (6-2-49s), (6-2-49t), (6-2-51p), (6-2-51q), (6-2-51r), (6-2-51s), and (6-2-51t); and particularly preferably compounds represented by the formulas (6-1-30r), (6-1-41r), (6-1-45r), (6-1-46r)(6-1-48r), (6-1-52p), (6-1-52q), (6-1-52r), (6-1-52s), (6-1-52t), (6-1-59r), (6-1-88r), (6-1-89r), (6-1-90r), (6-2-20r), (6-2-41r), (6-2-48r), (6-2-49r), and (6-2-51r).

The urethane compound (6) used as a raw material is not particularly limited. Urethane compounds produced by various methods can be widely used. For example, the urethane compound (6) can be produced by the following methods.

Method I: A method of reacting an amine compound represented by the following formula (7) and a carbonyl compound represented by the following formula (8a), (8b), or (8c) (hereinafter referred to as the "carbonyl compound (8)").

Formula (7):

$$A\text{+}NH_2]_n \qquad (7)$$

wherein A and n are as defined above.

Formula (8a)

(8a)

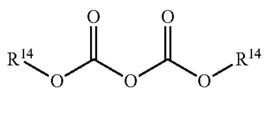

wherein $R^4$ is as defined above.

Formula (8b)

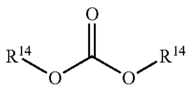

(8b)

wherein $R^{14}$ is as defined above.

Formula (8c)

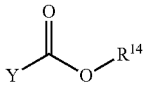

(8c)

wherein $R^{14}$ is as defined above, and Y is a halogen atom.

Method II: a method of reacting the amine compound represented by the formula (7) and phosgene, and then reacting the obtained reaction product and an alcohol compound.

Method III: a method of reacting the amine compound represented by the formula (7), urea, and an alcohol compound.

Method IV: a method of reacting the isocyanate compound (5) and an alcohol compound represented by the following formula (9).

Formula (9):

$$R^{14}—OH \quad (9)$$

wherein $R^{14}$ is as defined above.

The raw material compounds used in the methods I, II, III, and IV can be known compounds, or compounds that can be produced by known organic synthesis methods.

Among these, the methods I and IV are preferable in terms of ease of handling reagents, ease of reaction, ease of obtaining raw materials, etc. The methods I and IV are explained in detail below.

The method I is explained.

In the formula (7), A and n are as defined above. The amine compound represented by the formula (7) (hereinafter referred to as the "amine compound (7)") is preferably an amine compound represented by the formula (7-1), (7-2), or (7-3).

Formula (7-1):

$$R^4—NH_2 \quad (7\text{-}1)$$

wherein $R^4$ is as defined above.

Formula (7-2):

$$H_2N—R^5—NH_2 \quad (7\text{-}2)$$

wherein $R^5$ is as defined above.

Formula (7-3):

(7-3)

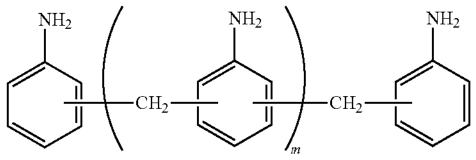

wherein m is as defined above.

In the formula (7-1), $R^4$ is as defined above.

In the formula (7-2), $R^5$ is as defined above.

In the formula (7-3), m is as defined above.

Although specific examples of the amine compound (7) are shown below, the present invention is not limited thereto. In the following specific examples, Et represents an ethyl group, Pr represents a n-propyl group, and Bu represents a n-butyl group.

(7-1-1)

$H_3C—NH_2$ (7-1-2)

$Et—NH_2$ (7-1-3)

$Pr—NH_2$ (7-1-4)

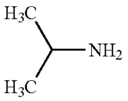

(7-1-5)

$Bu—NH_2$ (7-1-6)

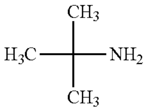

(7-1-7)

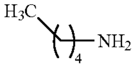

(7-1-8)

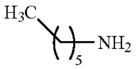

(7-1-9)

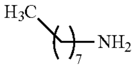

(7-1-10)

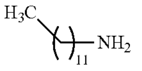

(7-1-11)

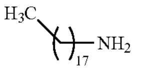

(7-1-12)

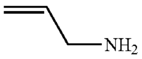

(7-1-13)

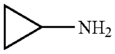

(7-1-14)

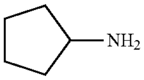

-continued (7-1-15)

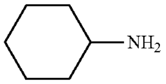

(7-1-16)

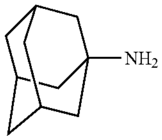

(7-1-17)

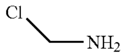

(7-1-18)

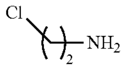

(7-1-19)

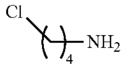

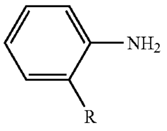

| | | |
|---|---|---|
| R = | H | (7-1-20) |
| | $CH_3$ | (7-1-21) |
| | $(CH_2)_3CH_3$ | (7-1-22) |
| | $(CH_2)_7CH_3$ | (7-1-23) |
| | $OCH_3$ | (7-1-24) |
| | $OCH_2CH_3$ | (7-1-25) |
| | $CH(CH_3)_2$ | (7-1-26) |
| | $C(CH_3)_3$ | (7-1-27) |
| | $N(CH_3)_2$ | (7-1-28) |
| | F | (7-1-29) |
| | Cl | (7-1-30) |
| | Br | (7-1-31) |

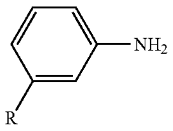

| | | |
|---|---|---|
| R = | $CH_3$ | (7-1-32) |
| | $(CH_2)_3CH_3$ | (7-1-33) |
| | $(CH_2)_7CH_3$ | (7-1-34) |
| | $OCH_3$ | (7-1-35) |
| | $OCH_2CH_3$ | (7-1-36) |
| | $CH(CH_3)_2$ | (7-1-37) |
| | $C(CH_3)_3$ | (7-1-38) |
| | $N(CH_3)_2$ | (7-1-39) |
| | F | (7-1-40) |
| | Cl | (7-1-41) |
| | Br | (7-1-42) |

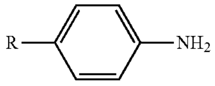

| | | |
|---|---|---|
| R = | $CH_3$ | (7-1-43) |
| | $(CH2)_3CH_3$ | (7-1-44) |
| | $(CH_2)_7CH_3$ | (7-1-45) |
| | $OCH_3$ | (7-1-46) |
| | $OCH_2CH_3$ | (7-1-47) |
| | $CH(CH_3)_2$ | (7-1-48) |
| | $C(CH_3)_3$ | (7-1-49) |
| | $N(CH_3)_2$ | (7-1-50) |
| | F | (7-1-51) |
| | Cl | (7-1-52) |
| | Br | (7-1-53) |

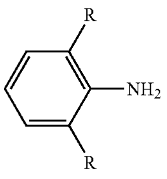

| | | |
|---|---|---|
| R = | $CH_3$ | (7-1-54) |
| | $(CH_2)_3CH_3$ | (7-1-55) |
| | $(CH_2)_7CH_3$ | (7-1-56) |
| | $OCH_3$ | (7-1-57) |
| | $OCH_2CH_3$ | (7-1-58) |
| | $CH(CH_3)_2$ | (7-1-59) |
| | $C(CH_3)_3$ | (7-1-60) |
| | $N(CH_3)_2$ | (7-1-61) |
| | F | (7-1-62) |
| | Cl | (7-1-63) |
| | Br | (7-1-64) |

-continued

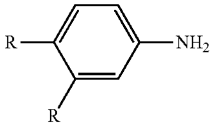

| | | |
|---|---|---|
| R = | $CH_3$ | (7-1-65) |
| | $(CH2)_3CH_3$ | (7-1-66) |
| | $(CH_2)_7CH_3$ | (7-1-67) |
| | $OCH_3$ | (7-1-68) |
| | $OCH_2CH_3$ | (7-1-69) |
| | $CH(CH_3)_2$ | (7-1-70) |
| | $C(CH_3)_3$ | (7-1-71) |
| | $N(CH_3)_2$ | (7-1-72) |
| | F | (7-1-73) |
| | Cl | (7-1-74) |
| | Br | (7-1-75) |

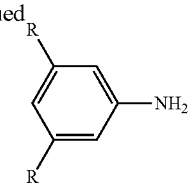

| | | |
|---|---|---|
| R = | $CH_3$ | (7-1-76) |
| | $(CH2)_3CH_3$ | (7-1-77) |
| | $(CH_2)_7CH_3$ | (7-1-78) |
| | $OCH_3$ | (7-1-79) |
| | $OCH_2CH_3$ | (7-1-80) |
| | $CH(CH_3)_2$ | (7-1-81) |
| | $C(CH_3)_3$ | (7-1-82) |
| | $N(CH_3)_2$ | (7-1-83) |
| | F | (7-1-84) |
| | Cl | (7-1-85) |
| | Br | (7-1-86) |

(7-1-87)

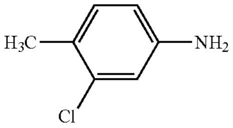

(7-1-88)

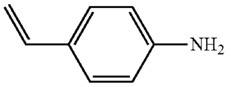

(7-1-89)

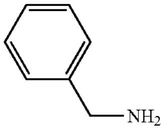

(7-1-90)

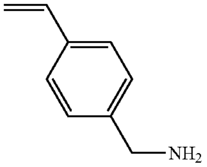

$H_2N—R—NH_2$

| | | |
|---|---|---|
| R = | $—CH_2—$ | (7-2-1) |
| | $—CH_2CH_2—$ | (7-2-2) |
| | $—CH_2(CH_2)_2CH_2—$ | (7-2-3) |
| | $—CH_2(CH_2)_4CH_2—$ | (7-2-4) |
| | $—CH_2(CH_2)_6CH_2—$ | (7-2-5) |
| | $—CH_2(CH_2)_8CH_2—$ | (7-2-6) |
| | $—CH_2(CH_2)_{10}CH_2—$ | (7-2-7) |

(7-2-8)

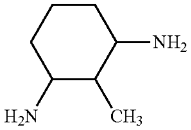

(7-2-9)

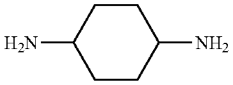

(7-2-10)

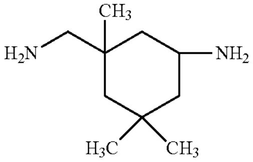

-continued
(7-2-11)
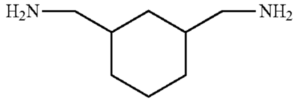
(7-2-12)
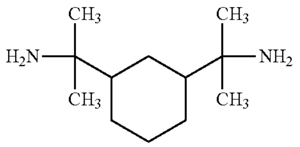
(7-2-13)
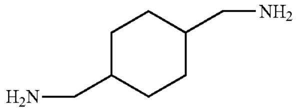
(7-2-14)
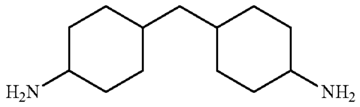
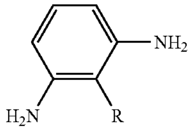
R = H (7-2-15)
$CH_3$ (7-2-16)
(7-2-17)
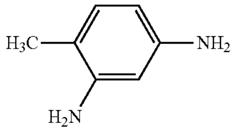
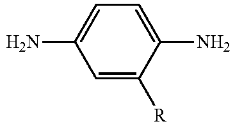
R = H (7-2-18)
$CH_3$ (7-2-19)
(7-2-20)
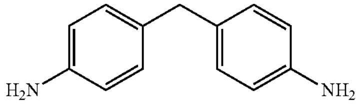
(7-2-21)
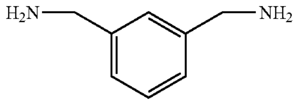
(7-2-22)
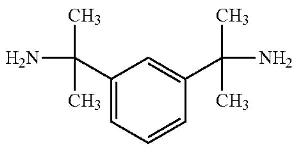
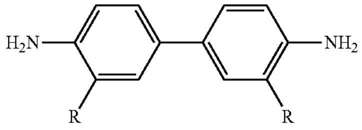
R = $CH_3$ (7-2-23)
$CH_2CH_3$ (7-2-24)
$OCH_3$ (7-2-25)
-continued
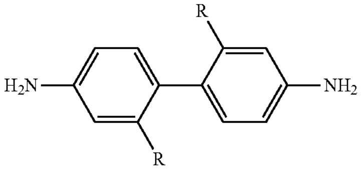
R = $CH_3$ (7-2-26)
$CF_3$ (7-2-27)
(7-2-28)
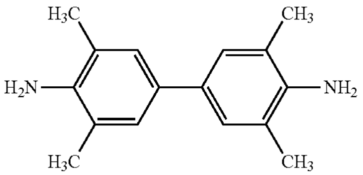
(7-2-29)
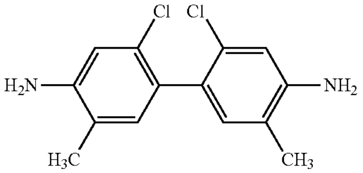
(7-2-30)
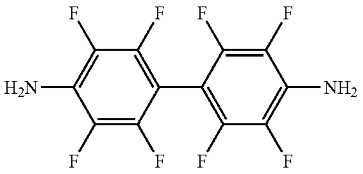
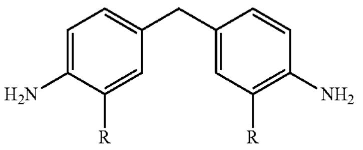
R = $CH_3$ (7-2-31)
Cl (7-2-32)
(7-2-33)
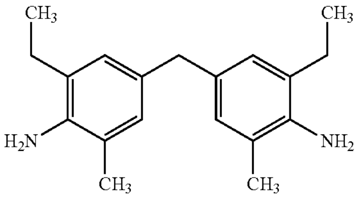
(7-2-34)
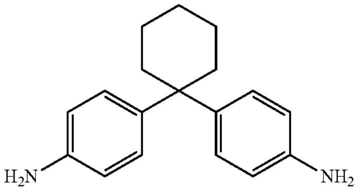
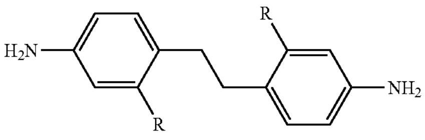
R = H (7-2-35)
$CH_3$ (7-2-36)

-continued (7-2-37)

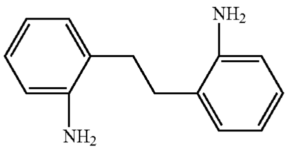

(7-2-38)

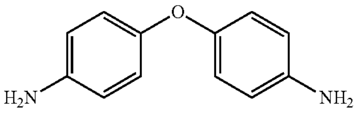

(7-2-39)

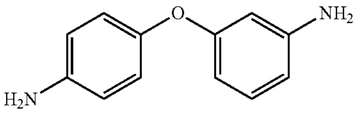

(7-2-40)

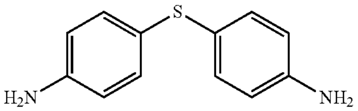

(7-2-41)

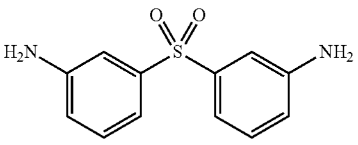

(7-2-42)

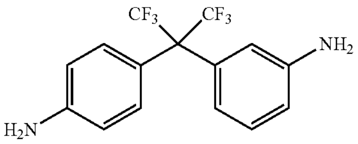

(7-2-43)

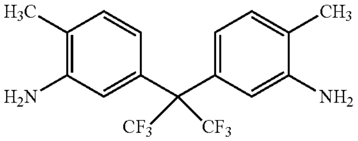

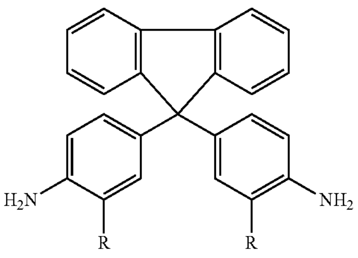

R = H (7-2-44)
CH$_3$ (7-2-45)
F (7-2-46)
Cl (7-2-47)

(7-2-48)

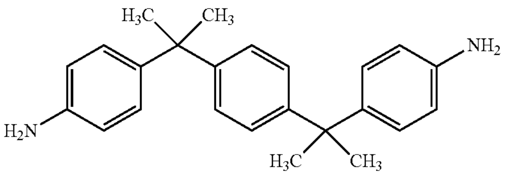

-continued (7-2-49)

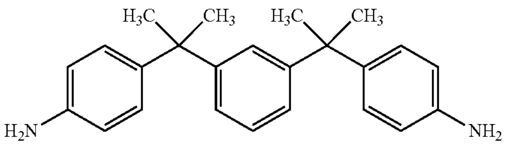

(7-2-50)

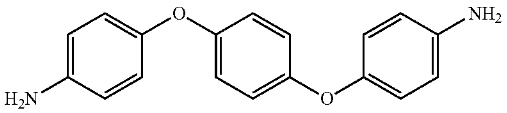

(7-2-51)

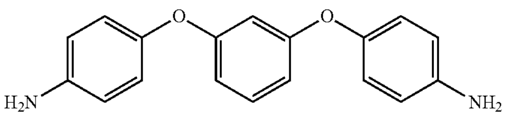

(7-2-52)

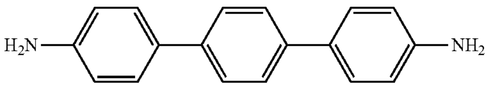

(7-2-53)

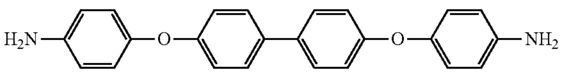

(7-2-54)

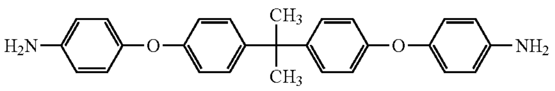

(7-2-55)

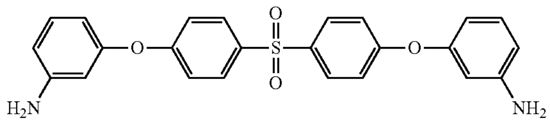

(7-2-56)

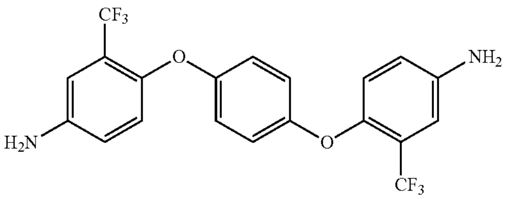

Preferable examples of the amine compound (7) include compounds represented by the formulas (7-1-41), (7-1-45), (7-1-46), (7-1-48), (7-1-52), (7-1-59), (7-1-88), (7-1-89), (7-1-90), (7-2-41), (7-2-48), (7-2-49), and (7-2-51).

In the formula (8a), $R^{14}$ is as defined above. Examples of the carbonyl compound represented by the formula (8a) include di-t-butyl dicarbonate, dibenzyl dicarbonate, di-t-amyl dicarbonate, diallyl dicarbonate, and the like; and preferably di-t-butyl dicarbonate and dibenzyl dicarbonate.

In the formula (8b), $R^{14}$ is as defined above. Examples of the carbonyl compound represented by the formula (8b) include dimethyl carbonate, diethyl carbonate, dipropyl carbonate, dibutyl carbonate, dipentyl carbonate, dihexyl carbonate, diphenyl carbonate, dibenzyl carbonate, and the like; and preferably dimethyl carbonate, diethyl carbonate, dipropyl carbonate, dibutyl carbonate, diphenyl carbonate, and dibenzyl carbonate.

In the formula (8c), $R^{14}$ is as defined above, and Y is a halogen atom. Examples of halogen atoms include fluorine, chlorine, bromine, and iodine atoms; and preferably chlorine atoms. Examples of the carbonyl compound represented by the formula (8c) include methyl chloroformate, ethyl chloroformate, propyl chloroformate, isopropyl chloroformate, 2-methoxyethyl chloroformate, butyl chloroformate, isobutyl chloroformate, amyl chloroformate, heptyl chloroformate, hexyl chloroformate, nonyl chloroformate, n-octyl chloroformate, decyl chloroformate, dodecyl chloroformate, hexadecyl chloroformate, phenyl chloroformate, 2-naphthyl chloroformate, benzyl chloroformate, and the like; and preferably methyl chloroformate, ethyl chloroformate, propyl chloroformate, isopropyl chloroformate, butyl chloroformate, n-octyl chloroformate, phenyl chloroformate, and benzyl chloroformate.

Among the carbonyl compounds represented by the formulas (8a), (8b), and (8c), the carbonyl compounds represented by the formulas (8a) and (8b) are preferably used, and the carbonyl compound represented by the formula (8a) is particularly preferably used, in terms of easy availability, ease of reaction, etc.

The amount of the carbonyl compound (8) used is generally 1 mol or more, and preferably 1 to 6 mol, per mol of amino groups in the amine compound (7).

When the amine compound (7) is reacted with the carbonyl compound (8), a base catalyst may be used, if necessary. Examples of base catalysts include organic bases, such as triethylamine and dimethylaminopyridine; and inorganic bases, such as potassium hydroxide, sodium hydroxide, and sodium hydrogen carbonate. Triethylamine is preferable.

The optimal reaction temperature varies depending on the raw materials, solvents, etc., used, but is generally room temperature or higher, and preferably 20 to 250° C.

A solvent may or may not be used. When a solvent is used, the solvent used is not particularly limited, as long as it does not affect the reaction. Specific examples of solvents include aromatic hydrocarbon solvents, such as toluene, benzene, and xylene; aliphatic or alicyclic hydrocarbon solvents, such as methylcyclohexane, cyclohexane, n-hexane, n-heptane, and octane; halogenated hydrocarbon solvents, such as dichloromethane and chloroform; ether solvents, such as diethyl ether, tetrahydrofuran, and 1,4-dioxane; alcohol solvents, such as methanol and ethanol; N,N-dimethylformamide, acetonitrile, and the like. Ether solvents and alcohol solvents are preferable, and tetrahydrofuran and methanol are particularly preferable. The amount of solvent used is generally 50 parts by weight or less, and preferably 0.1 to 10 parts by weight, per part by weight of the amine compound (4).

The reaction may be performed, if necessary, in an inert gas atmosphere, such as nitrogen, argon, or helium, which do not affect the reaction.

After completion of the reaction, the unreacted carbonyl compound (8) can be subjected to treatment with an amine compound, such as diethanolamine, washing with water or a weak acidic aqueous solution, concentration of the reaction mixture, or the like, to thereby isolate the urethane compound (1). If necessary, purification, such as recrystallization, may be performed.

The method IV is explained.

In the formula (9), $R^{14}$ is as defined above. Examples of the alcohol compound represented by the formula (9) (hereinafter referred to as the "alcohol compound (9)") include aliphatic alcohols, such as methanol, ethanol, isopropanol, t-butanol, n-octanol, methoxyethanol, and ethoxyethanol; aromatic alcohols, such as benzyl alcohol; and phenols, such as phenol. Preferred among these are methanol, ethanol, isopropanol, t-butanol, n-octanol, and phenol.

The amount of the alcohol compound (9) used is generally 1 mol or more, and preferably 1 to 70 mol, per mol of isocyanate groups in the isocyanate compound (5).

The optimal reaction temperature during reaction between the isocyanate compound (5) and the alcohol compound (9) varies depending on the raw materials, solvents, etc., used, but is generally room temperature or higher, and preferably 20 to 200° C.

When the isocyanate compound (5) is reacted with the alcohol compound (9), a catalyst may be used, if necessary. Examples of catalysts include organometallic compounds containing at least one metal element selected from the group consisting of tin, iron, lead, bismuth, mercury, titanium, hafnium, and zirconium; amine compounds; and the like. Preferable examples of organometallic compounds include tin carboxylate, dialkyltin oxide, and bismuth carboxylate; and more preferably dibutyltin dilaurate. Preferable examples of amine compounds include 1,4-diazabicyclo[2.2.2]octane, N,N,N',N",N"-pentamethyldiethylenetriamine, and bis(2-dimethylaminoethyl) ether.

A solvent may or may not be used. The alcohol compound (9) can also be used as a solvent by excessively using the alcohol compound (9). When a solvent is further used, in addition to the alcohol compound (9), the solvent used is not particularly limited, as long as it does not affect the reaction. Specific examples of solvents include aromatic hydrocarbon solvents, such as toluene, benzene, and xylene; aliphatic or alicyclic hydrocarbon solvents, such as methylcyclohexane, cyclohexane, n-hexane, n-heptane, and octane; halogenated hydrocarbon solvents, such as dichloromethane and chloroform; ether solvents, such as diethyl ether and tetrahydrofuran; and the like. Toluene is preferable. The amount of solvent used is generally 50 parts by weight or less, preferably 0.1 to 10 parts by weight, per part by weight of the isocyanate compound (5).

The reaction may be performed, if necessary, in an inert gas atmosphere, such as nitrogen, argon, or helium, which do not affect the reaction.

After completion of the reaction, the urethane compound (6) can be isolated by removing the solvent by concentration or filtration of the reaction mixture. If necessary, the obtained urethane compound (6) can be purified by, for example, washing with any solvent, and then can be reacted with the carboxylate compound (4).

In step 2', the carboxylate compound (4) is generally reacted in an amount of 0.8 mol or more, and preferably 1 to 3 mol, per mol of carbamate groups contained in the urethane compound (6).

The reaction temperature is not particularly limited, and may be equal to or lower than the boiling point of the solvent. The reaction temperature is generally 10° C. or more, preferably 40 to 200° C., and particularly preferably 80 to 150° C.

In step 2', a solvent may or may not be used. Examples of solvents include aromatic hydrocarbon solvents, such as toluene, benzene, and xylene; aliphatic or alicyclic hydrocarbon solvents, such as methylcyclohexane, cyclohexane, n-hexane, n-heptane, and octane; halogenated aliphatic hydrocarbon solvents, such as butyl chloride and 1,2-dichloroethane; halogenated aromatic hydrocarbon solvents, such as chlorobenzene; and the like. Aromatic hydrocarbon solvents and halogenated aromatic hydrocarbon solvents are preferable; and toluene, xylene, and chlorobenzene are particularly preferable. These solvents can be used as a mixture of two or more, if necessary.

Moreover, when a reaction mixture obtained by the reaction of the nitrogen-containing organic compound (3) and dimethyl carbonate is used as the carboxylate compound (4), the solvent in the reaction mixture can be directly used as a solvent for the reaction of the urethane compound (6) and the carboxylate compound (4). In this case, the reaction may be performed while adding a solvent, if necessary.

The amount of solvent used is generally 50 parts by weight or less, preferably 35 parts by weight or less, and more preferably 0.1 to 35 parts by weight, per part by weight of the carboxylate compound (4).

In step 2', the reaction may be performed, if necessary, in an inert gas atmosphere, such as nitrogen, argon, or helium, which do not affect the reaction.

After completion of the reaction, the amidate compound (1) can be obtained by removing the solvent by concentration or filtration of the reaction mixture. The obtained amidate compound (1) may be purified by a method, such as recrystallization.

Subsequently, the catalyst for polyurethane production of the present invention is explained.

The catalyst for polyurethane production of the present invention comprises an amidate compound (1) as an active ingredient. One or a mixture of two or more amidate compounds (1) can be used as the catalyst for polyurethane production. If necessary, a solvent etc. can be mixed. Further, a known catalyst for polyurethane production can be used in combination.

When the amidate compound (1) is mixed with a solvent etc. and/or combined with a known catalyst for polyurethane production to obtain a catalyst for polyurethane production, a catalyst composition for polyurethane production is obtained. In this case, a person skilled in the art can suitably determine the mixing ratio of the amidate compound (1) and the solvent, etc., and the mixing ratio of the amidate compound (1) and the known catalyst for polyurethane production.

Examples of known catalysts for polyurethane production include tertiary amine catalysts, such as triethylamine, N,N,N',N'-tetramethylethylenediamine, N,N,N',N'-tetramethylpropylenediamine, N,N,N',N",N"-pentamethyldiethylenetriamine, N,N,N',N",N"-pentamethyldipropylenetriamine, N,N, N',N'-tetramethylguanidine, 1,3,5-tris(N,N-dimethylaminopropyl)hexahydro-S-triazine, 1,4-diazabicyclo[2.2.2]octane (DABCO), 1,8-diazabicyclo[5.4.0]undecene-7, triethylenediamine, N,N,N',N'-tetramethylhexamethylenediamine, N-methyl-N'-(2-dimethylaminoethyl) piperazine, N, N'-dimethylpiperazine, dimethylcyclohexylamine, N-methylmorpholine, N-ethylmorpholine, bis(2-dimethylaminoethyl)ether, 1-methylimidazole, 1,2-dimethylimidazole, 1-isobutyl-2-methylimidazole, and 1-dimethylaminopropylimidazole; and quaternary ammonium salt compounds, such as tetraalkylammnonium halides (e.g., tetramethylamnonium chloride), tetraalkylammonium hydroxides (e.g., tetramethylammonium hydroxide salts), tetraalkylammnonium organic acid salts (e.g., tetramethylammnonium-2-ethylhexanoate, 2-hydroxypropyl trimethylamnonium formate, and 2-hydroxypropyl trimethylammonium-2-ethylhexanoate). Preferred among these is 1,4-diazabicyclo[2.2.2]octane (DABCO). These known catalysts for polyurethane production can be used singly or in combination of two or more.

A polyurethane resin can be produced by reacting a polyol and a polyisocyanate in the presence of the catalyst for polyurethane production of the present invention.

The amount of the catalyst for polyurethane production of the present invention used is such that the amount of the amidate compound (1) is generally 0.001 to 10 parts by weight, and preferably 0.01 to 1 part by weight, based on 100 parts by weight of the polyol used.

In the method for producing a polyurethane resin of the present invention, the polyol is not particularly limited. Usable examples include conventionally known polyether polyols, polyester polyols, polymer polyols, and vegetable oil polyols; as well as fire-resistant polyols, such as phosphorus-containing polyol and halogen-containing polyol. These polyols may be used singly or in combination of two or more.

Polyether polyols are not particularly limited. Examples include those produced by addition reaction of compounds having at least two or more active hydrogen groups (specifically polyhydric alcohols, such as ethylene glycol, propylene glycol, glycerol, trimethylolpropane, and pentaerythritol; amines, such as ethylenediamine; and alkanolamines, such as ethanolamine and diethanolamine), which are used as starting materials, and alkylene oxides (specifically ethylene oxide, propylene oxide, etc.) (for example, see the method described in Gunter Oertel, Polyurethane Handbook (1985), Hanser Publishers (Germany), pp. 42-53).

Polyester polyols are not particularly limited. Examples include condensed reaction products of polyvalent carboxylic acids (e.g., adipic acid and phthalic acid) and polyhydric alcohols (e.g., ethylene glycol, 1,4-butanediol, and 1,6-hexanediol); and polyester polyols obtained by treating waste generated during nylon production, waste of trimethylolpropane or pentaerythritol, waste or waste products of phthalic acid-based polyester (for example, see Keiji Iwata, “Polyurethane Resin Handbook” (1987) Nikkan Kogyo Shimbun, Ltd., page 117).

Polymer polyols are not particularly limited. Examples include polymer polyols obtained by the reaction of the above polyether polyols and ethylenically unsaturated monomers (e.g., butadiene, acrylonitrile, and styrene) in the presence of a radical polymerization catalyst. Polymer polyols having a molecular weight of about 5000 to 12000 are particularly preferable.

Vegetable oil polyols are not particularly limited. Examples include hydroxyl group-containing vegetable oils, such as castor oil and coconut oil. Further, castor oil derivative polyols obtained using castor oil or hydrogenated castor oil as a raw material can also be suitably used. Examples of castor oil derivative polyols include castor oil polyester obtained by the reaction of castor oil, polyvalent carboxylic acid, and short-chain diol; alkylene oxide adducts of castor oil or castor oil polyesters; and the like.

Fire-resistant polyols are not particularly limited. Examples include phosphorus-containing polyols obtained by adding alkylene oxides to phosphoric acid compounds, halogen-containing polyols obtained by ring-opening polymerization of epichlorohydrin or trichlorobutylene oxide, aromatic ether polyols obtained by adding alkylene oxides to active hydrogen compounds having an aromatic ring, aromatic ester polyols obtained by condensation reaction of polyvalent carboxylic acids having an aromatic ring with polyhydric alcohols, and the like.

The hydroxyl value of the above polyols is preferably 5 to 300 mgKOH/g, and more preferably 10 to 250 mgKOH/g. The hydroxyl value can be measured by the method specified in JIS K0070.

The polyisocyanate is not particularly limited. Examples include aromatic, alicyclic, and aliphatic polyisocyanates having two or more isocyanate groups, and modified polyisocyanates thereof. Specific examples include aromatic polyisocyanates, such as tolylene diisocyanate, diphenylmethane diisocyanate, polymethylene polyphenyl polyisocyanate, phenylene diisocyanate, and xylylene diisocyanate; alicyclic polyisocyanates, such as dicyclohexyl diisocyanate and isophorone diisocyanate; aliphatic polyisocyanates, such as hexamethylene diisocyanate; prepolymer-modified products, nulete-modified products, and urea-modified products of the above polyisocyanates; and the like. These polyisocyanates may be used singly or in combination of two or more.

The amount of polyisocyanate used is not particularly limited, and is generally such that the isocyanate index (NCO concentration/active hydrogen group concentration× 100) is 70 to 140, preferably 75 to 130, and more preferably 80 to 120.

Moreover, from the viewpoint that an isocyanate component generated as a decomposed product when the amidate compound (1) acts as a catalyst is incorporated into the resin skeleton during production of polyurethane resins, and does not inhibit polymerization, it is preferable to use an amidate compound (1) of the formula (1) wherein n is 2 or more, for applications for which a higher degree of polymerization and crosslinking are required.

In the present invention, coloring agents, such as pigments and dyes, antioxidants, stabilizers, UV absorbers, flame retardants, inorganic fillers for increasing mechanical strength, organic solvents used to reduce viscosity, silane coupling agents, antifoaming agents, adhesion-imparting agents, such as leveling agents, and other additives can be added to the reaction of a polyol and a polyisocyanate, if necessary.

It is assumed that the amidate compound (1), which is a main component of the catalyst for polyurethane production of the present invention, is decomposed by heating to generate a carbene, and that the generated carbene functions as a catalyst for polyurethane production.

The amidate compound (1), which is a main component of the catalyst for polyurethane production of the present invention, functions as a thermally latent catalyst, as shown in Examples provided later. Therefore, the reaction according to the method for producing a polyurethane resin is preferably performed at 120° C. to 250° C., and more preferably 160° C. to 200° C.

A polyurethane resin can be obtained by the above method. The polyurethane resin obtained by the method of the present invention can be used for various applications, such as paints, adhesives, and sealing agents.

EXAMPLES

The present invention is described in detail below based on Examples; however, the present invention is not limited thereto. In the Examples, Bruker AV400 was used for $^1$H-NMR measurement, which was performed at 400 MHz.

Production Example 1-1: Synthesis of 1,3-dimethylimidazolium-2-carboxylate

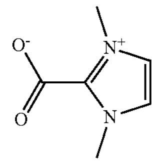

82.1 g (1.0 mol) of 1-methylimidazole, 119.8 g (1.0 mol) of dimethyl carbonate, and 83.1 g of methanol were placed in a 500-mL autoclave purged with nitrogen, and the obtained mixture was stirred at an internal temperature of 120° C. for 22 hours. The obtained reaction mixture was cooled to 25° C., and concentrated under reduced pressure, thereby obtaining a white solid. The obtained white solid was washed with toluene, and then dried under reduced pressure, thereby obtaining 47.8 g of a compound represented by the above formula (DMIm-$CO_2$) (yield: 34%). The $^1$H-NMR analysis results of DMIm-$CO_2$ are shown below.

$^1$H-NMR ($CD_3OD$) δ (ppm)=7.46 (s, 2H), 4.08 (s, 6H)

Production Example 2-1: Synthesis of 1-butyl-3-methylimidazolium-2-carboxylate

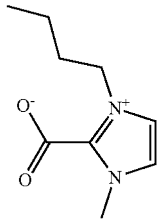

25.9 g (0.2 mol) of 1-butylimidazole, 25.0 g (0.3 mol) of dimethyl carbonate, and 26.2 g of methanol were placed in a 180-mL autoclave purged with nitrogen. The obtained mixture was stirred at 125° C. for 19 hours, and further stirred at 130° C. for 4 hours. The obtained reaction mixture was cooled to 25° C., thereby obtaining 73.0 g of a methanol solution of a compound represented by the above formula (hereinafter abbreviated as "BMIm-$CO_2$") (pure content: 34.3 g, yield: 95%). The $^1$H-NMR analysis results of the compound represented by the above formula are shown below.

$^1$H-NMR ($CD_3OD$) δ (ppm)=7.79 (s, 1H), 7.72 (s, 1H), 4.31 (t, J=7.4 Hz, 2H), 4.02 (s, 3H), 1.94-1.88 (m, 2H), 1.44-1.38 (m, 2H), 1.00 (t, J=7.2 Hz, 3H)

Production Example 2-2: Synthesis of 1-octyl-3-methyl-2-carboxylate

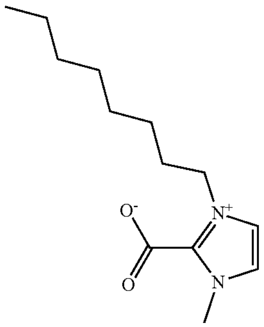 [SMILES: CCCCCCCC[n+]1ccn(C)c1C(=O)[O-]]

25.0 g (139 mmol) of 1-octylimidazole, 16.7 g (185 mmol) of dimethyl carbonate, and 25.1 g of methanol were placed in a 180-mL autoclave purged with nitrogen, and the obtained mixture was stirred at 125° C. for 29 hours. After the obtained mixture was cooled to room temperature, 8.5 g (94 mmol) of dimethyl carbonate was added, and the mixture was further stirred at 130° C. for 3 hours. The obtained reaction mixture was cooled to 25° C., thereby obtaining 44.0 g of a methanol solution of a compound represented by the above formula (hereinafter abbreviated as "OMIm-$CO_2$") (pure content: 33.0 g, yield: 99%). The $^1$H-NMR analysis results of the compound represented by the above formula are shown below.

$^1$H-NMR ($CD_3OD$) δ (ppm)=7.67 (s, 1H), 7.61 (s, 1H), 4.22 (t, J=7.2 Hz, 2H), 3.94 (s, 3H), 1.91-1.84 (m, 2H), 1.32-1.26 (m, 10H), 0.85 (t, J=7.2 Hz, 3H)

Production Example 2-3: Synthesis of p-chloro-N-t-butoxycarbonylaniline

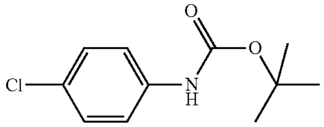

0.20 g (1.6 mmol) of p-chloroaniline, 0.17 g (1.7 mmol) of triethylamine, and 1 mL of tetrahydrofuran (THF) were placed in a 15-mL test tube purged with nitrogen. While stirring the mixture, 0.38 g (1.7 mmol) of di-t-butyl dicarbonate/1 mL of THF solution was added dropwise. The obtained mixture was stirred at 25° C. for 24 hours, and then further stirred at 40° C. for 18 hours. The obtained reaction mixture was cooled to 25° C., and dried under reduced pressure, thereby obtaining 0.30 g of a compound represented by the above formula (p-chloro-N-t-butoxycarbonylaniline) (yield: 83%). The $^1$H-NMR analysis results of the compound represented by the above formula are shown below.

$^1$H-NMR ($CDCl_3$) δ (ppm)=7.31 (d, J=8.8 Hz, 2H), 7.24 (d, J=8.8 Hz, 2H), 6.45 (s, 1H), 1.51 (s, 9H)

Production Example 2-4: Synthesis of m-chloro-N-t-butoxycarbonylaniline

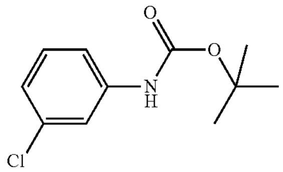

2.0 g (15.7 mmol) of m-chloroaniline, 1.8 g (17.3 mmol) of triethylamine, and 10 mL of THF were placed in a 100-mL test tube purged with nitrogen. While stirring the mixture, 3.4 g (15.7 mmol) of di-t-butyl dicarbonate/10 mL of THF solution was added dropwise. The obtained mixture was stirred at 25° C. for 4 hours, and then further stirred at 40° C. for 24 hours. After the obtained reaction mixture was cooled to 25° C., the solvent was distilled off. Then, 20 mL of toluene was added to the obtained concentrated residue, and the resulting mixture was washed once with 20 mL of 1 M citric acid aqueous solution and once with 20 mL of water. The obtained organic phase was dried over magnesium sulfate, and then dried under reduced pressure, thereby obtaining 1.4 g of a compound represented by the above formula (m-chloro-N-t-butoxycarbonylaniline) (yield: 39%). The $^1$H-NMR analysis results of the compound represented by the above formula are shown below.

$^1$H-NMR ($CDCl_3$) δ (ppm)=7.52 (s, 1H), 7.21-7.14 (m, 2H), 7.00 (dt, J=7.5, 1.7 Hz, 1H), 6.52 (s, 1H), 1.52 (s, 9H)

Production Example 2-5: Synthesis of p-isopropyl-N-t-butoxycarbonylaniline

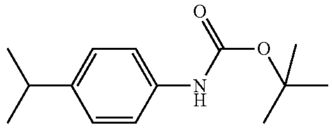 [SMILES: CC(C)c1ccc(NC(=O)OC(C)(C)C)cc1]

1.0 g (7.4 mmol) of p-isopropylaniline, 0.8 g (8.1 mmol) of triethylamine, and 5 mL of THF were placed in a 100-mL test tube purged with nitrogen. While stirring the mixture, 1.8 g (8.1 mmol) of di-t-butyl dicarbonate/5 mL of THF solution was added dropwise, and stirred at 25° C. for 17 hours. The solvent of the obtained reaction mixture was distilled off, and the resulting concentrated residue was washed with 5 mL of n-heptane. The obtained solid was dried under reduced pressure, thereby obtaining 1.9 g of a compound represented by the above formula (p-isopropyl-N-t-butoxycarbonylaniline) (yield: 67%). The $^1$H-NMR analysis results of the compound represented by the above formula are shown below.

$^1$H-NMR ($CDCl_3$) δ (ppm)=7.26 (d, J=8.3 Hz, 2H), 7.14 (d, J=8.3 Hz, 2H), 6.39 (s, 1H), 2.89-2.82 (m, 1H), 1.51 (s, 9H), 1.22 (d, J=6.8 Hz, 6H)

Production Example 2-6: Synthesis of p-octyl-N-t-butoxycarbonylaniline

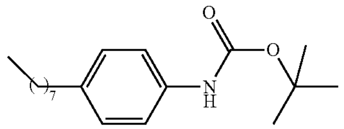 [SMILES: CCc1ccc(NC(=O)OC(C)(C)C)cc1]

2.0 g (9.7 mmol) of p-n-octylaniline, 1.1 g (10.7 mmol) of triethylamine, and 10 mL of THF were placed in a 100-mL test tube purged with nitrogen. While mixing the mixture, 2.3 g (10.7 m) of di-t-butyl dicarbonate/10 m L of THF solution was added dropwise, and stirred at 25° C. for 21 hours. The obtained reaction mixture was dried under reduced pressured, thereby obtaining 3.1 g of a compound represented by the above formula (p-octyl-N-t-butoxycarbonylaniline) (yield: 102%). The $^{1}$H-NMR analysis results of the compound represented by the above formula are shown below.

$^{1}$H-NMR ($CDCl_3$) δ (ppm)=7.26-7.24 (m, 2H), 7.09 (d, J=8.3 Hz, 2H), 6.39 (s, 1H), 2.54 (t, J=7.7 Hz, 2H), 1.53 (m, 2H), 1.51 (s, 9H), 1.28-1.26 (m, 10H), 0.87 (t, J=6.8 Hz, 3H)

Production Example 2-7: Synthesis of p-methoxy-N-t-butoxycarbonylaniline

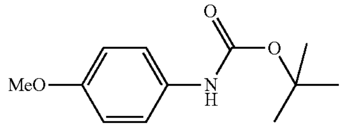 [SMILES: COc1ccc(NC(=O)OC(C)(C)C)cc1]

1.0 g (8.1 mmol) of p-anisidine, 0.9 g (8.9 mmol) of triethylamine, and 5 mL of THF were placed in a 100-mL test tube purged with nitrogen. While stirring the mixture, 2.0 g (8.9 mmol) of di-t-butyl dicarbonate/5 mL of THF solution was added dropwise, and stirred at 25° C. for 17 hours. The solvent of the obtained reaction mixture was distilled off, and the resulting concentrated residue was washed with 5 mL of heptane. After washing, the obtained solid was dried under reduced pressure, thereby obtaining 1.9 g of a compound represented by the above formula (p-methoxy-N-t-butoxycarbonylaniline) (yield: 85%). The $^{1}$H-NMR analysis results of the compound represented by the above formula are shown below.

$^{1}$H-NMR ($CDCl_3$) δ (ppm)=7.26 (d, J=8.8 Hz, 2H), 6.83 (d, J=8.8 Hz, 2H), 6.33 (s, 1H), 3.78 (s, 3H), 1.51 (s, 9H)

Production Example 2-8: Synthesis of p-vinyl-N-t-butoxycarbonylaniline

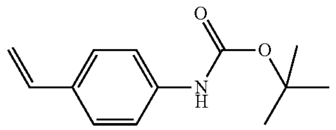 [SMILES: C=Cc1ccc(NC(=O)OC(C)(C)C)cc1]

1.0 g (8.5 mmol) of p-vinylaniline, 0.9 g (9.2 mmol) of triethylamine, and 10 mL of THF were placed in a 50-mL test tube purged with nitrogen, and the resulting mixture was cooled to 0° C. While stirring the mixture, 2.0 g (9.3 mmol) of di-t-butyl dicarbonate/10 mL of THF solution was added dropwise, stirred at 0° C. for 90 hours, and then stirred at 30° C. for 21.5 hours. 0.4 g (4.2 mmol) of diethanolamine was added dropwise to the obtained mixture. After stirring for 1 hour, the obtained reaction mixture was dried under reduced pressure. 20 mL of toluene and 10 mL of water were added to the obtained concentrated residue, and liquid separation was performed. The obtained organic phase was dried under reduced pressure, thereby obtaining 1.8 g of a compound represented by the above formula (p-vinyl-N-t-butoxycarbonylaniline) (yield: 96%). The $^{1}$H-NMR analysis results of the compound represented by the above formula are shown below.

$^{1}$H-NMR (DMSO-d6) δ (ppm)=9.42 (s, 1H), 7.44-7.34 (m, 4H), 6.67-6.60 (m, 1H), 5.71-5.66 (m, 1H), 5.14-5.11 (m, 1H), 1.47 (s, 9H)

Production Example 2-9: Synthesis of 2,6-diisopropyl-N-t-butoxycarbonylaniline

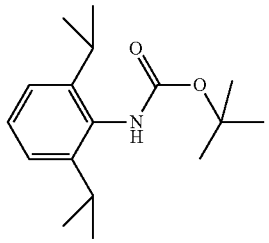 [SMILES: CC(C)c1cccc(C(C)C)c1NC(=O)OC(C)(C)C]

1.0 g (5.6 mmol) of 2,6-diisopropylaniline, 0.6 g (5.6 mmol) of triethylamine, and 5 mL of THF were placed in a 100-mL test tube purged with nitrogen. While stirring the mixture, 1.2 g (5.6 mmol) of di-t-butyl dicarbonate/5 mL of THF solution was added dropwise, and stirred at 25° C. for 21 hours. After the solvent of the obtained reaction mixture was distilled off, 10 mL of toluene was added to the obtained concentrated residue, washed with 15 mL of acetic acid solution (1 g/15 mL) and 10 mL of water, and dried over magnesium sulfate. The obtained organic phase was dried under reduced pressure, thereby obtaining 1.1 g of a compound represented by the above formula (2,6-diisopropyl-N-t-butoxycarbonylaniline) (yield: 71%). The $^{1}$H-NMR analysis results of the compound represented by the above formula are shown below. The $^{1}$H-NMR analysis results showed that this compound was a mixture of rotamers.

$^{1}$H-NMR ($CDCl_3$) δ (ppm)=7.26 (m, 1H), 7.14 (d, J=7.1 Hz, 2H), 5.81 (s, 0.7H), 5.58 (s, 0.3H), 3.18-3.17 (m, 2H), 1.51 (s, 6H), 1.37 (s, 3H), 1.21 (d, J=6.8 Hz, 12H)

Production Example 2-10: Synthesis of N-t-butoxycarbonylbenzylamine

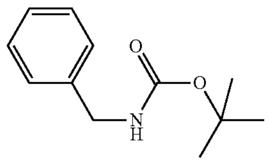

3.1 g (14.0 mmol) of di-t-butyl dicarbonate, 1.6 g (15.4 mol) of triethylamine, and 10 mL of THF were placed in a 50-mL test tube purged with nitrogen, and a mixture of 1.5 g (14.0 mmol) of benzylamine and 5 mL of THF was added dropwise. After the obtained mixture was stirred at 25° C. for 3 hours, 0.2 g (1.8 mmol) of benzylamine was further added, and the mixture was stirred for 15 hours. After the obtained reaction mixture was concentrated under reduced pressure, liquid separation operation was carried out, and the obtained organic phase was concentrated under reduced pressure, thereby obtaining 2.8 g (yield: 93%) of a compound represented by the above formula (N-t-butoxycarbonylbenzylamine). The $^{1}$H-NMR analysis results of the compound represented by the above formula are shown below.

$^{1}$H-NMR ($CDCl_3$) δ (ppm)=7.35-7.26 (m, 5H), 4.83 (br, 1H), 4.32-4.31 (m, 2H), 1.46 (s, 9H)

Production Example 2-11: Synthesis of p-vinyl-N-t-butoxycarbonylbenzylamine

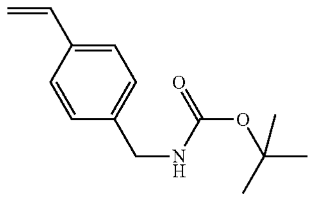 [SMILES: C=Cc1ccc(CNC(=O)OC(C)(C)C)cc1]

1.0 g (7.7 mmol) of p-vinylbenzylamine, 0.8 g (8.2 mmol) of triethylamine, and 10 mL of THF were placed in a 50-mL test tube purged with nitrogen, and the resulting mixture was cooled to 0° C. While stirring the mixture, 1.8 g (8.3 mmol) of di-t-butyl dicarbonate/10 mL of THF solution was added dropwise, and stirred at 25° C. for 47 hours. 0.5 g (4.8 mmol) of diethanolamine was added dropwise to the obtained mixture. After stirring for 1 hour, the obtained reaction mixture was dried under reduced pressure. 20 mL of toluene and 10 mL of water were added to the obtained concentrated residue, and liquid separation was performed. The obtained organic phase was dried under reduced pressure, thereby obtaining 1.8 g of a compound represented by the above formula (p-vinyl-N-t-butoxycarbonylbenzylamine) (yield: 101%). The $^{1}$H-NMR analysis results of the compound represented by the above formula are shown below.

$^{1}$H-NMR (DMSO-d6) δ (ppm)=7.42-7.19 (m, 5H), 6.74-6.67 (m, 1H), 5.82-5.77 (m, 1H), 5.23-5.21 (m, 1H), 4.10 (d, J=5.6 Hz, 2H), 1.39 (s, 9H)

Production Example 2-12: Synthesis of 1,4-bis{2-[4-(t-butoxycarbonylamino)phenyl]-2-propyl}benzene

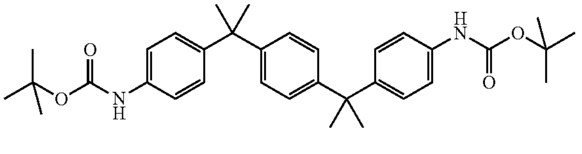 [SMILES: CC(C)(C)OC(=O)Nc1ccc(C(C)(C)c2ccc(C(C)(C)c3ccc(NC(=O)OC(C)(C)C)cc3)cc2)cc1]

2.4 g (11.1 mmol) of di-t-butyl dicarbonate, 1.3 g (12.8 mmol) of triethylamine, and 15 mL of THF were placed in a 50-mL test tube purged with nitrogen. A mixture of 2.0 g (5.8 mmol) of 1,4-bis[2-(4-aminophenyl)-2-propyl]benzene and 5 mL of THF was added dropwise, and stirred at 25° C. for 19 hours. The obtained reaction mixture was dried under reduced pressure, thereby obtaining a mixture of a compound represented by the above formula (1,4-bis{2-[4-(t-butoxycarbonylamino)phenyl]-2-propyl}benzene), and unreacted 1-{2-[4-(t-butoxycarbonylamino)phenyl]-2-propyl}-4-[2-(4-aminophenyl)-2-propyl]benzene. Part of the obtained mixture was sampled, and di-t-butyl dicarbonate was added. After stirring for 3 hours, diethanolamine was added. After concentration under reduced pressure, liquid separation operation was carried out, and the obtained organic phase was concentrated under reduced pressure, thereby obtaining a compound represented by the above formula. The $^{1}$H-NMR analysis results of the compound represented by the above formula are shown below.

$^{1}$H-NMR ($CDCl_3$) δ (ppm)=7.26-7.22 (m, 4H), 7.15-7.13 (m, 4H), 7.08-7.07 (m, 4H), 6.40 (br, 2H), 1.62 (s, 12H), 1.50 (s, 18H)

Production Example 2-13: Synthesis of 1,3-bis{2-[4-(t-butoxycarbonylamino)phenyl]-2-propyl}benzene

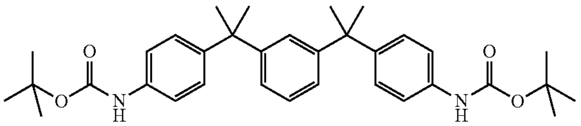 [SMILES: CC(C)(C)OC(=O)Nc1ccc(C(C)(C)c2cccc(C(C)(C)c3ccc(NC(=O)OC(C)(C)C)cc3)c2)cc1]

12.7 g (58 mmol) of di-t-butyl dicarbonate, 3.3 g (33 mmol) of triethylamine, and 25.0 g of THF were placed in a 200-mL test tube purged with nitrogen. To the resulting mixture, a mixture of 5.0 g (14.5 mmol) of 4,4-(1,3-phenylenediisopropylidene)bisaniline and 30.0 g of THF was added dropwise over 5 minutes. The mixture was stirred at 25° C. for 4 hours. To the mixture cooled to 0° C., 3.1 g (290 mmol) of diethanolamine was added over 10 minutes. After the resulting mixture was concentrated under reduced pressure, 200 mL of ethyl acetate was added to the obtained concentrated residue, and washed 3 times with 100 mL of water. To the ethyl acetate phase after washing, magnesium sulfate was added for drying, and the magnesium sulfate was then removed by filtration. The obtained filtrate was concentrated, thereby obtaining 6.3 g of a compound represented by the above formula (1,3-bis{2-[4-(t-butoxycarbonylamino)phenyl]-2-propyl}benzene) (yield: 80%). The $^{1}$H-NMR analysis results of the compound represented by the above formula are shown below.

$^{1}$H-NMR (DMSO-d6) δ (ppm)=9.22 (s, 2H), 7.31 (d, J=8.6 Hz, 4H), 7.12 (t, J=7.7 Hz, 1H), 7.14-7.03 (m, 5H), 6.94 (d, J=7.7 Hz, 2H), 3.34 (s, 12H), 1.45 (s, 18H)

Production Example 2-14: Synthesis of 1,3-bis[4-(t-butoxycarbonylamino)phenoxy]benzene

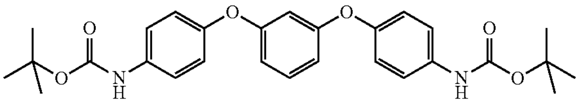 [SMILES: CC(C)(C)OC(=O)Nc1ccc(Oc2cccc(Oc3ccc(NC(=O)OC(C)(C)C)cc3)c2)cc1]

7.5 g (34.3 mmol) of di-t-butyl dicarbonate, 1.7 g (17.2 mmol) of triethylamine, and 40 mL of THF were placed in a 200-mL three-necked flask purged with nitrogen, and a mixture of 5.0 g (17.2 mmol) of 1,3-bis(4-aminophenoxy) benzene and 10 mL of THF was added dropwise. After the obtained mixture was stirred at 25° C. for 6 hours, 3.8 g (17.4 mmol) of di-t-butyl dicarbonate was added, and the resulting mixture was further stirred for 3 hours. Then, 2.8 g (26.3 mmol) of diethanolamine was added to the obtained reaction mixture. After concentration under reduced pressure, liquid separation operation was carried out, and the obtained organic phase was concentrated under reduced pressure, thereby obtaining 8.0 g of a compound represented by the above formula (1,3-bis[4-(t-butoxycarbonylamino) phenoxy]benzene) (yield: 94%). The $^1$H-NMR analysis results of the compound represented by the above formula are shown below.

$^1$H-NMR ($CD_3OD$) δ (ppm)=7.38 (d, J=8.8 Hz, 4H), 7.23 (t, J=8.4 Hz, 1H), 6.93 (d, J=8.8 Hz, 4H), 6.40 (dd, J=8.4, 2.2 Hz, 2H), 6.50 (d, J=2.2 Hz, 1H), 1.51 (s, 18H)

Production Example 2-15: Synthesis of bis[3-(t-butoxycarbonylamino)phenyl]sulfone

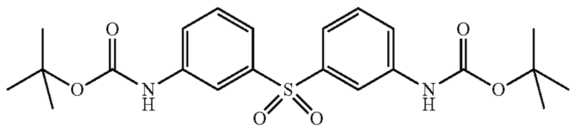 [SMILES: CC(C)(C)OC(=O)Nc1cccc(S(=O)(=O)c2cccc(NC(=O)OC(C)(C)C)c2)c1]

2.0 g (8.1 mmol) of bis(3-aminophenyl)sulfone, 2.0 g (16.1 mmol) of di-t-butyl dicarbonate, and 20 mL of THF were placed in a 100-mL test tube purged with nitrogen. While stirring the mixture, 1.8 g (17.7 mmol) of triethylamine was added dropwise. The obtained mixture was stirred at 25° C. for 6 hours, and then further stirred at 40° C. for 16 hours. Thereafter, 5.5 g (25.2 mmol) of di-t-butyl dicarbonate was added, and further stirred at 40° C. for 48 hours. 1.7 g (15.9 mmol) of diethanolamine was added dropwise to the obtained mixture. After stirring for 1 hour, the obtained reaction mixture was dried under reduced pressure. 15 mL of ethyl acetate and 15 mL of water were added to the obtained concentrated residue, and liquid separation was performed. The obtained organic phase was dried over magnesium sulfate, and then dried under reduced pressure, thereby obtaining 3.5 g of a compound represented by the above formula (bis[3-(t-butoxycarbonylamino)phenyl]sulfone) (yield: 93%). The $^1$H-NMR analysis results of the compound represented by the above formula are shown below.

$^1$H-NMR ($CDCl_3$) δ (ppm)=7.86 (s, 2H), 7.68 (d, J=7.3 Hz, 2H), 7.58 (d, J=7.3 Hz, 2H), 7.43-7.39 (m, 2H), 6.67 (s, 2H), 1.51 (s, 18H)

Production Example 2-16: Synthesis of o-chloro-N-t-butoxycarbonylaniline

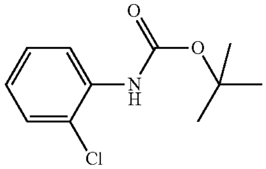

1.0 g (6.5 mmol) of o-chlorophenyl isocyanate and 2.0 g (27.0 mmol) of 2-methyl-2-propanol were placed in a 15-mL test tube purged with nitrogen, and stirred at 90° C. for 3 hours. After the obtained reaction mixture was cooled to 25° C., the solvent was distilled off. The obtained concentrated residue was dissolved in chloroform, and insoluble substances were removed by filtration. The obtained filtrate was dried under reduced pressure, thereby obtaining 1.0 g of a compound represented by the above formula (o-chloro-N-t-butoxycarbonylaniline) (yield: 64%). The $^1$H-NMR analysis results of the compound represented by the above formula are shown below.

$^1$H-NMR ($CDCl_3$) δ (ppm)=8.16 (d, J=8.2 Hz, 1H), 7.33 (dd, J=8.2, 1.4 Hz, 1H), 7.24 (t, J=7.7 Hz, 1H), 7.01 (s, 1H), 6.96 (td, J=7.7, 1.4 Hz, 1H), 1.53 (s, 9H)

Production Example 2-17: Synthesis of bis[4-(t-butoxycarbonylamino)phenyl]methane

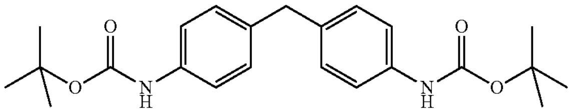 [SMILES: CC(C)(C)OC(=O)Nc1ccc(Cc2ccc(NC(=O)OC(C)(C)C)cc2)cc1]

15.0 g (60 mmol) of 4,4'-methylenediphenyl diisocyanate, 22.2 g (300 mmol) of 2-methyl-2-propanol, and 44 g of toluene were placed in a 200-mL test tube purged with nitrogen, and stirred at 85° C. for 3 hours. The obtained reaction mixture was concentrated under reduced pressure, thereby obtaining 22.8 g of a compound represented by the above formula (bis[4-(t-butoxycarbonylamino)phenyl] methane) (yield: 96%). The $^1$H-NMR analysis results of the compound represented by the above formula are shown below.

$^1$H-NMR (DMSO-d6) δ (ppm)=9.23 (s, 2H) 7.34 (d, J=8.6 Hz, 4H), 7.05 (d, J=8.6 Hz, 4H), 3.76 (s, 2H), 1.45 (s, 18H)

Production Example 2-18: Synthesis of p-chloro-N-methoxycarbonylaniline

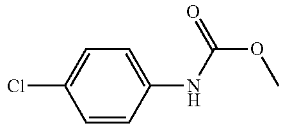

1.0 g (6.6 mmol) of p-chlorophenyl isocyanate and 20 mL of methanol were placed in a 50-mL test tube purged with nitrogen, and stirred at 70° C. for 3 hours. The obtained reaction mixture was dried under reduced pressure, thereby obtaining 1.4 g (yield: 91%) of a compound represented by the above formula (p-chloro-N-methoxycarbonylaniline). The $^1$H-NMR analysis results of the compound represented by the above formula are shown below.

$^1$H-NMR (DMSO-d6) δ (ppm)=9.79 (br, 1H), 7.47 (d, J=8.8 Hz, 2H), 7.33 (d, J=8.8 Hz, 2H), 3.66 (s, 3H)

Production Example 2-19: Synthesis of p-chloro-N-isopropoxycarbonylaniline

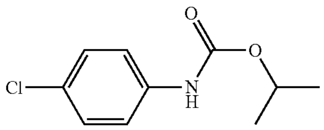

1.0 g (6.5 mmol) of p-chlorophenyl isocyanate and 2.0 g (33.3 mmol) of isopropanol were placed in a 15-mL test tube purged with nitrogen, and stirred at 90° C. for 3 hours. The obtained reaction mixture was cooled to 25° C., and then dried under reduced pressure, thereby obtaining 1.0 g of a compound represented by the above formula (p-chloro-N-isopropoxycarbonylaniline) (yield: 64%). The $^1$H-NMR analysis results of the compound represented by the above formula are shown below.

$^1$H-NMR ($CDCl_3$) δ (ppm)=7.33 (d, J=8.6 Hz, 2H), 7.26 (d, J=9.1 Hz, 2H), 6.50 (s, 1H), 5.04-4.98 (m, 1H), 1.30 (d, J=6.3 Hz, 6H)

Production Example 2-20: Synthesis of p-chloro-N-octoxycarbonylaniline (p-chloro-N-(n-octyloxy) carbonylaniline)

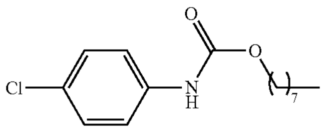

1.0 g (6.5 mmol) of p-chlorophenyl isocyanate, 0.9 g (6.5 mmol) of n-octanol, and 2.5 mL of toluene were placed in a 15-mL test tube purged with nitrogen, and stirred at 110° C. for 3 hours. The obtained reaction mixture was cooled to 25° C., and then dried under reduced pressure, thereby obtaining 1.8 g of a compound represented by the above formula (p-chloro-N-octoxycarbonylaniline (p-chloro-N-(n-octyloxy)carbonylaniline)) (yield: 95%). The $^1$H-NMR analysis results of the compound represented by the above formula are shown below.

$^1$H-NMR ($CDCl_3$) δ (ppm)=7.33 (d, J=8.6 Hz, 2H), 7.27-7.24 (m, 2H), 6.62 (s, 1H), 4.14 (t, J=6.7 Hz, 2H), 1.69-1.62 (m, 2H), 1.36-1.29 (m, 10H), 0.88 (t, J=6.8 Hz, 3H)

Production Example 2-21: Synthesis of p-chloro-N-phenoxycarbonylaniline

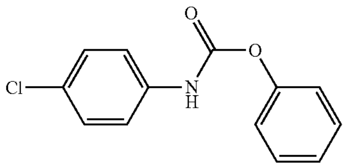 [SMILES: O=C(Nc1ccc(Cl)cc1)Oc1ccccc1]

1.0 g (6.5 mmol) of p-chlorophenyl isocyanate, 0.6 g (6.5 mmol) of phenol, and 2.5 mL of toluene were placed in a 15-mL test tube purged with nitrogen, and stirred at 110° C. for 3 hours. The obtained reaction mixture was cooled to 25° C., and then dried under reduced pressure, thereby obtaining 1.5 g of a compound represented by the above formula (p-chloro-N-phenoxycarbonylaniline) (yield: 93%). The $^1$H-NMR analysis results of the compound represented by the above formula are shown below.

$^1$H-NMR ($CDCl_3$) δ (ppm)=7.41-7.39 (m, 4H), 7.28-7.25 (m, 3H), 7.18 (d, J=7.6 Hz, 2H), 6.97 (s, 1H)

Synthesis Example 1-1: Synthesis of DMIm-PI

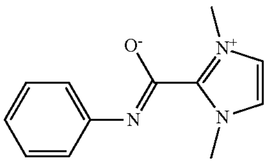 [SMILES: Cn1cc[n+](C)c1/C([O-])=N/c1ccccc1]

3.0 g (21 mmol) of DMIm-$CO_2$ obtained in Production Example 1-1, 100 mL of toluene, and 2.5 g (21 mmol) of phenyl isocyanate were placed in a three-necked flask purged with nitrogen. The obtained mixture was stirred at an internal temperature of 110° C. for 3 hours. The obtained reaction mixture was cooled to 25° C., and concentrated under reduced pressure, thereby obtaining 5.3 g (pure content: 4.9 g) of a compound represented by the above formula (DMIm-PI) (yield: 97%). The $^1$H-NMR analysis results of DMIm-PI are shown below.

$^1$H-NMR ($CD_3OD$) δ (ppm)=7.45 (m, 2H), 7.35-7.27 (m, 4H), 7.00 (m, 1H), 3.98 (s, 6H)

Synthesis Example 1-2: Synthesis of DMIm-pClPI

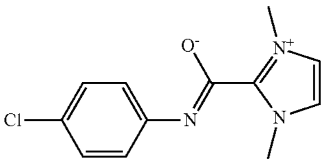 [SMILES: Cn1cc[n+](C)c1/C([O-])=N/c1ccc(Cl)cc1]

3.0 g (21 mmol) of DMIm-$CO_2$ obtained in Production Example 1-1, 100 mL of toluene, and 3.3 g (21 mmol) of p-chlorophenyl isocyanate were placed in a three-necked flask purged with nitrogen. The obtained mixture was stirred at an internal temperature of 110° C. for 3 hours. After the obtained reaction mixture was cooled to 25° C., filtration was performed, and the obtained yellow solid was dried under reduced pressure, thereby obtaining 4.6 g of a compound represented by the above formula (DMIm-pClPI) (yield: 88%). The $^1$H-NMR analysis results of DMIm-pClPI are shown below.

$^1$H-NMR ($CD_3OD$) δ (ppm)=7.47 (s, 2H), 7.39 (m, 2H), 7.25 (m, 2H), 3.99 (s, 6H)

Synthesis Example 1-3: Synthesis of DMIm-BI

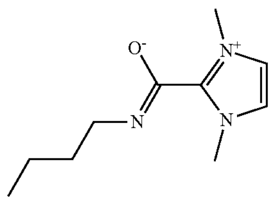

3.0 g (21 mmol) of DMIm-$CO_2$ obtained in Production Example 1-1, 100 mL of toluene, and 2.1 g (21 mmol) of n-butyl isocyanate were placed in a three-necked flask purged with nitrogen. The obtained mixture was stirred at an internal temperature of 110° C. for 3 hours. After the obtained reaction mixture was cooled to 25° C., filtration was performed, and the obtained filtrate was concentrated under reduced pressure, thereby obtaining 3.5 g of a compound represented by the above formula (DMIm-BI) (yield: 82%).

Synthesis Example 1-4: Synthesis of DMIm-TDI

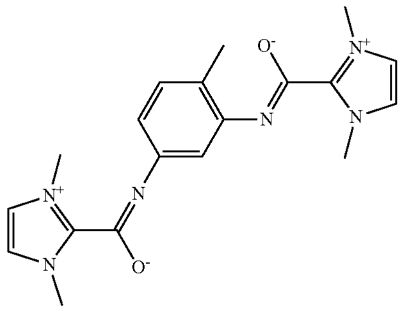 [SMILES: Cc1ccc(N=C([O-])c2n(C)cc[n+]2C)cc1/N=C(\[O-])c1n(C)cc[n+]1C]

3.8 g (27 mmol) of DMIm-$CO_2$ obtained in Production Example 1-1, 100 mL of toluene, and 2.4 g (13 mmol) of 2,4-tolylene diisocyanate were placed in a three-necked flask purged with nitrogen. The obtained mixture was stirred at an internal temperature of 110° C. for 3 hours. After the obtained reaction mixture was cooled to 25° C., filtration was performed, and the obtained yellow solid was dried under reduced pressure, thereby obtaining 5.3 g of a compound represented by the above formula (DMIm-TDI) (yield: 87%).

Synthesis Example 2-1: Synthesis of DMIm-BI 2.1 g (15 mmol) of DMIm-$CO_2$ obtained in Production Example 1-1, 20 mL of chlorobenzene, and 0.3 g (3.0 mmol) of n-butyl isocyanate were placed in a three-necked flask purged with nitrogen, and the obtained mixture was stirred at 130° C. for 2 hours. After the obtained reaction mixture was cooled to 25° C., 2.7 g (27 mol) of n-butyl isocyanate was added, and further stirred at 130° C. for 2 hours. After the obtained reaction mixture was cooled to 25° C., filtration was performed, and the obtained filtrate was concentrated under reduced pressure. 30 mL of toluene and 30 mL of water were added to the obtained concentrated residue, and liquid separation was performed. The obtained aqueous phase was washed twice with 30 mL of toluene, and then concentrated under reduced pressure, thereby obtaining 1.9 g of DMIm-BI (yield: 64%). The $^1$H-NMR analysis results of DMIm-BI are shown below.

$^1$H-NMR ($CD_3OD$) δ (ppm)=7.43 (s, 2H), 3.87 (s, 6H), 3.37 (t, J=7.2 Hz, 2H), 1.59 (quint, J=7.2 Hz, 2H), 1.44 (sext, J=7.2 Hz, 2H), 0.97 (t, J=7.2 Hz, 3H)

Synthesis Example 2-2: Synthesis of DMIm-pClPI 0.31 g (2.2 mmol) of DMIm-$CO_2$ obtained in Production Example 1-1, 0.51 g (2.2 mmol) of p-chloro-N-t-butoxycarbonylaniline obtained in Production Example 2-3, and 17 mL of toluene were placed in a three-necked flask purged with nitrogen, and the resulting mixture was stirred at 110° C. for 3 hours. The obtained reaction mixture was cooled to 25° C., and then concentrated under reduced pressure, thereby obtaining 0.31 g of DMIm-pClPI (yield: 97%).

Synthesis Example 2-3: Synthesis of DMIm-mClPI

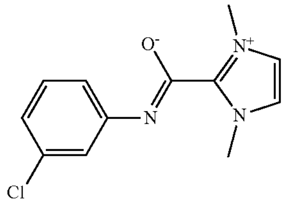 [SMILES: Cn1cc[n+](C)c1/C([O-])=N/c1cccc(Cl)c1]

0.31 g (2.24 mmol) of DMIm-$CO_2$ obtained in Production Example 1-1, 0.51 g (2.23 mmol) of m-chloro-N-t-butoxycarbonylaniline obtained in Production Example 2-4, and 9 mL of toluene were placed in a 30-mL test tube purged with nitrogen, and the resulting mixture was stirred at 110° C. for 3 hours. After the obtained reaction mixture was cooled to 25° C., filtration was performed, and the obtained white solid was dried under reduced pressure, thereby obtaining 0.44 g of a compound represented by the above formula (DMIm-mClPI) (yield: 80%). The $^1$H-NMR analysis results of DMIm-mClPI are shown below.

$^1$H-NMR (DMSO-d6) δ (ppm)=7.78 (t, J=2.0 Hz, 1H), 7.55 (s, 2H), 7.26 (d, J=9.6 Hz, 1H), 7.13 (t, J=8.0 Hz, 1H), 6.81 (d, J=7.8 Hz, 1H), 4.00 (s, 6H)

Synthesis Example 2-4: Synthesis of DMIm-oClPI

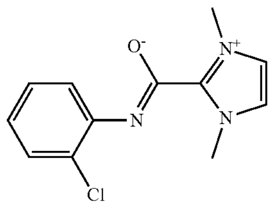 [SMILES: Cn1cc[n+](C)c1/C([O-])=N/c1ccccc1Cl]

0.31 g (2.20 mmol) of DMIm-$CO_2$ obtained in Production Example 1-1, 0.50 g (2.20 mmol) of o-chloro-N-t-butoxycarbonylaniline obtained in Production Example 2-16, and 9 mL of toluene were placed in a 30-mL test tube purged with nitrogen, and the resulting mixture was stirred at 110° C. for 6 hours. After the obtained reaction mixture was cooled to 25° C., filtration was performed, and the obtained white solid was dried under reduced pressure, thereby obtaining 0.47 g of a compound represented by the above formula (DMIm-oClPI) (yield: 85%). The $^1$H-NMR analysis results of DMIm-oClPI are shown below.

$^1$H-NMR (DMSO-d6) δ (ppm)=7.93 (d, J=7.8 Hz, 1H), 7.57 (s, 2H), 7.28 (d, J=7.8 Hz, 1H), 7.09 (t, J=8.0 Hz, 1H), 6.79 (t, J=7.6 Hz, 1H), 4.09 (s, 6H)

Synthesis Example 2-5: Synthesis of DMIm-piPrPI

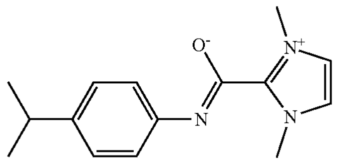 [SMILES: CC(C)c1ccc(/N=C(\[O-])c2n(C)cc[n+]2C)cc1]

0.20 g (1.43 mmol) of DMIm-$CO_2$ obtained in Production Example 1-1, 0.34 g (1.43 mmol) of p-isopropyl-N-t-butoxycarbonylaniline obtained in Production Example 2-5, and 6 mL of toluene were placed in a 15-mL test tube purged with nitrogen, and the resulting mixture was stirred at 110° C. for 18 hours. After the obtained reaction mixture was cooled to 25° C., the solvent was distilled off under reduced pressure. 8 mL of toluene and 2 mL of water were added to the residue after distilling off the solvent, the resulting mixture was stirred at room temperature for 5 minutes, and the aqueous phase and the organic phase were separated. The obtained aqueous phase was dried under reduced pressure, thereby obtaining 0.26 g of a compound represented by the above formula (DMIm-piPrPI) (yield: 67%). The $^1$H-NMR analysis results of DMIm-piPrPI are shown below.

$^1$H-NMR (DMSO-d6) δ (ppm)=7.51 (s, 2H), 7.40 (d, J=8.3 Hz, 2H), 6.99 (d, J=8.3 Hz, 2H), 3.99 (s, 6H), 2.81-2.74 (m, 1H), 1.16 (d, J=6.8 Hz, 6H)

Synthesis Example 2-6: Synthesis of DMIm-pOctPI

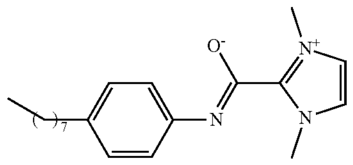

0.23 g (1.64 mmol) of DMIm-$CO_2$ obtained in Production Example 1-1, 0.50 g (1.64 mmol) of p-octyl-N-t-butoxycarbonylaniline obtained in Production Example 2-6, and 6 mL of toluene were placed in a 15-mL test tube purged with nitrogen, and the resulting mixture was stirred at 110° C. for 9 hours. The obtained reaction mixture was cooled to 25° C., and then dried under reduced pressure, thereby obtaining 0.51 g of a compound represented by the above formula (DMIm-pOctPI) (yield: 98%). The $^1$H-NMR analysis results of DMIm-pOctPI are shown below.

$^1$H-NMR (DMSO-d6) δ (ppm)=7.51 (s, 2H), 7.40 (d, J=8.3 Hz, 2H), 6.93 (d, J=8.3 Hz, 2H), 3.98 (s, 6H), 2.46 (t, J=7.6 Hz, 2H), 1.51 (bs, 2H), 1.24 (s, 10H), 0.85 (t, J=6.8 Hz, 3H)

Synthesis Example 2-7: Synthesis of DMIm-pMeOPI

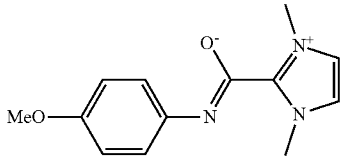 [SMILES: COc1ccc(/N=C(\[O-])c2n(C)cc[n+]2C)cc1]

0.31 g (2.24 mmol) of DMIm-$CO_2$ obtained in Production Example 1-1, 0.50 g (2.24 mmol) of p-methoxy-N-t-butoxycarbonylaniline obtained in Production Example 2-7, and 9 mL of toluene were placed in a 30-mL test tube purged with nitrogen, and the resulting mixture was stirred at 110° C. for 12 hours. After the obtained reaction mixture was cooled to 25° C., filtration was performed, and the obtained white solid was dried under reduced pressure, thereby obtaining 0.43 g of a compound represented by the above formula (DMIm-pMeOPI) (yield: 79%). The $^1$H-NMR analysis results of DMIm-pMeOPI are shown below.

$^1$H-NMR (DMSO-d6) δ (ppm)=7.50-7.49 (m, 4H), 6.71 (d, J=9.1 Hz, 2H), 3.99 (s, 6H), 3.68 (s, 3H)

Synthesis Example 2-8: Synthesis of DMIm-pVPI

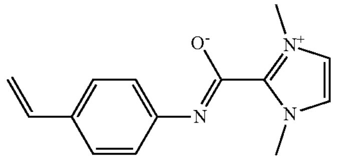 [SMILES: C=Cc1ccc(/N=C(\[O-])c2n(C)cc[n+]2C)cc1]

0.14 g (0.98 mmol) of DMIm-$CO_2$ obtained in Production Example 1-1, 0.21 g (0.94 mol) of p-vinyl-N-t-butoxycarbonylaniline obtained in Production Example 2-8, and 40 mL of chlorobenzene were placed in a 50-mL test tube purged with nitrogen, and stirred at 130° C. for 2.5 hours. After the obtained reaction mixture was cooled to 25° C., filtration was performed, and the obtained filtrate was concentrated under reduced pressure. The obtained concentrate was mixed with methanol, filtration was performed, and the obtained filtrate was concentrated under reduced pressure, thereby obtaining 0.19 g of a compound represented by the above formula (DMIm-pVPI) (yield: 84%). The $^1$H-NMR analysis results of DMIm-pVPI are shown below.

$^1$H-NMR (DMSO-d6) δ (ppm)=7.56 (s, 2H), 7.52-7.25 (m, 4H), 6.64 (dd, J=17.2, 10.8 Hz, 1H), 5.62 (dd, J=18.0, 1.2 Hz, 1H), 5.05 (dd, J=10.8, 1.2 Hz, 1H), 4.01 (s, 6H)

Synthesis Example 2-9: Synthesis of DMIm-26iPrPI

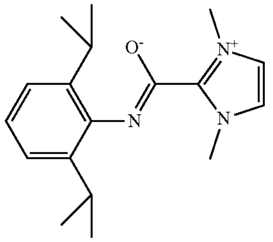 [SMILES: CC(C)c1cccc(C(C)C)c1/N=C(\[O-])c1n(C)cc[n+]1C]

0.25 g (1.80 mmol) of DMIm-$CO_2$ obtained in Production Example 1-1, 0.50 g (1.80 mmol) of 2,6-diisopropyl-N-t-butoxycarbonylaniline obtained in Production Example 2-9, and 6 mL of toluene were placed in a 15-mL test tube purged with nitrogen, and the resulting mixture was stirred at 110° C. for 12 hours. After the obtained reaction mixture was cooled to 25° C., filtration was performed, and the obtained white solid was dried under reduced pressure, thereby obtaining 0.46 g of a compound represented by the above formula (DMIm-26iPrPI) (yield: 83%). The $^1$H-NMR analysis results of DMIm-26iPrPI are shown below.

$^1$H-NMR (DMSO-d6) δ (ppm)=7.54 (s, 2H), 6.94 (d, J=7.6 Hz, 2H), 6.81 (t, J=7.5 Hz, 1H), 4.01 (s, 6H), 3.20-3.13 (m, 2H), 1.10 (d, J=6.8 Hz, 12H)

Synthesis Example 2-10: Synthesis of DMIm-BnI

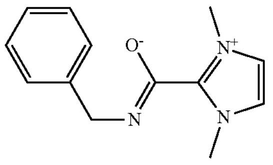 [SMILES: Cn1cc[n+](C)c1/C([O-])=N/Cc1ccccc1]

0.52 g (3.68 mmol) of DMIm-$CO_2$ obtained in Production Example 1-1, 0.63 g (3.03 mol) of N-t-butoxycarbonylbenzylamine, and 15 mL of chlorobenzene were placed in a 100-mL test tube purged with nitrogen, and the resulting mixture was stirred at 130° C. for 3 hours. After the obtained reaction mixture was cooled to 25° C., filtration was performed, and the solvent of the obtained filtrate was distilled off under reduced pressure. 15 mL toluene and 50 mL of water were added to the residue after distilling off the solvent, the resulting mixture was stirred at room temperature for 5 minutes, and the aqueous phase and the organic phase were separated. The obtained aqueous phase was dried under reduced pressure, thereby obtaining 0.27 g of a compound represented by the above formula (DMIm-BnI) (yield: 28%). The $^1$H-NMR analysis results of DMIm-BnI are shown below.

$^1$H-NMR (DMSO-d6) δ (ppm)=7.48 (s, 2H), 7.34 (d, J=7.6 Hz, 2H), 7.24 (t, J=8.0 Hz, 2H), 7.12 (t, J=7.3 Hz, 1H), 4.40 (s, 2H), 3.97 (s, 6H)

Synthesis Example 2-11: Synthesis of DMIm-pVPMI

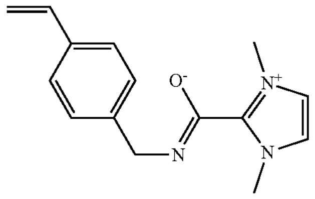 [SMILES: C=Cc1ccc(C/N=C(\[O-])c2n(C)cc[n+]2C)cc1]

0.24 g (1.74 mmol) of DMIm-$CO_2$ obtained in Production Example 1-1, 0.20 g (0.86 mmol) of p-vinyl-N-t-butoxycarbonylbenzylamine obtained in Production Example 2-11, and 40 mL of toluene were placed in a 50-mL test tube purged with nitrogen, and the resulting mixture was stirred at 110° C. for 13 hours. After the obtained reaction mixture was cooled to 25° C., filtration was performed, and the obtained filtrate was concentrated under reduced pressure, thereby obtaining 0.07 g of a compound represented by the above formula (DMIm-pVPMI) (yield: 32%). The $^1$H-NMR analysis results of DMIm-pVPMI are shown below.

$^1$H-NMR (DMSO-d6) δ (ppm)=7.45 (s, 2H), 7.42-7.20 (m, 4H), 6.71 (dd, J=18.0, 10.8 Hz, 1H), 5.76 (dd, J=17.6, 0.8 Hz, 1H), 5.18 (dd, J=10.8, 0.8 Hz, 1H), 4.40 (s, 2H), 3.99 (s, 6H)

Synthesis Example 2-12: Synthesis of DMIm-mMDI

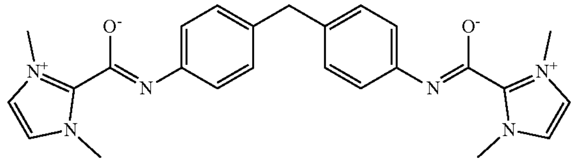 [SMILES: Cn1cc[n+](C)c1/C([O-])=N/c1ccc(Cc2ccc(/N=C(\[O-])c3n(C)cc[n+]3C)cc2)cc1]

3.0 g (22 mmol) of DMIm-$CO_2$ obtained in Production Example 1-1, 3.5 g (11 mmol) of bis[4-(t-butoxycarbonylamino)phenyl]methane obtained in Production Example 2-17, and 120 mL of chlorobenzene were placed in a 200-mL test tube purged with nitrogen, and the resulting mixture was stirred at 130° C. for 3 hours. Concentration under reduced pressure was performed, thereby obtaining 3.9 g of a compound represented by the above formula (DMIm-mMDI) (yield: 81%). The $^1$H-NMR analysis results of DMIm-mMDI are shown below.

$^1$H-NMR (DMSO-d6) δ (ppm)=7.51 (s, 4H), 7.41 (d, J=8.2 Hz, 4H), 6.95 (d, J=8.2 Hz, 4H), 3.99 (s, 12H), 3.83 (s, 2H)

Synthesis Example 2-13: Synthesis of DMIm-4,4'-(1,4-PBDMM)BPI

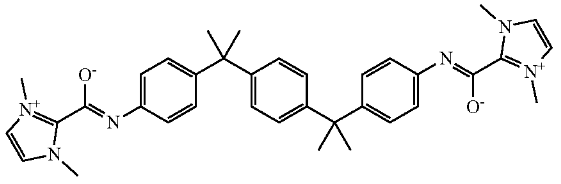 [SMILES: Cn1cc[n+](C)c1/C([O-])=N/c1ccc(C(C)(C)c2ccc(C(C)(C)c3ccc(/N=C(\[O-])c4n(C)cc[n+]4C)cc3)cc2)cc1]

0.20 g (1.4 mmol) of DMIm-$CO_2$ obtained in Production Example 1-1, 8 mL of chlorobenzene, and 0.39 g (0.7 mmol) of 1,4-bis{2-[4-(t-butoxycarbonylamino)phenyl]-2-propyl}benzene obtained in Production Example 2-12 were placed in a three-necked flask purged with nitrogen, and the resulting mixture was stirred at 130° C. for 3 hours. After the obtained reaction mixture was cooled to 25° C., filtration was performed, and the obtained yellow solid was dried under reduced pressure, thereby obtaining 0.30 g of a compound represented by the above formula (DMIm-4,4'-(1,4-PBDMM)BPI) (yield: 73%). The $^1$H-NMR analysis results of DMIm-4,4'-(1,4-PBDMM)BPI are shown below.

$^1$H-NMR (DMSO-d6) δ (ppm)=7.50 (s, 4H), 7.37 (d, J=8.4 Hz, 4H), 7.10 (s, 4H), 6.98 (d, J=8.4 Hz, 4H), 3.98 (s, 12H), 1.58 (s, 12H)

Synthesis Example 2-14: Synthesis of DMIm-4,4'-(1,3-PBDMM)BPI

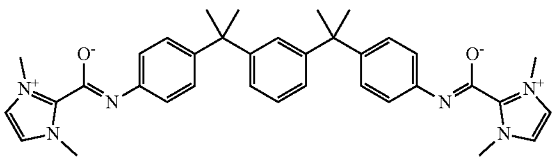 [SMILES: Cn1cc[n+](C)c1/C([O-])=N/c1ccc(C(C)(C)c2cccc(C(C)(C)c3ccc(/N=C(\[O-])c4n(C)cc[n+]4C)cc3)c2)cc1]

1.5 g (11.0 mmol) of DMIm-$CO_2$ obtained in Production Example 1-1, 100 mL of chlorobenzene, and 3.0 g (5.5 mmol) of 1,3-bis {2-[4-(t-butoxycarbonylamino)phenyl]-2-propyl}benzene obtained in Production Example 2-13 were placed in a three-necked flask purged with nitrogen, and the resulting mixture was stirred at 130° C. for 3 hours. The obtained reaction mixture was cooled to 25° C., and then dried under reduced pressure. The obtained solid was washed 3 times with 100 ml of toluene, and dried under reduced pressure, thereby obtaining 2.23 g of a compound represented by the above formula (DMIm-4,4'-(1,3-PBDMM)BPI) (yield: 55%).

$^1$H-NMR (DMSO-d6) δ (ppm)=7.53 (s, 4H), 7.42-7.39 (m, 4H), 7.12 (s, 1H), 6.98-6.96 (m, 7H), 4.00 (s, 12H), 1.58 (s, 12H)

Synthesis Example 2-15: Synthesis of DMIm-4,4'-(1,3-PBO)BPI

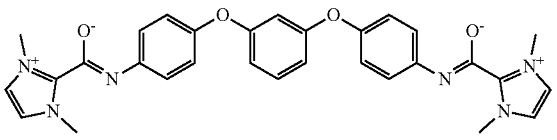 [SMILES: Cn1cc[n+](C)c1/C([O-])=N/c1ccc(Oc2cccc(Oc3ccc(/N=C(\[O-])c4n(C)cc[n+]4C)cc3)c2)cc1]

2.0 g (14 mmol) of DMIm-$CO_2$ obtained in Production Example 1-1, 80 mL of chlorobenzene, and 3.5 g (7.1 mmol) of 1,3-bis[4-(t-butoxycaronylamino)phenoxy]benzene obtained in Production Example 2-14 were placed in a three-necked flask purged with nitrogen, and the resulting mixture was stirred at 130° C. for 3 hours. The obtained reaction mixture was cooled to 25° C., and then dried under reduced pressure, thereby obtaining 3.80 g of a compound represented by the above formula (DMIm-4,4'-(1,3-PBO)BPI) (yield: 99%). The $^1$H-NMR analysis results of DMIm-4,4'-(1,3-PBO)BPI are shown below.

$^1$H-NMR ($CD_3OD$) δ (ppm)=7.47 (s, 4H), 7.42 (d, J=9.0 Hz, 4H), 7.23 (t, J=8.2 Hz, 1H), 6.96 (d, J=9.0 Hz, 4H), 6.63 (dd, J=8.2, 2.4 Hz, 2H), 6.57 (t, J=2.4 Hz, 1H), 3.98 (s, 12H)

Synthesis Example 2-16: Synthesis of DMIm-3,3'-SO2BPI

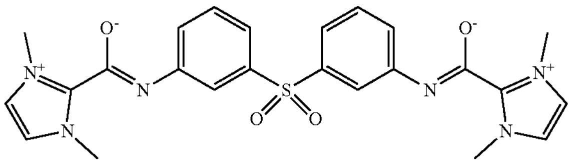 [SMILES: Cn1cc[n+](C)c1/C([O-])=N/c1cccc(S(=O)(=O)c2cccc(/N=C(\[O-])c3n(C)cc[n+]3C)c2)c1]

0.6 g (4.5 mmol) of DMIm-$CO_2$ obtained in Production Example 1, 1.0 g (2.2 mmol) of bis[3-(t-butoxycarbonylamino)phenyl]sulfone obtained in Production Example 2-15, and 18 mL of chlorobenzene were placed in a 30-mL test tube purged with nitrogen, and the resulting mixture was stirred at 130° C. for 6 hours. After the obtained reaction mixture was cooled to 25° C., filtration was performed, and the obtained brown solid was dried under reduced pressure, thereby obtaining 1.3 g of a compound represented by the above formula (DMIm-3,3'-SO2BPI) (pure content: 1.1 g, yield: 99%). The H-NMR analysis results of DMIm-3,3'-SO2BPI are shown below.

$^1$H-NMR (DMSO-d6) δ (ppm)=7.68 (s, 2H), 7.63 (d, J=7.3 Hz, 2H), 7.56 (s, 4H), 7.44-7.38 (m, 2H), 7.34-7.30 (m, 2H), 4.01 (s, 12H)

Synthesis Example 2-17: Synthesis of BMIm-PI

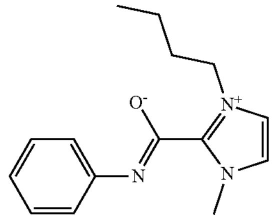 [SMILES: CCCC[n+]1ccn(C)c1/C([O-])=N/c1ccccc1]

6.0 g (pure content: 16 mol) of the methanol solution of BMIm-$CO_2$ obtained in Production Example 2-1, 1.9 g (16 mmol) of phenyl isocyanate, and 100 mL of toluene were placed in a 200-mL test tube purged with nitrogen. The obtained mixture was stirred at an internal temperature of 110° C. for 3 hours. Concentration under reduced pressure was performed, thereby obtaining 4.1 g of a compound represented by the above formula (BMIm-PI) (yield: 97%). The $^1$H-NMR analysis results of the compound represented by the above formula are shown below.

$^1$H-NMR ($CD_3OD$) δ (ppm)=7.53 (s, 1H), 7.47 (s, 1H), 7.33-7.25 (m, 4H), 7.00 (t, J=7.2 Hz, 1H), 4.38 (t, J=7.4 Hz, 2H), 3.98 (s, 3H), 1.89 (quint, J=7.6 Hz, 2H), 1.39 (sext, J=7.4 Hz, 2H), 0.97 (t, J=7.2 Hz, 3H)

Synthesis Example 2-18: Synthesis of OMIm-PI

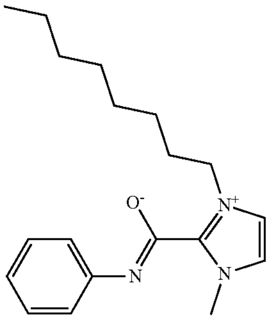 [SMILES: CCCCCCCC[n+]1ccn(C)c1/C([O-])=N/c1ccccc1]

4.0 g (pure content: 13 mmol) of the methanol solution of OMIm-$CO_2$ obtained in Production Example 2-2, 1.5 g (13 mmol) of phenyl isocyanate, and 100 mL of toluene were placed in a 200-mL test tube purged with nitrogen. The obtained mixture was stirred at an internal temperature of 110° C. for 3 hours. Concentration under reduced pressure was performed, thereby obtaining 3.3 g of a compound represented by the above formula (OMIm-PI) (yield: 84%). The $^1$H-NMR analysis results of the compound represented by the above formula are shown below.

$^1$H-NMR ($CD_3OD$) δ (ppm)=7.51 (s, 1H), 7.45-7.33 (m, 6H), 4.37 (t, J=7.4 Hz, 2H), 3.97 (s, 3H), 1.91-1.86 (m, 2H), 1.35-1.27 (m, 10H), 0.88 (t, J=6.8 Hz, 3H)

Synthesis Example 2-19: Synthesis of OMIm-mMDI

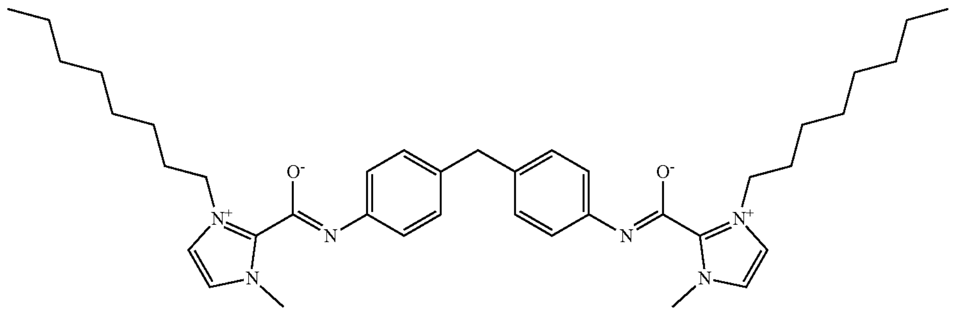 [SMILES: CCCCCCCC[n+]1ccn(C)c1/C([O-])=N/c1ccc(Cc2ccc(/N=C(\[O-])c3n(C)cc[n+]3CCCCCCCC)cc2)cc1]

4.9 g (pure content: 15 mmol) of the methanol solution of OMIm-$CO_2$ obtained in Production Example 2-2, 100 mL of chlorobenzene, and 2.5 g (6.3 mol) of bis[4-(t-butoxycarbonylamino)phenyl]methane obtained in Production Example 2-17 were placed in a three-necked flask purged with nitrogen, and the resulting mixture was stirred at 130° C. for 5 hours. The obtained reaction mixture was cooled to 25° C., and then dried under reduced pressure, thereby obtaining 4.65 g of a compound represented by the above formula (OMIm-mMDI) (pure content: 4.0 g, yield: 99%). The $^1$H-NMR analysis results of OMIm-mMDI are shown below.

$^1$H-NMR ($CD_3OD$) δ (ppm)=7.51 (m, 2H), 7.45 (m, 2H), 7.35-7.34 (m, 4H), 7.13-7.11 (m, 4H) 4.35 (t, J=7.4 Hz, 4H), 3.95 (s, 6H), 3.90 (s, 2H), 1.88 (m, 4H), 1.34-1.26 (m, 20H), 0.87 (t, J=7.6 Hz, 6H)

Synthesis Example 2-20: Synthesis of DMIm-pClPI 0.20 g (1.43 mol) of DMIm-$CO_2$ obtained in Production Example 1-1, 0.26 g (1.43 mmol) of p-chloro-N-methoxycarbonylaniline obtained in Production Example 2-18, and 6 mL of toluene were placed in a 15-mL test tube purged with nitrogen, and the resulting mixture was stirred at 110° C. for 3 hours. After the obtained reaction mixture was cooled to 25° C., filtration was performed, and the obtained white solid was dried under reduced pressure, thereby obtaining 0.36 g of a compound represented by the above formula (DMIm-pClPI) (yield: 92%).

Synthesis Example 2-21: Synthesis of DMIm-pClPI 0.34 g (2.39 mmol) of DMIm-$CO_2$ obtained in Production Example 1-1, 0.51 g (2.39 mmol) of p-chloro-N-isopropoxycarbonylaniline obtained in Production Example 2-19, and 9 mL of toluene were placed in a 30-mL test tube purged with nitrogen, and the resulting mixture was stirred at 110° C. for 6 hours. After the obtained reaction mixture was cooled to 25° C., filtration was performed, and the obtained white solid was dried under reduced pressure, thereby obtaining 0.49 g of DMIm-pClPI (yield: 82%).

Synthesis Example 2-22: Synthesis of DMIm-pClPI 0.30 g (2.14 mmol) of DMIm-$CO_2$ obtained in Production Example 1-1, 0.61 g (2.14 mmol) of p-chloro-N-octoxycarbonylaniline (p-chloro-N-(n-octyloxy) carbonylaniline) obtained in Production Example 2-20, and 9 mL of toluene were placed in a 30-mL test tube purged with nitrogen, and the resulting mixture was stirred at 110° C. for 3 hours. After the obtained reaction mixture was cooled to 25° C., filtration was performed, and the obtained white solid was dried under reduced pressure, thereby obtaining 0.38 g of DMIm-pClPI (yield: 72%).

Synthesis Example 2-23: Synthesis of DMIm-pClPI 0.30 g (2.14 mmol) of DMIm-$CO_2$ obtained in Production Example 1-1, 0.53 g (2.14 mmol) of p-chloro-N-phenoxycarbonylaniline obtained in Production Example 2-21, and 9 mL of toluene were placed in a 30-mL test tube purged with nitrogen, and the resulting mixture was stirred at 110° C. for 3 hours. The obtained reaction mixture was cooled to 25° C., and then concentrated under reduced pressure, thereby obtaining a mixture of DMIm-pClPI and phenol. The $^1$H-NMR analysis of the obtained mixture showed that the yield of DMIm-pClPI was 98%.

Evaluation Example 1-1: Stability Evaluation of $DMIm-CO_2$

A heating test was conducted in such a manner that deuterium oxide and $DMIm-CO_2$ at 1 wt. % based on the deuterium oxide were placed in an NMR tube and heated to 80° C. While the purity before the heating test was regarded as 100%, the residual ratio (%) of $DMIm-CO_2$ after the heating test was calculated, and stability was evaluated. The heating time was set to 1 hour and 3 hours. The residual ratio (%) of $DMIm-CO_2$ was calculated from the integral values of the $DMIm-CO_2$ peak (δ=around 3.95 ppm) determined by $^1$H-NMR analysis and the impurity peak (δ=around 3.85 ppm), which increased with heating, using the following formulas. Table 1 shows the results. In Evaluation Example 1-1, the residual ratio (%) when the heating time was 6 hours was not evaluated.

Residual ratio (%)=purity (%) after heating/purity (%) before heating×100

Purity (%)=$DMIm-CO_2$ peak integral value/($DMIm-CO_2$ peak integrated intensity+impurity peak integral value)×100.

Evaluation Example 1-2: Stability Evaluation of DMIm-PI

The stability of DMIm-PI was evaluated using DMIm-PI in place of $DMIm-CO_2$ in Evaluation Example 1-1. Because DMIm-PI was poorly soluble in water, a mixed solution of deuterium oxide and heavy dimethylsulfoxide was used in place of deuterium oxide in Evaluation Example 1-1, and the stability of DMIm-PI was evaluated under 80° C. heating as in Evaluation Example 1-1. The heating time was set to 1 hour, 3 hours, and 6 hours. The residual ratio (%) of DMIm-PI was calculated from the integral values of the DMIm-PI peak (8=around 3.78 ppm) determined by 1H-NMR analysis and the impurity peak (6=around 3.72 ppm), which increased with heating. Table 1 shows the results.

Evaluation Example 1-3: Stability Evaluation of DMIm-pClPI

Evaluation was performed as in Evaluation Example 1-2, except that DMIm-pClPI was used in place of DMIm-PI in Evaluation Example 1-2. The heating time was set to 1 hour, 3 hours, and 6 hours. The residual ratio (%) of DMIm-pClPI was calculated from the integration values of the DMIm-pClPI peak (δ=around 3.79 ppm) determined by $^1$H-NMR analysis and the impurity peak (δ=around 3.74 ppm), which increased with heating. Table 1 shows the results.

TABLE 1

| | Residual ratio (%) | | |
|---|---|---|---|
| Heating time | Evaluation Example 1-1 | Evaluation Example 1-2 | Evaluation Example 1-3 |
| 0 hr | 100.0 | 100.0 | 100.0 |
| 1 hr | 46.4 | 92.1 | 95.8 |
| 3 hr | 7.4 | 87.2 | 91.4 |
| 6 hr | — | 79.1 | 86.0 |

As shown in Table 1, the stability of DMIm-PI and DMIm-pClPI, both of which were amidate compounds, at 80° C. in the presence of water was higher than that of $DMIm-CO_2$, which was a carboxylate compound.

Example 1-1

1.8 g of polyol (Sanix GP3000, produced by Sanyo Chemical Industries, Ltd.), 0.2 g (NCO index: 100%) of isophorone diisocyanate (produced by Tokyo Chemical Industry Co., Ltd.), and 0.1 g of DMIm-PI as a curing catalyst were placed in a test tube to thereby prepare a urethane resin composition. The obtained urethane resin composition was heated at various temperatures for 10 minutes, and the curing temperature was measured. Table 2 shows the results.

Examples 1-2 to 1-4 and 2-1 to 2-11

The same procedure was performed as in Example 1-1, except that DMIm-PI was replaced with the compounds shown in Table 2 in Example 1-1. Table 2 shows the results.

Comparative Example 1-1

The same procedure was performed as in Example 1-1, except that a urethane resin composition was prepared without adding DMIm-PI in Example 1-1. Table 2 shows the results.

Comparative Example 1-2

The same procedure was performed as in Example 1-1, except that DMIm-PI was replaced with dibutyltin dilaurate in Example 1-1. Table 2 shows the results.

Comparative Example 2-1

The same procedure was performed as in Example 1-1, except that DMIm-PI was replaced with $DMIm-CO_2$ in Example 1-1. Table 2 shows the results.

TABLE 2

| | | Temperature (° C.) | | | | | | | |
|---|---|---|---|---|---|---|---|---|---|
| | Curing catalyst | 25 | 40 | 60 | 80 | 100 | 120 | 140 | 160 |
| Example 1-1 | DMIm-PI | − | − | − | − | − | − | − | + |
| Example 1-2 | DMIm-pCIPI | − | − | − | − | − | − | + | + |
| Example 1-3 | DMIm-BI | − | − | − | − | − | − | − | + |
| Example 1-4 | DMIm-TDI | − | − | − | − | − | − | − | + |
| Example 2-1 | DMIm-oCIPI | − | − | − | − | − | + | + | + |
| Example 2-2 | DMIm-mCIPI | − | − | − | − | − | + | + | + |
| Example 2-3 | DMIm-piPrPI | − | − | − | − | − | + | + | + |
| Example 2-4 | DMIm-pOctPI | − | − | − | − | − | − | + | + |
| Example 2-5 | DMIm-pMeOPI | − | − | − | − | − | + | + | + |
| Example 2-6 | DMIm-26DiPrPI | − | − | − | − | − | + | + | + |

TABLE 2-continued

| | Curing catalyst | Temperature (° C.) 25 | 40 | 60 | 80 | 100 | 120 | 140 | 160 |
|---|---|---|---|---|---|---|---|---|---|
| Example 2-7 | BMIm-PI | − | − | − | − | − | − | + | + |
| Example 2-8 | OMIm-PI | − | − | − | − | − | + | + | + |
| Example 2-9 | DMIm-mMDI | − | − | − | − | − | − | − | + |
| Example 2-10 | DMIm-4,4'-(1,3-PBDMM)BPI | − | − | − | − | − | + | + | + |
| Example 2-11 | DMIm-4,4'-(1,3-PBO)BPI | − | − | − | − | − | − | + | + |
| Comparative Example 1-1 | None | − | − | − | − | − | − | − | − |
| Comparative Example 1-2 | Dibutyltin dilaurate | − | − | − | + | + | + | + | + |
| Comparative Example 2-1 | DMIm-$CO_2$ | − | − | − | − | − | − | + | + |

Curability evaluation
+: Urethane resin composition had fluidity
−: Urethane resin composition had no fluidity As shown in Table 2, the urethane resin compositions, to which the compound of the present invention was added, were stable at 100° C. or less, without progression of curing; however, they were cured at 160° C. when any catalyst was used. This revealed that the compound of the present invention can be used as a catalyst for polyurethane production, particularly as a thermally latent catalyst.

The invention claimed is:

1. An amidate compound represented by formula (1):

(1)

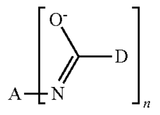

wherein A is a substituted or unsubstituted hydrocarbon group, n is an integer of 1 or more, and D is a nitrogen-containing organic group represented by formula (2-1):

(2-1)

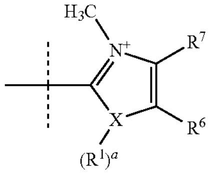

wherein $R^1$ is a hydrocarbon group that may contain a heteroatom; $R^6$ and $R^7$ are the same or different, and are each a hydrogen atom or a $C_1$-$C_6$ hydrocarbon group that may contain a heteroatom; X is a nitrogen atom; and a is 1;

provided that 1,3-dimethylimidazolium-2-N-(p-chlorophenyl)amidate and 1,3-dimethylimidazolium-2-N-(3',5'-dichlorophenyl)amidate are excluded.

2. The amidate compound according to claim 1, wherein A is an unsubstituted hydrocarbon group or a hydrocarbon group having at least one substituent selected from the group consisting of a fluorine atom, an alkylamino group, a dialkylamino group, an alkoxy group, an aryloxy group, a nitro group, a cyano group, a sulfonyl group, and an isocyanate group.

3. The amidate compound according to claim 1, wherein n is an integer of 1 to 6.

4. The amidate compound according to claim 1, wherein the amidate compound represented by the formula (1) is an amidate compound represented by the following formula (1-1), (1-2), or (1-3):

Formula (1-1):

(1-1)

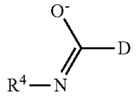

wherein $R^4$ is a substituted or unsubstituted hydrocarbon group, and D is as defined in claim 1;

Formula (1-2)

(1-2)

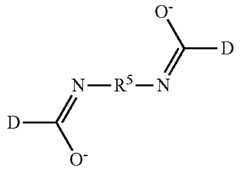

wherein $R^5$ is a substituted or unsubstituted hydrocarbon group, and D is as defined in claim 1; or Formula (1-3)

(1-3)

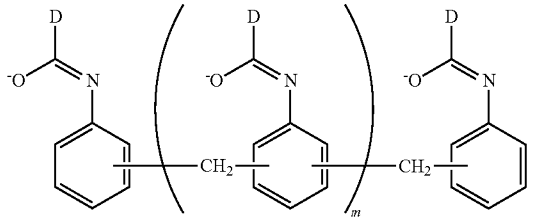

wherein m is an integer of 0 to 4, and D is as defined in claim 1.

5. The amidate compound according to claim 1, wherein the amidate compound is at least one selected from the group consisting of:
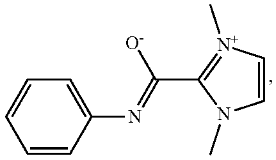,
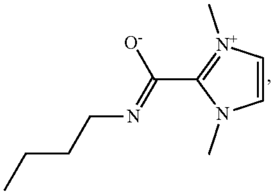,
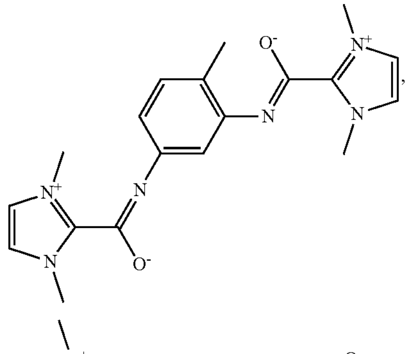,
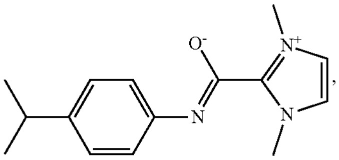,
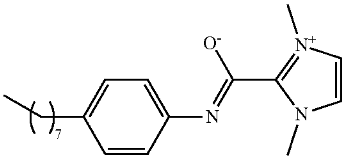,
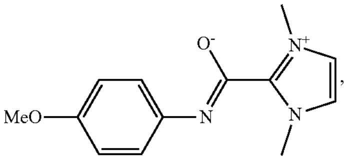,
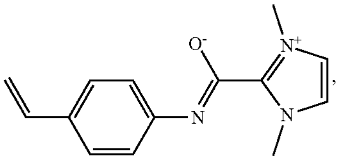,
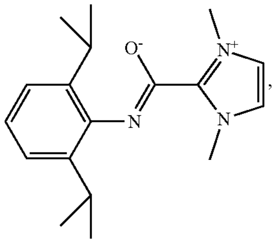,
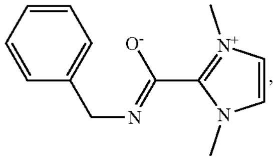,
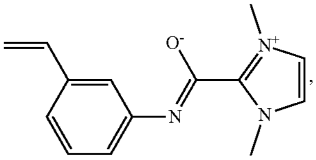,
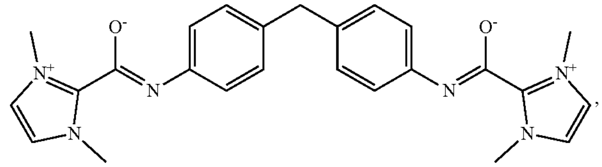,
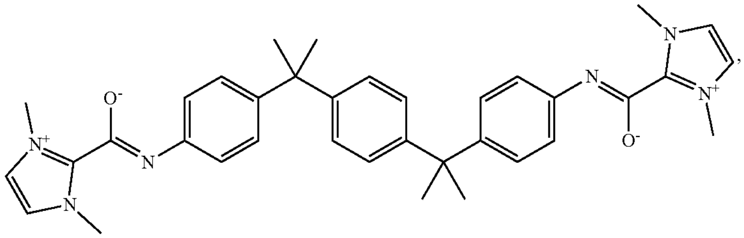,
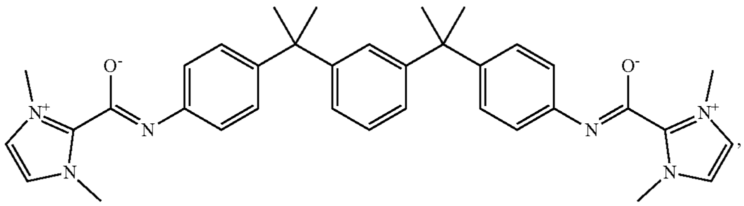,
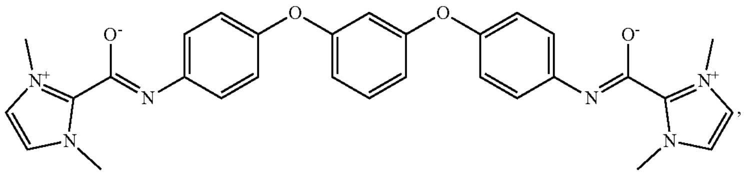, -continued

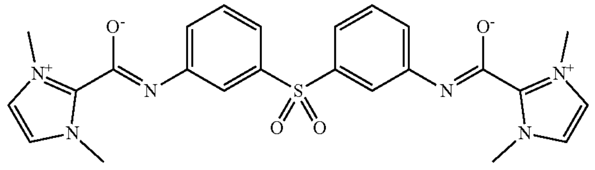
,
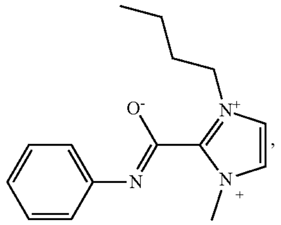
,
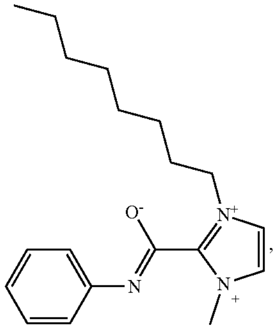
, and
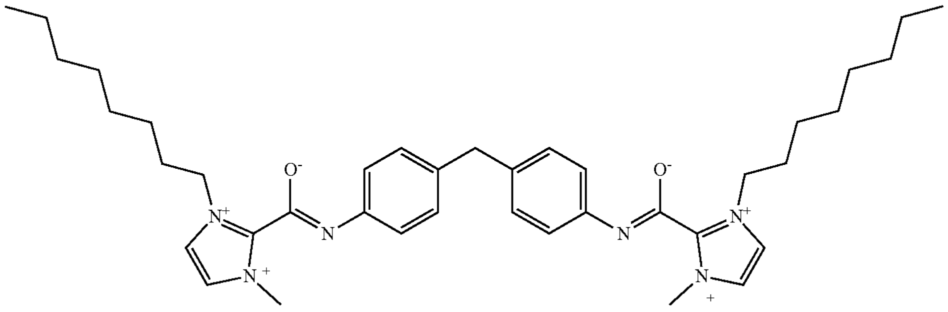
.

6. A catalyst for polyurethane production comprising an amidate compound represented by formula (1):

(1)

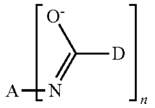

wherein A is a substituted or unsubstituted hydrocarbon group, n is an integer of 1 or more, and D is a nitrogen-containing organic group represented by formula (2-1):

(2-1)

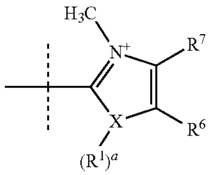

wherein $R^1$ is a hydrocarbon group that may contain a heteroatom; $R^6$ and $R^7$ are the same or different, and are each a hydrogen atom or a $C_1$-$C_6$ hydrocarbon group that may contain a heteroatom: X is a nitrogen atom; and a is 1.

7. The catalyst for polyurethane production according to claim 6, wherein A is an unsubstituted hydrocarbon group or a hydrocarbon group having at least one substituent selected from the group consisting of a halogen atom, an alkylamino group, a dialkylamino group, an alkoxy group, an aryloxy group, a halogenated alkyl group, a nitro group, a cyano group, a sulfonyl group, and an isocyanate group.

8. The catalyst for polyurethane production according to claim 6, wherein n is an integer of 1 to 6.

9. The catalyst for polyurethane production according to claim 6, wherein the amidate compound represented by the formula (1) is an amidate compound represented by the following formula (1-1), (1-2), or (1-3):

Formula (1-1)

(1-1)

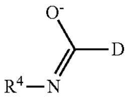

wherein $R^4$ is a substituted or unsubstituted hydrocarbon group, and D is as defined in claim 6;

Formula (1-2)
(1-2)
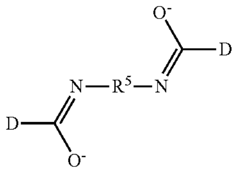
wherein $R^5$ is a substituted or unsubstituted hydrocarbon group, and D is as defined in claim 6; or
Formula (1-3):
(1-3)
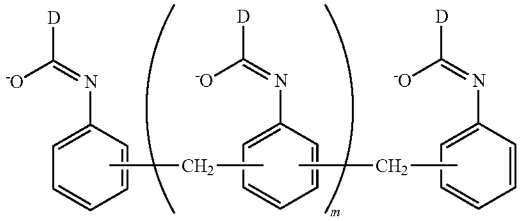
wherein m is an integer of 0 to 4, and D is as defined in claim 6.
10. The catalyst for polyurethane production according to claim 6, wherein the amidate compound is at least one selected from the group consisting of:
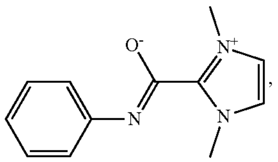,
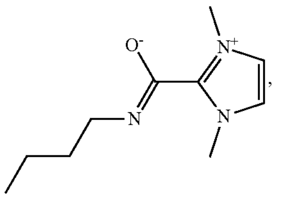,
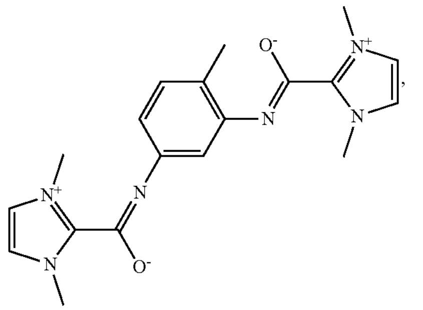,
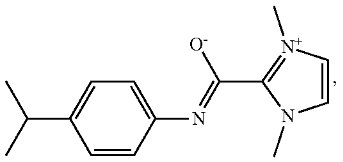,
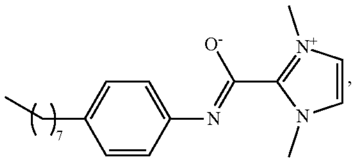,
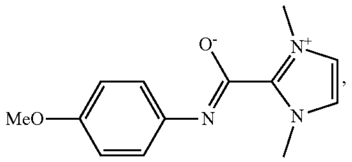,
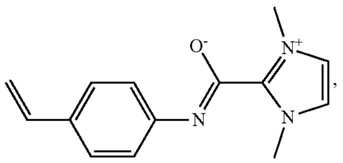,
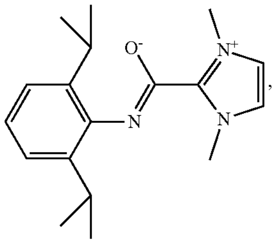,
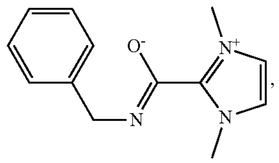, -continued
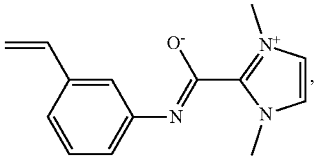
,
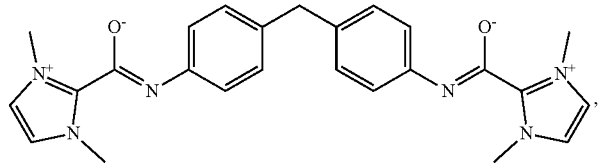
,
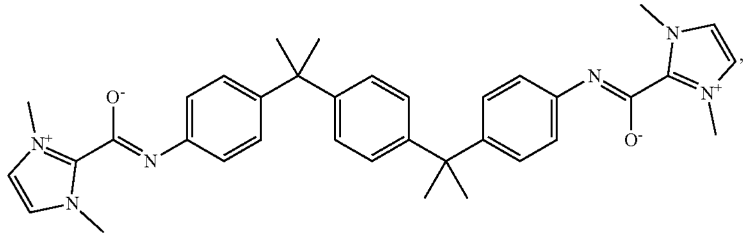
,
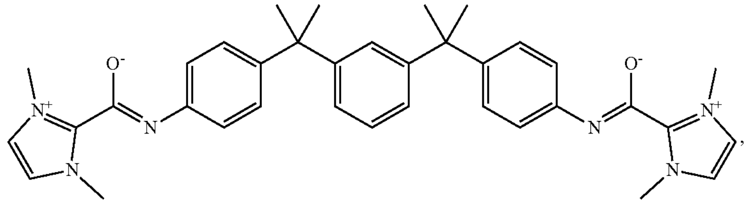
,
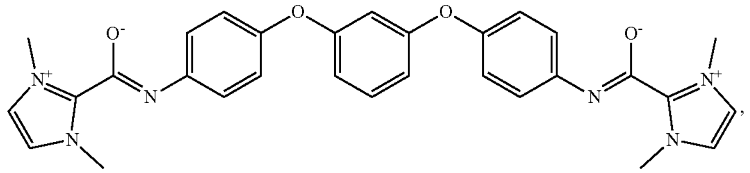
,
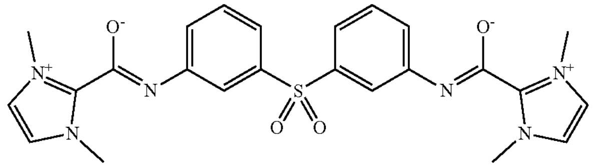
,
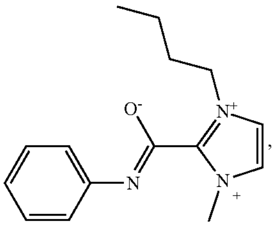
,
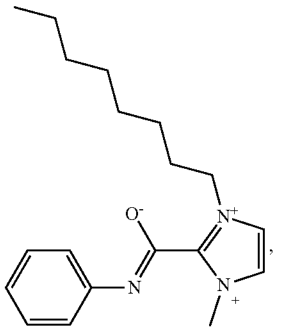
, and
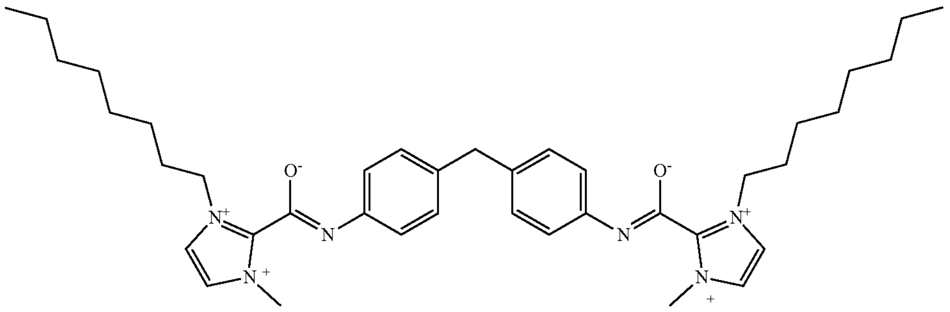
.

11. A method for producing a polyurethane resin, the method comprising reacting a polyol and a polyisocyanate in the presence of the catalyst for polyurethane production according to claim 6.

12. A method for producing the amidate compound according to claim 1, the method comprising the following steps 1 and 2:

step 1: reacting a nitrogen-containing organic compound represented by the following formula (3-1) and dimethyl carbonate to produce a carboxylate compound represented by the following formula (4-1):

Formula (3-1)

(3-1)

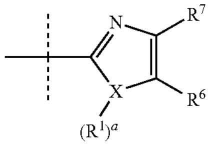

wherein $R^1$, $R^6$, $R^7$, X, and a are as defined in claim 1;

Formula (4-1):

(4-1)

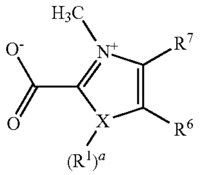

wherein $R^1$, $R^6$, $R^7$, X, and a are as defined in claim 1; and step 2: reacting the carboxylate compound represented by the formula (4-1) and an isocyanate compound represented by the following formula (5):

Formula (5):

$$A\text{-}[NCO]_n \qquad (5)$$

wherein A and n are as defined in claim 1.

13. The method according to claim 12, wherein in step 2, the reaction is performed in the presence of a hydrocarbon solvent.

14. The method according to claim 13, wherein the hydrocarbon solvent is an aromatic hydrocarbon solvent or a halogenated aromatic hydrocarbon solvent.

15. The method according to claim 14, wherein the aromatic hydrocarbon solvent or the halogenated aromatic hydrocarbon solvent is selected from the group consisting of toluene, xylene, and chlorobenzene.

* * * * *